(12) United States Patent
Yan

(10) Patent No.: US 9,132,228 B2
(45) Date of Patent: Sep. 15, 2015

(54) FLUID DELIVERY SYSTEM

(76) Inventor: Eric Yan, San Francisco, CA (US)

( * ) Notice: Subject to any disclaimer, the term of this patent is extended or adjusted under 35 U.S.C. 154(b) by 121 days.

(21) Appl. No.: 13/372,443

(22) Filed: Feb. 13, 2012

(65) Prior Publication Data

US 2012/0209243 A1 Aug. 16, 2012

Related U.S. Application Data

(60) Provisional application No. 61/442,250, filed on Feb. 13, 2011, provisional application No. 61/474,753, filed on Apr. 13, 2011.

(51) Int. Cl.
| | |
|---|---|
| *A61M 5/20* | (2006.01) |
| *A61M 5/142* | (2006.01) |
| *A61M 5/168* | (2006.01) |
| *A61M 39/10* | (2006.01) |
| *B05B 1/14* | (2006.01) |
| *B05B 1/20* | (2006.01) |
| *B05B 1/30* | (2006.01) |
| *A61M 5/00* | (2006.01) |

(52) U.S. Cl.
CPC .............. *A61M 5/142* (2013.01); *A61M 5/008* (2013.01); *A61M 5/16827* (2013.01); *A61M 39/10* (2013.01); *B05B 1/14* (2013.01); *B05B 1/202* (2013.01); *B05B 1/205* (2013.01); *B05B 1/30* (2013.01); *A61M 2039/1083* (2013.01); *A61M 2039/1088* (2013.01); *A61M 2205/14* (2013.01); *A61M 2205/60* (2013.01); *A61M 2205/6063* (2013.01)

(58) Field of Classification Search
CPC A61M 5/1413; A61M 5/168; A61M 5/16827
USPC .......................................................... 604/131
See application file for complete search history.

(56) References Cited

U.S. PATENT DOCUMENTS

| | | | | |
|---|---|---|---|---|
| 4,655,751 | A * | 4/1987 | Harbaugh | 604/198 |
| 5,873,731 | A * | 2/1999 | Prendergast | 434/262 |
| 7,074,209 | B2 * | 7/2006 | Evans et al. | 604/189 |
| 7,442,181 | B2 | 10/2008 | Schubert et al. | |
| 2004/0082918 | A1 | 4/2004 | Evans et al. | |
| 2004/0122371 | A1 * | 6/2004 | Neer et al. | 604/152 |
| 2007/0135765 | A1 * | 6/2007 | Miller et al. | 604/131 |
| 2011/0021905 | A1 * | 1/2011 | Patrick et al. | 600/424 |

FOREIGN PATENT DOCUMENTS

WO 2012109678 A2 8/2012

OTHER PUBLICATIONS

Yoo, Min Jeong, International Search Report and Written Opinion for PCT/US2012/024929, Date of Mailing of the ISR Aug. 24, 2012.

* cited by examiner

*Primary Examiner* — Laura Bouchelle
(74) *Attorney, Agent, or Firm* — Joseph R. Baker, Jr.; Gavrilovich, Dodd & Lindsey LLP

(57) ABSTRACT

The disclosure is directed to a fluid delivery device and a removable cartridge system, and methods of use thereof.

18 Claims, 29 Drawing Sheets

FLUID DELIVERY SYSTEM

CROSS REFERENCE TO RELATED APPLICATIONS

This application claims priority under 35 U.S.C. §119 from Provisional Application Ser. No. 61/442,250, filed Feb. 13, 2011 and from Provisional Application Ser. No. 61/474,753, filed Apr. 13, 2011, the disclosures of which are incorporated herein by reference.

TECHNICAL FIELD

This disclosure relates to a fluid delivery device and a dual fluid cartridge system and methods of use thereof, such as the delivery of fluids in medical, industrial, commercial and scientific settings.

BACKGROUND

A 1978 landmark article highlighted the problem of drug errors (Cooper et al., "Preventable anesthesia mishaps: a human factors study," *Anesthesiology* 49:399-406 (1978)). The investigators' found that mistaking syringes and ampules accounted for 14%, or the second most common cause, of preventable drug errors during anesthesia. This type of error was topped only by delivering incorrect gas to the patient, which occurred over 25% of the time. Follow-on studies as recent as 1985 continued to show that the most common cause of drug related error involved anesthetic gases. The concern highlighted by this study was that human error, such as unfamiliarity with machine operation and safety features, was the root of the problem in over 80% of these cases. Accumulating evidence from more recent studies show that errors involving the delivery of fresh gas accounted for far fewer errors of any type in anesthesia. Instead, these errors are now replaced by the delivery of intravenous medications. Intravenous medication errors occur with an incidence of between 0.11-0.75% with the most likely cause of error being mistaking drugs or syringes, overdose, or incorrect dosages. All told, 2% of all patients were injured as a result of errors and another 5.5% were exposed to near misses, where the correction of a mistake or good fortune, allowed the patient to escape unharmed.

SUMMARY

The disclosure provides for a fluid delivery device. The disclosure further provides that the fluid delivery device can deliver metered doses of fluids in an accurate and precise manner.

The disclosure provides for a fluid delivery device comprising: (a) an elongate member having a first and second end; (b) a plurality of fluid cartridge adapters spaced along the length of the elongate member, wherein each adapter is adapted to receive fluid from a removable fluid cartridge; (c) a fluid channel that is centrally disposed within the elongate member and fluidly linked to the fluid cartridge adapters, wherein the fluid channel's first end is enclosed in the elongate member while the second end is fluidly linked to an exit portal; (d) one or more pressure modifying devices that are pressureably linked to the fluid channel so that a change in pressure from the pressure modifying device causes liquid to move into the fluid channel; and (e) one or more detectors which can detect one or more machine readable indicators on a removable fluid cartridge once the removable fluid cartridge is inserted into the fluid delivery device, and then the detectors can output information provided by the machine readable indicator to a computer.

In a particular embodiment, the disclosure provides for the fluid delivery device disclosed comprising a structural housing so dimensioned as to contact the elongate member and restrict the elongate member's movement. In another embodiment, the structural housing can prevent the movement of one or more removable fluid cartridges from a substantially vertical position. In a further embodiment, the structural housing is further comprised of tubing, wherein the tubing can be reversibly attached to one or more injection ports of a removable fluid cartridge, and can also be reversibly connected to a pressuring modifying device. In yet a further embodiment, the structural housing can be comprised of a left and right support, one or more motor mount plates, one or more bearing plates, and one or more bearings.

In a particular embodiment, the disclosure provides for a fluid delivery device disclosed herein comprising a plurality of fluid cartridge holders so dimensioned as to receive removable fluid cartridges and restrict the movement of the cartridges from a substantially upright position. In another embodiment, the fluid cartridge holders can be attached to fluid cartridge adapters. In alternate embodiment, the fluid cartridge holders can be attached to the structural housing. In yet another embodiment, the fluid cartridge holders can be attached to the structural housing and fluid cartridge holders. In a certain embodiment, the fluid cartridge holders contain one or more holes which can be used to fix the fluid cartridge holders to the fluid cartridge adapters by using one or more locking pins. In a further embodiment, the fluid cartridge holders contain a notch which fits a notch-like projection on the fluid cartridge holders to provide proper orientation and/or prevent the fluid cartridge adapters from rotating around a horizontal axis. In yet a further embodiment, the fluid cartridge holders comprise a narrow window-like opening to facilitate the presentation of a machine readable indicator to a detector. In additional embodiment, the fluid cartridge holders are comprised of a fixed portion and a hingeably attached portion, wherein the hingeably attached portion can be attached and detached from the fixed portion of the holder. In a particular embodiment, the hingeably attached portion extends the entire height of the fluid cartridge holder. In a further embodiment, the hingeably attached portion of a cartridge holder can swing out in a bay door like manner to allow the insertion of a removable fluid cartridge.

In a particular embodiment, the disclosure provides for a fluid delivery device disclosed herein comprising a plurality of pre-filled removable fluid cartridges, wherein each removable fluid cartridge comprises a fluid ejection port, an injection port, and a machine readable indicator. In a particular embodiment, a removable fluid cartridge is in the form of a syringe. In another embodiment, the disclosure provides that one or more machine readable indicators comprises an optical machine-readable representation of data. In another embodiment, a detector, such as camera or bar code scanner, can detect the optical machine-readable representation of data. In a further embodiment, the optical machine-readable representation of data is selected from the group comprising, linear bar codes, matrix barcodes, QR codes, Aztec codes, and Shot-Codes. In a certain embodiment, the disclosure provides for one or more machine readable indicators comprising a microchip. In a further embodiment the microchip is comprised of a printed circuit board, and a transmitter. In yet a further embodiment, the microchip can communicate with a computer that has an attached or wireless device to receive the microchip's transmissions. In another embodiment, the microchip transmits read only information. Examples of such information, include: identifying a liquid, the status with respect to sterility of a liquid, the concentration of a liquid, volume of a liquid, lot number, dosage instructions, expiration date, drug indication warnings, data to facilitate supply chain management, expenses, and billing. In a further embodiment, the disclosure provides that the microchip can be reprogrammed by entering commands into a computer using a user interface. Examples of reprogramming include: updating and modifying the information about the contents of the cartridge. In a particular embodiment, the removable fluid cartridge comprises a one-way value that prevents fluid from entering the cartridge through the ejection port. Examples of one-way values include backwater valves, ball check valves, diaphragm check valves, swing check valves, stop-check valves, lift-check valves, and duckbill valves. In another embodiment, the disclosure provides for one or more of the removable fluid container cartridges to comprise a plurality of fluid doses, wherein the fluid can be delivered in a single dose or as multiple doses delivered in a continuous or periodic manner. In a further embodiment, the disclosure proves for a removable fluid cartridge comprised of an inner liner of a chemically inert material, and an outer liner of a chemically inert material or a non-chemically inert material. Examples of inert materials which can be used include, but are not limited to, glass, cyclic olefin polymeric materials, and pharmaceutical grade plastics. In yet another embodiment, the disclosure provides for a removable fluid cartridge comprising a pierceable port. In a certain embodiment, the pierceable port is made of a material, such as foil, plastic, or a membrane, that could be punctured by an object, such as a needle. In a further embodiment, the disclosure provides that the removable fluid cartridge is pre-filled with a liquid selected from the group comprising water, aqueous solute solutions, crystalloid solutions, liquids which contain one or more therapeutic agents, liquid intravenous medication, anesthetics, liquid based nutritional substances, oils, syrups, flavoring agents, chemicals that are in a liquid state, dissolved chemicals, and solvents.

In a particular embodiment, the disclosure provides for a fluid delivery device disclosed herein comprising one or more pressure regulating valves that can control the amount of pressure that each removable fluid cartridge receives. Examples of pressure regulating valves include solenoids, electronic actuators, pneumatic actuators, hydraulic actuators, handles, butterfly valves, plug valves, and pilot valves. In a certain embodiment, the pressure regulating valves can be opened or closed using a computer. In a further embodiment, the pressure regulating valves can be opened or closed by using commands from a user interface connected to a computer. Examples of a user interface include, but are not limited to, keyboards, mouse, light pens, and touchscreens.

In a particular embodiment, the disclosure provides for a fluid delivery device disclosed herein having an exit portal that is comprised of tubing. In another embodiment, a fluid delivery device disclosed herein having an exit portal comprised of tubing is further comprised of an in-line pressure exerting device, such as a peristaltic pump. In another embodiment, a fluid delivery device disclosed herein has an exit portal that is comprised of a holding tank and tubing. In a further embodiment, the holding tank is connected to a pump, wherein the pump provides one or more effects selected from the group comprising, drawing fluid from fluid channel into the holding tank, evacuating one or more gasses from the holding tank, and advancing fluid from the holding tank through tubing. In another embodiment, the tubing is surgical or pharmaceutical grade tubing. In a certain embodiment, the surgical or pharmaceutical grade tubing has a diameter from 0.1 to 1 inch. In a further embodiment, the pump is controllable by a computer. In yet a further embodiment, the pump's operation can be controlled by commands entered by a user on user interface connected to a computer. In a certain embodiment, a user interface may be connected to a computer that can be used to control the pump either directly, wirelessly, or remotely. In a further embodiment, the pump may be controlled by a computer that is accessed through the internet, network, or phone line from commands entered on a user interface that is connected to an alternate computer.

In a particular embodiment, the disclosure provides for a fluid delivery device disclosed herein comprising a computer. In another embodiment, the computer can receive and display the output from the detector. In yet another embodiment, the computer can be accessed directly, wirelessly, or remotely through the internet, phone line, or through a network. In yet another embodiment, the computer comprises a user interface to receive user commands. In a certain embodiment, the amount of fluid that is released from each removable fluid cartridge by entering commands on a user interface connected to a computer. In a certain embodiment, the amount of fluid that is released from each removable fluid cartridge is controlled by the amount of pressure or length of time the pressure is applied to one or more removable fluid cartridges by entering commands on a user interface that is connected to a computer. In another embodiment, the amount of fluid that is released from each removable fluid cartridge is controlled by modifying the amount of pressure that is applied to one or more removable fluid cartridges by using a user interface connected to a computer. In a preferred embodiment, the user interface is a touchscreen. In an additional embodiment, the computer is networked to one or more information storage devices. In a further embodiment, the one or more information storage devices provide information, including, but not limited to, electronic medical records, and contraindications for therapeutic agents. In yet a further embodiment, the user interface can relay information to the user from the computer or from connected information storage devices, including warnings, patient vital signs, dosing recommendations, and patient specific concerns. Specific examples of such information, include, but are not limited to, warnings related to giving fluids which may be contraindicated according to data supplied by information processing systems such as abnormal blood pressure, heart rate, breathing patterns, and oxygen saturation; providing recommendations of possible fluid dosages to address adverse clinical situation such as bradycardia, tachycardia, hypotension, hypertension, apnea, tachypnea, or desaturation; providing weight and ideal body weight of a subject; relevant information about fluid delivered such as medication name, drug class name, dosing guidelines, dosage, administration route, volume, expiration date, lot number, contraindications, adverse reactions, risk factors, special instructions, warnings, interactions, and monitoring parameters of fluid dosages; out of range of guidelines such as weight, blood pressure, and overbreathing the ventilator; name, concentration, volume, dosage and route of medication administration; location of medication administration; duration of medication administration; method of medication administration; provider's initials; date of medication delivery; time of medication delivery; and medication expiration date.

In a particular embodiment, the disclosure provides a fluid delivery device disclosed herein, wherein the pressure modifying device is pressureably linked to the fluid channel so as to provide positive pressure to push liquid from a removable fluid cartridge into the fluid channel. In an alternate embodiment, the disclosure provides for a fluid delivery device, wherein the pressure modifying device is operably linked to the fluid channel so as to provide negative pressure to draw liquid from a removable cartridge into fluid channel. Examples of pressure modifying devices include pumps, compressed gas cylinders, air compressors, vacuums, and building supplied air and vacuum sources. Moreover, the pressure modifying devices can exert pressure by increasing or decreasing air pressure, physical compression, injecting a gas or liquid, or a combination thereof. In a preferred embodiment, one or more pressured modifying devices are pumps, such as syringe pumps. In a certain embodiment, the pressure modifying device, such as a pump, can be controlled by a computer. In another embodiment, the computer used to control a pump can be accessed directly, wirelessly, or remotely through the internet, phone line, or a network. In yet another embodiment, the pressure modifying device, such as a pump, can be controlled by a user entering commands on a user interface connected to a computer. In a further embodiment, the pressure modifying device, such as a pump, can be controlled by a computer that is accessed through the internet, network, or phone line from commands entered on a user interface that is connected to an alternate computer. In a particular embodiment, dispensing cartridges can comprise a pressure modifying device, wherein the pressure modifying device draws fluid from a removable fluid cartridge into the dispensing cartridge and then forces the fluid from the dispensing cartridge into the fluid channel.

The disclosure also provides for a dual fluid cartridge system, which is comprised of a removable fluid cartridge and a self-contained pump dispensing cartridge that are fluidly in contact. In another embodiment a fluid delivery device of the disclosure comprises one or more dual fluid cartridge systems. In a particular embodiment, the disclosure provides that removable fluid cartridge and self-contained dispensing cartridge can be attached to one another by using a cartridge attachment projection that can be slideably inserted into a cartridge attachment depression. In a certain embodiment, the removable fluid cartridge comprises a cartridge attachment projection and the self-contained pump dispensing cartridge comprises a cartridge attachment depression. In alternate embodiment, the removable fluid cartridge comprises a cartridge attachment depression and the self-contained pump dispensing cartridge comprises a cartridge attachment projection. In a certain embodiment, the removable fluid cartridge of a dual fluid cartridge system is comprised of an ejection port and air relief port. In a further embodiment, the removable fluid cartridge of a dual fluid cartridge system is comprised of an ejection port and air relief port. In yet another embodiment, the self-contained pump dispensing cartridge is comprised of one or more deformable one-way valves, dispensing portal, and diaphragm, wherein the diaphragm can contract and expand by alternating a magnetic field. In yet another embodiment, the self-contained pump dispensing cartridge is comprised of one or more deformable one-way valves, a dispensing port, and a diaphragm, wherein the diaphragm can contract and expand by introducing or alternating a current of electricity. In a preferred embodiment, the deformable diaphragm is comprised of a metal, such as stainless steel.

In yet another embodiment, a fluid delivery device comprises: (a) a plurality of removable fluid cartridges arranged in series pre-filled, wherein the removable fluid cartridge comprises an ejection port, a machine readable indicator, and an injection port that is pressureably in contact with a pressure modifying device; (b) a detector for identifying a machine readable indicator and then outputting information from the machine readable indicator to a computer with attached user interface, such as a touchscreen; (c) a plurality of fluid cartridge adapters connected in series and in fluidly contact with a fluid channel, wherein the fluid cartridge adapters are dimensioned so as to receive an ejection port of a removable fluid cartridge; (d) a pressure modifying device, such as a pump, connected with air tubing to an injection port of one or more removable fluid cartridges so as to inject air into the removable fluid cartridges to force fluid out the ejection port of the cartridges; a dispensing tank comprising a supply of fluid that is fluidly in contact with the fluid channel, so that fluid from the dispensing tank can be used to advance fluid in the fluid channel to an exit portal; (e) an exit portal comprising tubing wherein one end of tubing is in contact with the fluid channel; (f) and a user interface, such as a touchscreen, wherein a user can enter commands in the user interface to control the operation of a pressure modifying device, such as pump, so as to control the amount, and timing of when fluid is released from removable fluid cartridge, fluid channel, and/or exit portal.

In a further embodiment, the removable fluid cartridge comprises a continuous tamper-proof seal which must be first removed before a removable fluid cartridge can be used. In a further embodiment, the removable fluid cartridge may be reused if the tamper-proof seal is not broken and not previously reused. In a certain embodiment, the removable fluid cartridge is comprised of an inner lining of glass, and an outer lining of any material. In another embodiment, the machine readable code on a removable fluid cartridge is an optical representation of data, such as a bar code, that can be detected and read by a detector, such as bar code reader. In yet another embodiment, the removable fluid cartridge comprises a plurality of fluid doses that can be delivered as a single unit dose and/or as a dose that is administered continuously or periodically. In a certain embodiment, the fluid in a removable fluid cartridge can be accessed a plurality of times, until the cartridge is empty. In alternate embodiment, the removable fluid cartridge is a single-use container of fluid to be disposed of or recycled after one use. In a particular embodiment, the removable fluid cartridge further comprises a lighted display, wherein the lighted display indicates the status of the cartridge, including pending user-controlled commands, accessing fluid, and/or delivering fluid. In another embodiment, the ejection port of the removable fluid cartridge can be used to inject fluid into the cartridge. In a further embodiment, the removable fluid cartridge comprises a shaped injection port, so that the injection port can receive a nozzle that is pressureably connected with a pressure modifying device. In a certain embodiment, a fluid delivery device of the disclosure further comprises one or more removable fluid cartridges. In yet a further embodiment, the fluid delivery comprising one or more removable fluid cartridges further comprises one or more devices to hold the cartridges in place once the cartridges are inserted into the fluid delivery device. In a particular embodiment, the fluid delivery device contains a lock or code, so that one or more removable fluid cartridges cannot be removed unless the lock is opened with a key, or an access code that must be entered. In a certain embodiment, the fluid from a removable fluid cartridge is delivered in pre-determined or provider-specified doses when activated by a user entering commands into a user interface, such as a touchscreen.

In a particular embodiment, the machine readable code is located on one face of the removable fluid cartridge. In another embodiment, the machine readable code is a microchip comprising a printed circuit board, and radio frequency identifier. In a further embodiment, the microchip can communicate with a detector or a user interface, such as a touchscreen, either directly by electrical contacts or wirelessly. In another embodiment, the microchip communicates identifying features about the removable fluid cartridge and the fluid contained therein to a user interface, such as a touchscreen, to visually present the features to a user. In yet another embodiment, the microchip provides information as to whether the cartridges have been previously used and status of sterility.

In a particular embodiment, the pressure modifying device comprises tubing that pressureably connects with an injection port of one or more removable fluid cartridges. In a particular embodiment, the tubing may further comprise injection port adapters that are adapted to make contact with the injection port of a removable fluid cartridge. In a further embodiment, the injection port adapters are sized so that the injection port adapters have a shape complementary to, and fit into, an injection port of a removable fluid cartridge. In yet a further embodiment, the injection port adapters can form a hermetic seal with the injection port of a removable fluid cartridge. In another embodiment, the injection port adapter is mobile relative to a removable fluid cartridge that is being held in place. In a further embodiment, a detector is moveably connected to injection port adapter, so that the detector can read a machine readable indicator on removable fluid cartridge as the injection port adapter is moved from one removable fluid cartridge to another. In yet a further embodiment, the pressure modifying device can exert either positive or negative air pressure to the fluid in a fluid removable cartridge through the injection port. In a certain embodiment, the pressure modifying device can exert positive air pressure to the fluid in a fluid removable cartridge through the injection port. In a further embodiment, the amount of fluid released from a removable fluid cartridge correlates to the amount of air pressure introduced by the pressure modifying device. In yet a further embodiment, the pressure modifying device modifies the pressure of a dispensing tank, so that the dispensing tank releases a fluid bolus to the fluid channel and/or exit portal. In another embodiment, the pressure modifying device exerts positive pressure of a dispensing tank, so that the dispensing tank releases a fluid bolus to the fluid channel and/or exit portal. In another embodiment, the pressure modifying device modifies the pressure of a dispensing tank through tubing that is pressureably connected to the pressure modifying device and dispensing tank. In yet another embodiment, the pressure modifying device modifies the pressure of a dispensing tank through tubing that is pressureably connected to the pressure modifying device and dispensing tank, wherein the tubing is connected to the pressure modifying device, dispensing tank, fluid channel, and/or exit portal using luer lock connections. In further embodiment, the fluid from the dispensing tank can be used to flush air from the fluid channel and/or from the exit portal. In yet a further embodiment, after a fluid is released from one or more fluid cartridges, a pre-determined or user determined bolus of fluid can be released from the dispensing tank. In additional embodiment, the user can give a fluid bolus or continuous infusion of fluid from a dispensing tank by entering commands in a user interface that is connected to a pressure modifying device that is pressureably connected to the dispensing tank. In a certain embodiment the exit portal comprising tubing further comprises an in line pressure exerting device, such as peristaltic pump. In another embodiment, the fluid channel and exit portal comprising tubing can be purged of air by advancing fluid through the length of the channel and exit portal tubing. In a further embodiment, the exit portal may further comprise a holding tank, wherein the holding tank can trap and prevent air from being advanced.

In a particular embodiment, a computer connected to the fluid delivery device of the disclosure comprises a touchscreen. In another embodiment, the touchscreen provides a multitouch display controlled by pressure-triggered fingertip input. In a further embodiment, a computer comprising a touchscreen is activated by entering a user's passcode and/or log-in information. In yet a further embodiment, a computer comprising a touchscreen contains one or more speakers which enunciates information provided on the machine readable indicator of one or more removable fluid cartridges after the removable fluid cartridges are inserted into a fluid delivery device disclosed herein. In another embodiment, a computer comprising a touchscreen is capable of connecting to other information storage systems such as an electronic medical record to access data such as patient's past medical history arranged according to name of condition and International Statistical Classification of Diseases and Related Health Problems, past surgical history, past anesthetic history, allergies, current medications, family history, social history, physical examination, and laboratories to feed into the fluid delivery device. In a further embodiment, a computer comprising a touchscreen can be used to cross reference data such as patient's past medical history arranged according to International Statistical Classification of Diseases and Related Health Problems, allergies, or medical history to prevent the delivery of contraindicated medications. In yet a further embodiment, a computer comprising a touchscreen is capable of sending warnings via the touchscreen before delivering fluids from a fluid delivery device disclosed herein, which may be contraindicated according to data supplied by information processing systems. In a particular embodiment, a computer comprising a touchscreen is capable of sending warnings via the touchscreen based on information gathered by information processing systems such as abnormal blood pressure, heart rate, breathing patterns, and oxygen saturation. In another embodiment, a computer comprising a touchscreen is capable of calling up pre-programmed algorithms and making recommendations of possible fluid dosages to address adverse clinical situation such as bradycardia, tachycardia, hypotension, hypertension, apnea, tachypnea, or desaturation. In yet another, a computer comprising a touchscreen is capable of calculating fluid dosages based on information supplied to the touchscreen such as weight and ideal body weight. In a certain embodiment, a computer comprising a touchscreen presents a range of possible fluid dosages based on weight. In another embodiment, a computer comprising a touchscreen monitors and records the amount of fluid delivered by a fluid delivery device disclosed herein. In yet another embodiment, a computer comprising a touchscreen can regulate the pressure of received by one or more removable fluid cartridges, wherein when a certain defined dosing limit has been reached the computer prevents pressure from reaching a removable fluid cartridge. In a particular embodiment, a computer comprising a touchscreen displays recorded or entered information about the fluid delivered by a fluid delivery device disclosed herein, such as medication name, drug class name, dosing guidelines, dosage, administration route, volume, expiration date, lot number, contraindications, adverse reactions, risk factors, special instructions, warnings, interactions, and monitoring parameters. In a further embodiment, a computer comprising a touchscreen notifies a user of fluid dosages out of range of guidelines such as weight, blood pressure, and overbreathing the ventilator. In yet a further embodiment, a computer comprising a touchscreen is capable of documenting information into information processing systems such as name of medication, concentration of medication, volume of medication, dosage of medication, route of medication administration, location of medication administration, duration of medication administration, method of medication administration, provider's initials, date of medication delivery, time of medication delivery, and medication expiration date. In a particular embodiment, a computer comprising a touchscreen controls a fluid delivery device disclosed herein so that the fluid delivery device administers a precise quantity of fluid based on volume/time (milligram/hour, milligram/minute, microgram/hour, microgram/minute, units/hour, units/minute); and/or dose/weight/time (microgram/kilogram/hour, microgram/kilogram/minute, milligram/kilogram/hour, milligram/kilogram/minute, units/kilogram/hour). In another embodiment, a computer comprising a touchscreen displays confirmation of impending delivery of fluid from a fluid delivery device disclosed herein to be canceled by a user entering a command into the touchscreen. In yet another embodiment, a computer comprising a touchscreen provides a timer for reminding the user to redose fluids or schedule fluids to be given in the future from a delivery device disclosed herein.

A method for controlling use of the device, comprising: (1) prompting a user to enter information about personnel and patient information; (2) detecting a machined readable indicator on the surface of the removable fluid cartridge by a detector when the cartridge is inserted into the device; (3) outputting information from the detector to an attached computer about the information provided by the machine readable indicator; (4) using an algorithm that is programmed into the computer to calculate a proper dose for administering to the patient based on the information outputted to the computer by detector and the user inputted information about the patient; and (5) administering the calculated dose by activating a motor to apply pressure to the removable fluid cartridge so as to force fluid from the removable fluid cartridge until the calculated dosage is achieved.

DETAILED DESCRIPTION

Figure 1:
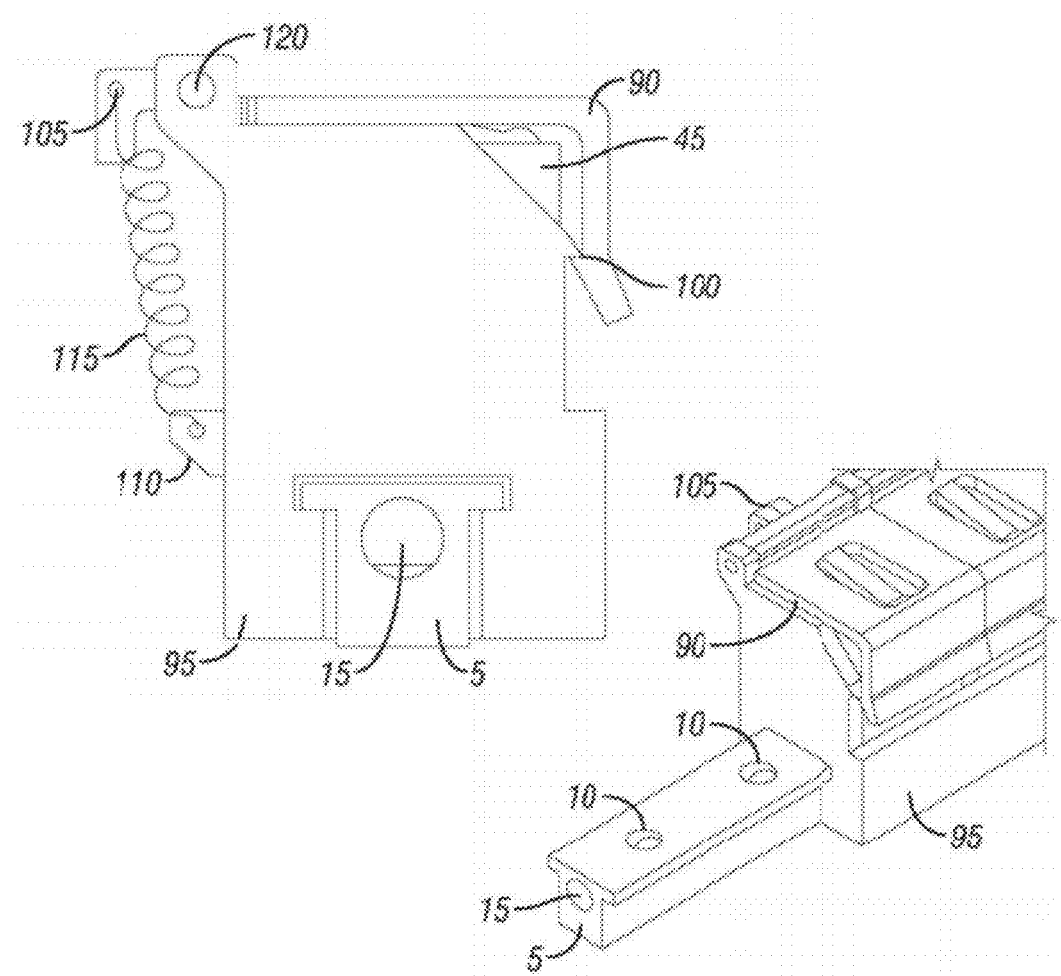
FIG. 1 is a side view and top-down angled view of a fluid delivery device showing certain features, such as an elongate member that is partially slid into a structural housing, and cover mechanisms to keep a cover open or closed over a removable fluid cartridge.

As used herein and in the appended claims, the singular forms "a," "and," and "the" include plural referents unless the context clearly dictates otherwise. Thus, for example, reference to "a liquid" includes a plurality of such liquids and reference to "the pump" includes reference to one or more pumps known to those skilled in the art, and so forth.

Unless defined otherwise, all technical and scientific terms used herein have the same meaning as commonly understood to one of ordinary skill in the art to which this disclosure belongs. Although many methods and mechanical components are similar or equivalent to those described herein and can be used in the practice of the disclosed methods and manufacture of the disclosed device, the exemplary methods and embodiments are now described.

Also, the use of "or" means "and/or" unless stated otherwise. Similarly, "comprise," "comprises," "comprising" "include," "includes," "including," "have," "haves," and "having" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

"Fluid" or "fluids" as used herein refer to liquids and gases.

"Liquids" as used herein refer to a form of matter with a definite volume but no fixed shape. It should be understood that "liquids" refer to all manner of liquids, such as syrups, solutions, mixtures, chemicals in a liquid state, oils, solvents, suspensions, and any combination of the foregoing.

"Cartridge" as used herein refers to any container capable of holding a reservoir of fluid. A specific, but not limiting example of a "cartridge" used herein, is a syringe. A "cartridge" may further comprise one or more ports, valves, labels, vents and machine readable indicators.

"Diaphragm" as used herein refers to a dispensing chamber that is comprised of material that has some portion of which that can flex inwards or outwards, such that the dispensing chamber is reduced in volume when a portion of the chamber is forced inwards and is expanded in volume when a portion of the chamber is pull outwards.

"Adapter" as used herein refers to a structural feature that is adapted to receive another structural feature. Typically, an adapter is hollow and allows the transmission of fluids. An adapter can be comprised of any material and any combination of materials. Moreover, an adapter can be comprised of multiple parts.

"Fluid cartridge adapter" as used herein refers to a structure that is adapted to receive a fluid from a cartridge or a tank. Typically, a fluid cartridge adapter is hollow and is fluidly in contact with a fluid channel. Generally, a fluid cartridge adapter can be bored hole in an elongate member, or can be a raised structure that is attached to an elongate member, wherein the attachment may be reversible or irreversible. A fluid cartridge adapter can be comprised of multiple parts.

"Elongate member" as used herein refers to a structure that has definable length, width, and height, which can be further comprised of a fluid channel and one or more fluid cartridge adapters. An elongate member can have a uniform shape along the entire length of the member or can have portions that are not uniform. For example the elongate member may have one or more projections, such as tips or nozzles, where a fluid cartridge adapter can then be attached to. An elongate member can be comprised of any material.

"Fluid channel" as used herein refers to an elongated structure comprising a first end and a second end capable of receiving fluid from fluid sources that are fluidly in contact with one or more adapters. A fluid channel also allows for the passage of fluid along the entire length of the channel. A fluid channel can be comprised of any material, and can have any dimension, so long as fluid can be transmitted along the length of the structure. A fluid channel may be open at the first end and closed at the second end, or vice versa. Alternatively, a fluid channel may be open at both the first and second ends.

"Injection Port" refers to a small hole on a face of a removable fluid cartridge where pressure can be exerted on fluid within the cartridge, so as to force liquid out the ejection port of the cartridge. In a certain embodiment, an injection port will be an open hole so as fluid within the cartridge is freely accessible to a pressure modifying device. In an alternate embodiment, an injection port will be hole that is covered with a pierceable material, such as film or foil, which must be pierced with a solid object, such as with a needle, before introducing pressure.

"Ejection Port" refers to a small hole on a face of a removable fluid cartridge where liquid can exit from the cartridge when positive or negative pressure is applied to the liquid in the cartridge. An ejection port may further comprise a valve. An ejection port may further comprise a removable protective covering to indicate tampering and prevent leakage.

"Pierceable Port" refers to a hole on a removable fluid cartridge that is covered with a pierceable material, such as film or foil that can be pierced with a solid object, such as with a needle. A pierceable port can be used to introduce gas, liquid or solids to the liquid inside the cartridge.

"User Interface" refers to a device that can be used with a machine, such as a computer, so that a user can interact with a machine. Examples of user interfaces, include, but are not limited to, touchscreens, mouse, keyboard, light pens, and key pads. A user interface may be directly connected to the machine, such as by a cable; connected wirelessly, such as by blue tooth, router, or modem; or remotely over a network, such as through a LAN network or through the internet.

"Information storage devices" for the purposes of this disclosure refers to device that can store and may also retrieve information. Examples of information storage devices for this disclosure include: hard drives, tapes, flash drives, computers, and servers. An information storage device may be directly connected to a machine, like a computer, by a cable or plug; connected wirelessly, such as by blue tooth, router, or modem; or remotely over a network, such as through a LAN network or through the internet.

"Pressure modifying device" for the purposes of this invention refers to a device capable of either introducing positive pressure on a liquid that is enclosed in a defined spaced, introducing negative pressure on a liquid that is enclosed in a defined spaced, or able to alternate between positive and negative pressure on a liquid that is enclosed in defined space. A pressure modifying device would include, but is not limited to, air compressors, pressurized tanks of gas, house vacuum and air sources, pumps, and vacuums. A pressure modifying device may introduce positive pressure, negative pressure, or alternate between positive and negative pressure by either introducing or withdrawing air/gases; introducing or withdrawing liquids; compressing liquids by physical means, such as a pushing down on a syringe plunger; expanding liquids by physical means, such as pulling on syringe plunger; or a combination thereof.

"Pressureably" as it relates to connections, refers to the ability for one or more structural components to be connected so that when pressure is modified in one component it affects the pressure in another component. Examples of pressureably connected could be by displacement through a physical connection, or by providing tubing, piping, etc. to allow the movement of gases, fluids, or a combination thereof.

"Slideably" refers to two or more structural components that can be connected or in contact with each other by sliding two or more complementary portions of the structural components together.

"Hingeably" refers to two structural components that are connected to each other so that one part stays fixed while the other structural component can move in an angle from 0 up to 180 degrees.

"Machine readable indicator" refers to any identifying visual mark, such as a QR code, or integrated circuit, such as microchip, that can be recognized by a detector, and wherein the detector can then output information related to the machine readable indicator to an alternate device, such as a computer. Examples of machine readable indicators, include, but are not limited to, any optical machine-readable representation of data, microchip, and transmitter.

"Detector" refers to any machine capable of detecting and identifying a machine readable indicator. A detector can include, but is not limited to, receivers, scanners, cameras, and readers.

All publications mentioned herein are incorporated herein by reference in full for the purpose of describing and disclosing the methodologies, which are described in the publications, which might be used in connection with the description herein. However, with respect to any similar or identical terms found in both the incorporated publications or references and those expressly put forth or defined in this application, then those terms definitions or meanings expressly put forth in this application shall control in all respects. The publications discussed above and throughout the text are provided solely for their disclosure prior to the filing date of the present application. Nothing herein is to be construed as an admission that the inventors are not entitled to antedate such disclosure by virtue of prior disclosure.

While throughout this disclosure specific applications have been highlighted, such as administering therapeutic agents to patients, it should be understood that the drug delivery device disclosed herein can be applied to any application which would require and/or benefit from having a device that can administer a metered volume of fluid. Any number of fields can be envision using such a device, including, but not limited to, general medicine, veterinary, scientific, industrial, residential, and commercial.

More specifically, the disclosure provides for a fluid delivery device that can accept a plurality of pre-filled removable fluid cartridges, wherein the device can then dispense liquid from one or more of these cartridges in a controlled manner by using a pressure modifying device, such as a pump. Moreover, a fluid delivery device disclosed herein can detect when a fluid cartridge is inserted in the device, and identify the contents.

The fluid delivery device in particular embodiments can then provide this information about the contents of each removable fluid cartridge to a user by using a connected information storage device, such as a computer with an attached display. Additionally, the user in certain embodiments can control the amount of fluid is released by each cartridge by entering commands on a user interface, such as a touchscreen, that is connected to the computer in communication with a fluid delivery device disclosed herein. In additional embodiments, the fluid delivery device disclosed herein can be networked through a connected computer to additional information storage devices. Accordingly, the fluid delivery device disclosed herein can relay information to a user about the fluid being administered and all other types of related or unrelated information. The computer which is connected to the fluid device disclosed herein may be through a physical connection, a wireless connection, or a remote connection. Likewise, additional information storage devices may be networked to the computer connected to the fluid delivery device disclosed herein by local area network, wireless network, or through remote networks, such as through the internet.

The accompanying drawings, which are incorporated into and constitute a part of this specification, illustrate one or more, non-limiting, embodiments of the disclosure and, together with the detailed description, serve to explain the principles and implementations of the disclosure. Like reference symbols in the various drawings indicate like elements.

An overview of an exemplary drug delivery device of the disclosure is presented in FIG. 1. An elongate member 5 is comprised of a fluid channel 15 and one or more fluid cartridge adapters 10, such that fluid channel 15 is fluidly connected to the fluid cartridge adapters 10 through the cartridge adapter channel 55. The fluid cartridge adapters 10 are adapted to receive fluid from removable fluid cartridges 45, such that fluid can be forced or drawn from the removable fluid cartridges 45 by using one or more pressure modifying devices 125 (not shown). The fluid can then travel down the fluid channel 15 an out an exit portal. In a certain embodiment, the fluid delivery device may further comprise a structural housing 95 that is dimensioned so as to contact an elongate member 5 in order to restrict the movement of the elongate member and to provide overall stability to the device. In another embodiment, the structural housing 95 may further comprise a cover 90, in order to restrict the movement of removable fluid cartridges 45. In an additional embodiment, a rearward disposed hinge 120 pivotally connects cover 90 to the structural housing 95. In a certain embodiment, the front of the cover 90 is formed as a lip, latch, or flange 100 that extends essentially at a 90° angle downwardly from the planar top of the cover. In yet another embodiment, cover 90 further comprises a cover projection 105 that can be connected to a structural housing projection 110 of the structural housing 95 by using a spring 115, such that spring 115 provides tension so that the cover 90 will remain in an opened upright position when lip, flange, or latch 100 is disengaged from the peripheral edge of structural housing 95.

Figure 2:
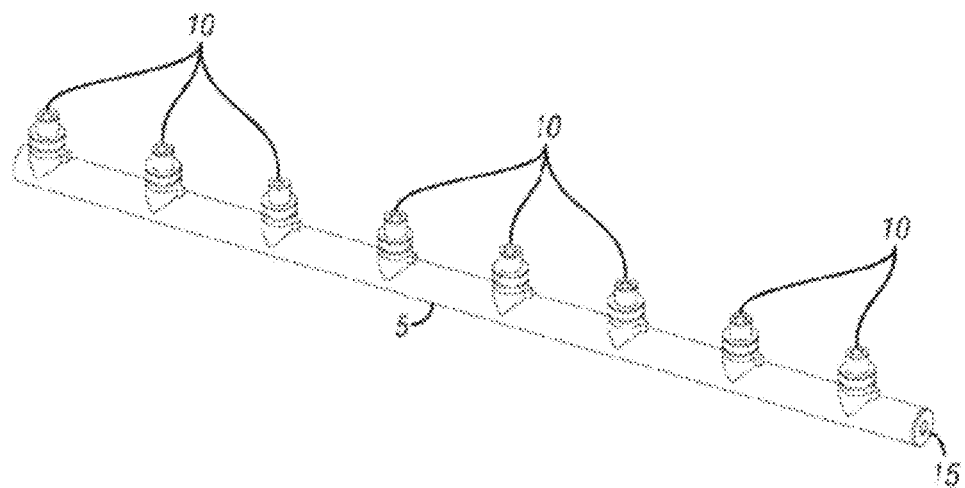
FIG. 2 is a close-up view of a tubed-shaped elongate member with a plurality of raised fluid cartridge adapters to allow fluid to access a fluid channel within the elongate member.
Figure 3:
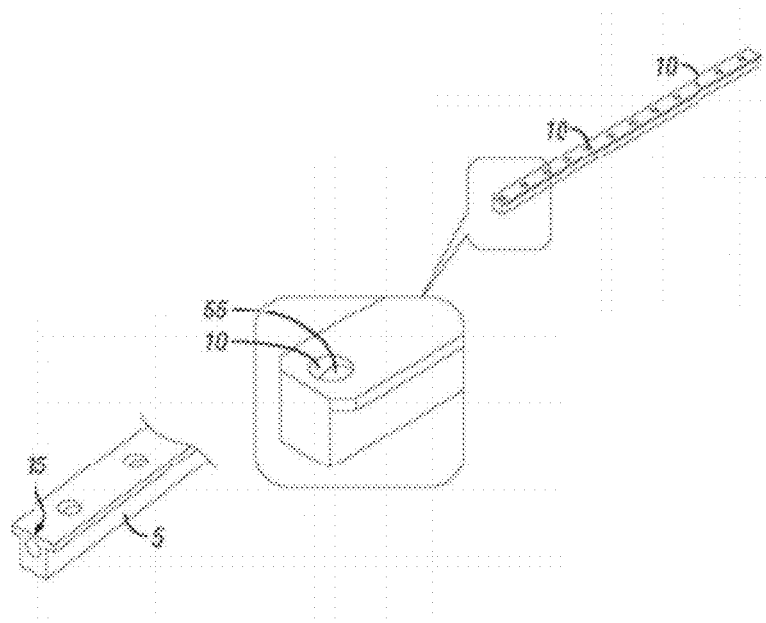
FIG. 3 is a close-up view of a T-shaped elongate member with a plurality of bored fluid cartridge adapters to allow fluid to access a fluid channel within the elongate member.

Turning now to specific structural features of the fluid delivery device of the disclosure, FIG. 2 and FIG. 3 provide a cut away view of an elongate member 5 that is comprised of a fluid channel 15, and a plurality of fluid cartridge adapters 10 comprising cartridge adapter channels 55. Elongate member 5 has a first end and a second end. Elongate member 5 may be comprised of any material or any combination of materials. In a certain embodiment the elongate member 5 is comprised of plastic. In a further embodiment the elongate member 5 is comprised of rubber. In yet another embodiment, the elongate member 5 is comprised of material that is inert to fluids. In yet a further embodiment, the elongate member 5 is comprised of metal. Generally, elongate member 5 should be of a sufficient length so that it can potentially accommodate one or more removable fluid cartridges. In a particular embodiment, elongate member 5 is from 2 to 36 inches in length. In another embodiment, elongate member 5 is from 2 to 24 inches in length. In yet another embodiment, elongate member 5 is from 6 to 24 inches in length. In a further embodiment, elongate member 5 is from 10 to 24 inches in length. Elongate member 5 comprises at least 1 wall defining an enclosed space or tube. Moreover, the width of elongate member 5 can vary. The first and second end of elongate member 5 may have relatively the same dimensions or alternatively the ends may have different dimensions.

While the Figures in this application present an elongate member 5, as being substantially tube-shaped or T-shaped, the disclosure provides for elongate member 5 having substantially a non-tubed shape or a non-T shape. Any shape for elongate member 5 is acceptable, so long as the elongate member can further comprise a fluid channel 15 and one or more fluid cartridge adapters 10. In a certain embodiment, elongate member 5 has a substantially flat lower wall so as to provide stability when elongate member 5 is placed on a flat surface. However, elongate member 5 may be in contact with a structural housing 95, such that structural housing 95 can provide needed structural stability. In such a case, elongate member 5 can have a bottom face that is substantially not flat or have portions that are substantially flat and not flat.

Fluid channel 15 can be any shape. Fluid channel 15 can be centrally disposed in elongate member 5 or alternatively be disposed off-center in elongate member 5. The diameter or cross section of fluid channel 15 can be generally sized to fit the needs of a particular application. For example, for industrial applications the fluid channel may need to be of a sufficient size to allow a large volume of one or more fluids to pass down the channel and out the exit portal. Alternatively, for medical applications the fluid channel may require a smaller diameter to account for a low volume of fluid passing into the fluid channel. Fluid channel 15 has at least one opening present in one end of elongate member 5 that is connected to an exit portal. Fluid channel 15, however, in a certain embodiment, can allow for openings being present in both ends of elongate member 5. This second opening could facilitate attaching one or more pressure modifying devices, such as pumps, compressors, or gas cylinders in order to push fluids remaining in fluid channel 15 out into the exit portal. This second opening could be also used to attach a reservoir of wash solution so that fluid channel 15 can be cleaned of any residual fluid originating from one or more removable fluid cartridges 45. The second opening could also be fluidly connected to a dispensing tank 97.

In another embodiment, fluid channel 15 can be comprised of one or more tubes that are fluidly connected to one or more removable fluid cartridges 45. In a particular embodiment, each fluid cartridge adapter 10 comprises individual tubing that runs down the length of fluid channel 15 and out to the exit portal. Examples of such tubing, including surgical tubing, or pharmaceutical grade tubing. Moreover, the tubing should have a relatively small diameter so that a plurality of tubing can fit within fluid channel 15. The plurality of tubing may then be combined into a single tube in the exit portal, if so needed, or alternatively remain separate.

Figure 4:
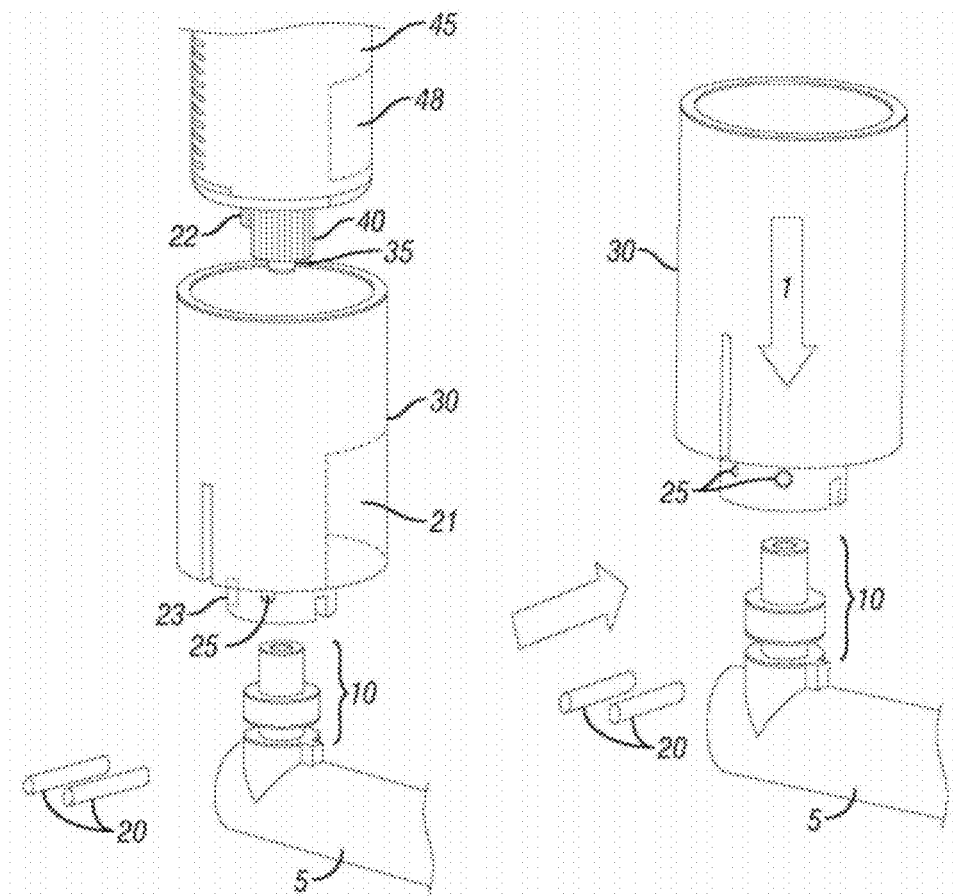
FIG. 4 is multiple front views of an exemplary process to attach a fluid cartridge holder to fluid cartridge adapter.

FIG. 4 presents a particular embodiment of the disclosure, by showing a close-up view and exemplary process of attaching one or more fluid cartridge holders 30 to one or more fluid cartridge adapters 10. An elongate member 5 comprising an internal fluid channel 15 (not shown) and one fluid cartridge adapter 10 is presented. In a certain embodiment, a fluid cartridge holder 30 can be attached to fluid cartridge adapter 10. Fluid cartridge holder 30 may be comprised of any material or any combination of materials. In a certain embodiment fluid cartridge holder 30 is comprised of plastic. In a further embodiment fluid cartridge holder 30 is comprised of metal. In yet a further embodiment, fluid cartridge holder 30 is comprised of metal and plastic. The fluid cartridge holder 30 can be of any shape, as long as a portion of a removable fluid cartridge 45 can be placed inside the fluid cartridge holder 30. In an alternative embodiment, the structural housing 95 can be dimensioned to receive a removable fluid cartridge 45. In yet another alternative embodiment, the disclosure provides that the fluid delivery device does not comprise a fluid cartridge holder 30.

In a certain embodiment, a fluid cartridge holder 30 is dimensioned so that it can be attached to fluid cartridge adapter 10. In another embodiment, a fluid cartridge holder 30 is dimensioned so that it can be attached to structural housing 95. In yet another embodiment, a fluid cartridge holder 30 is dimensioned so that it can be attached to elongate member 5. The attachable fluid cartridge holder can be attached to a fluid cartridge adapter 10, structural housing 95, and/or elongate member 5, by any manner known in the art. In a certain embodiment, the disclosure provides that the fluid cartridge holder 30 can be irreversibly attached to a fluid cartridge adapter 10, structural housing 95, and/or elongate member 5. Examples of irreversible attachment include, but are not limited to, welding, molding, cementing, gluing, and riveting. In an alternative embodiment, the disclosure provides that a fluid cartridge holder 30 can be reversibly attached to a fluid cartridge adapter 10, structural housing 95, and/or elongate member 5. Examples of reversible attachment include, but are not limited to, locking pins; threaded connections, such as being able to screw a holder onto an adapter; screws; lock and key type connections; retaining rings; and clasps. An exemplary process of attaching a fluid cartridge holder 30 to a fluid cartridge adapter 10 by using locking pins 20 fitting into complementary locking pin holes 25 on a fluid cartridge holder 30 is presented. First, a fluid cartridge holder 30 is placed on a fluid cartridge adapter 10, and then locking pins 20 are then inserted into the complementary locking pin holes 25 of a fluid cartridge holder 30. In another embodiment, a fluid cartridge holder 30 is attached to a structural housing 95 (not shown) by a fastening means, in such a case fluid cartridge holder 30 may or may not be further attached to fluid cartridge adapter 10. Examples of fastening means, include, but are not limited to, using fasteners, using fastening agents, or welding. In a particular embodiment a fluid cartridge holder 30 is attached to structural housing 95 and not attached to a fluid cartridge adapter 10. In a further embodiment, a fluid cartridge holder 30 is attached to structural housing 95 and attached to a fluid cartridge adapter 10.

Generally, the fluid cartridge adapter 10 is adapted to receive a removable fluid cartridge 45 even when a fluid cartridge holder 30 is attached to a fluid cartridge adapter 10. In a certain embodiment, a fluid cartridge adapter 10 comprises a male type receptor that can fit into a matching female type receptor on a removable fluid cartridge 45. In an alternate embodiment, a removable fluid cartridge 45 comprises a male type nozzle 35 that can fit into a matching female type receptor on a fluid cartridge adapter 10. In a further embodiment, a removable fluid cartridge 45 comprising a male type nozzle 35 further comprises a sleeve 40, such that sleeve 40 can fit snugly around post 60 (not labeled) of a fluid cartridge adapter 10. In yet a further embodiment, sleeve 40 may further comprise a notch projection 22 that can slideably insert into a matching notch depression 23 on a fluid cartridge holder. In a further embodiment, the notch depression 23 on a fluid cartridge holder 30 is funnel shaped so that notch projection 22 is guided to the correct orientation by slideably inserting into notch depression 23.

In a particular embodiment, removable fluid cartridge 45 may further comprise machine readable code 48, so that once removable fluid cartridge 45 is slideably inserted into a fluid cartridge holder 30, machine readable code 48 can be read by detector 36 (not shown) through the window 21 on fluid cartridge holder 30. In a further embodiment, machine readable code 48 is orientated to be contiguous with window 21 by slideably inserting removable cartridge 45 into cartridge holder 30 so that notch projection 22 is guided into the matching notch depression 23.

Figure 5:
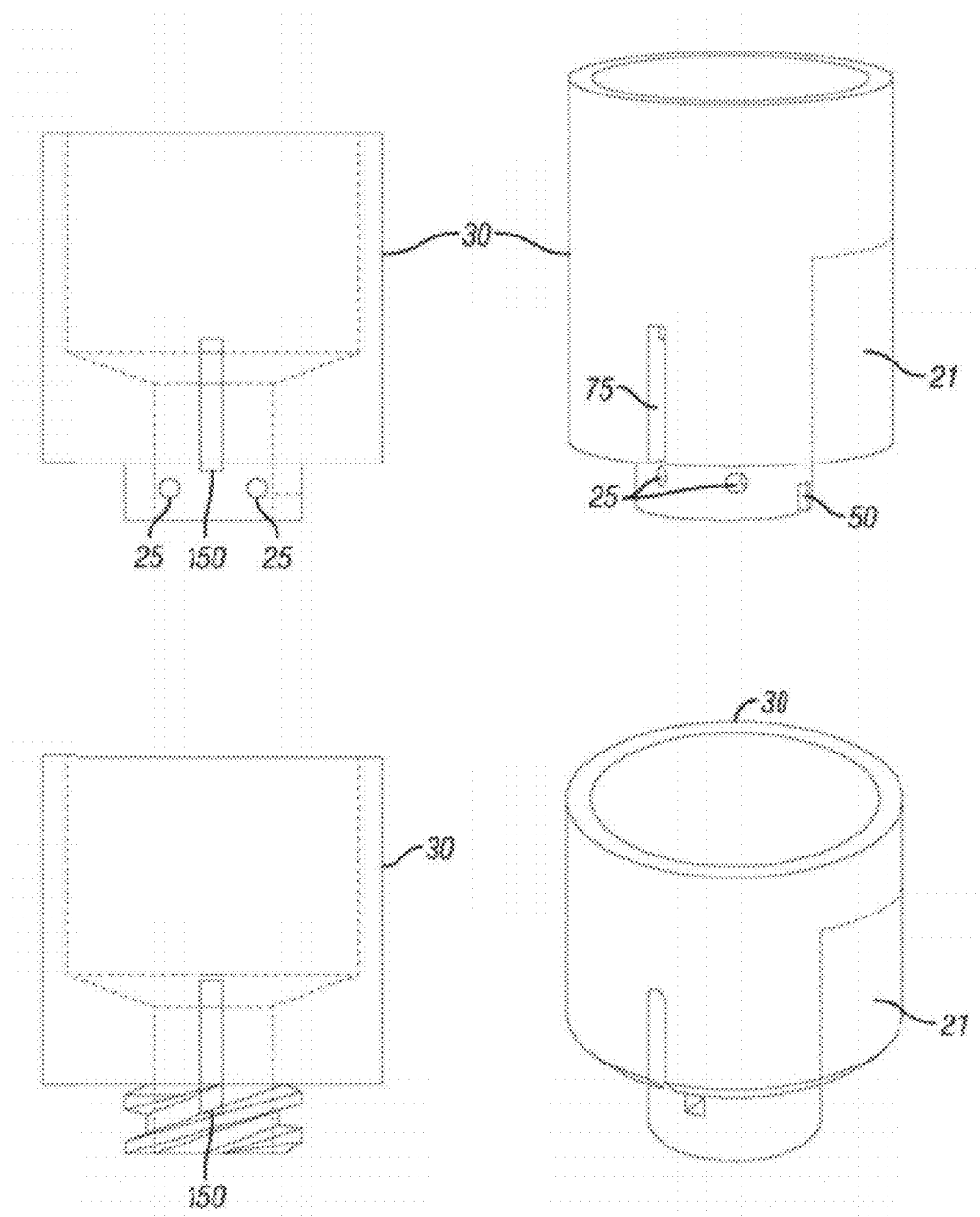
FIG. 5 is a multi-view of a fluid cartridge holder.

FIG. 5 presents a particular embodiment of the disclosure, by showing a variety of views of a fluid cartridge holder 30 of the disclosure. In a particular embodiment, a fluid cartridge holder 30 may comprises one or more locking pin holes 25, so that one or more locking pins 20 (not shown) can be inserted into the locking pin holes 25. In an alternate embodiment, fluid cartridge holder 30 contains screw threads so that it can be screwed into matching threads of a fluid cartridge adapter 10 (not shown). In a further embodiment, a fluid cartridge holder 30 that is screwed into a fluid cartridge adapter 10 (not shown) forms a hermetic seal. In another embodiment, a fluid cartridge holder 30 may comprise notch 50, wherein notch 50 can fit into a notched projection 70 (not shown) of a fluid cartridge adapter 10. In a further embodiment, a fluid cartridge holder 30 may comprise slit 75, so that a user could visibly inspect the fluid level of removable fluid cartridge 45, and/or allow a detector to identify a machine readable code being presented through slit 75. In another embodiment, a fluid cartridge holder 30 may comprise a valve 150, wherein valve 150 prevents fluid from entering the removable fluid cartridge 45 through ejection port 46 (not shown). In another embodiment, a fluid removable fluid cartridge 45 may comprise a valve 150, wherein valve 150 prevents fluid from entering the removable fluid cartridge 45 through ejection port 46 (not shown). In a certain embodiment, fluid cartridge 30 may further comprise window 21, so that label 38 (not shown), label 38 (not shown) further comprising machine readable code 48 (not shown), or a machine readable code 48 (not shown) can be visually seen by a user and/or can be identified by a detector 36, when a removable cartridge 45 is inserted into fluid cartridge holder 30.

Figure 6:
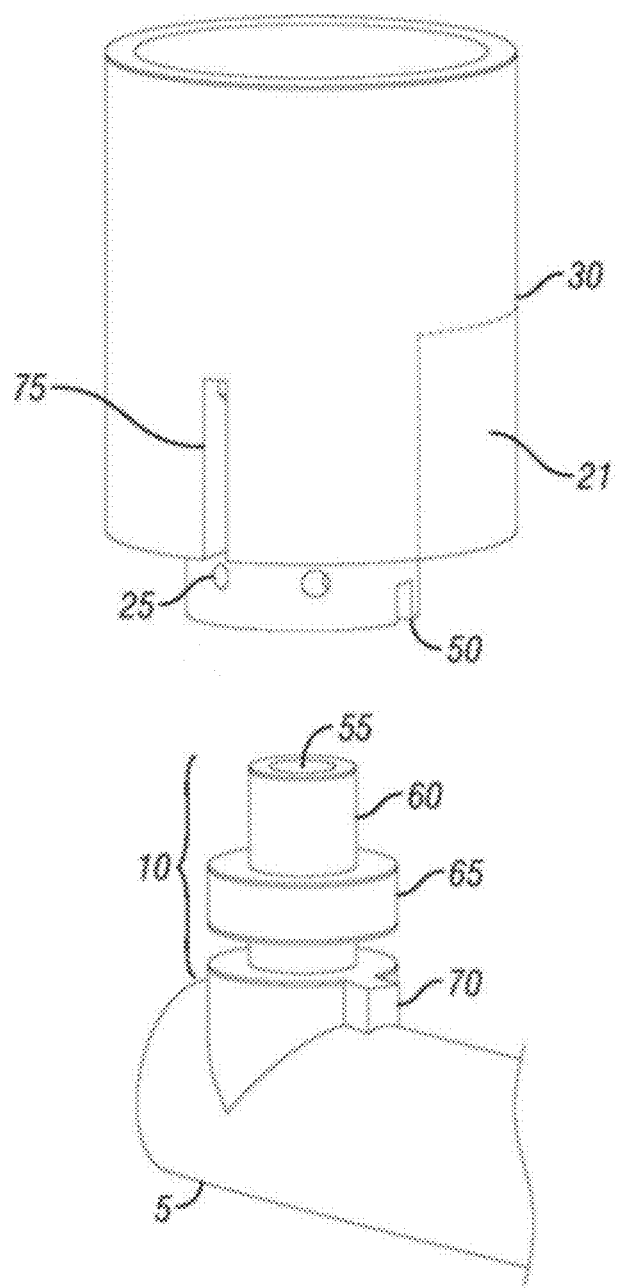
FIG. 6 is a close-up side view of a fluid cartridge adapter and a fluid cartridge holder.

FIG. 6 presents a close-up view of an exemplary a fluid cartridge adapter 10 of the disclosure. Also is shown is a close-up view, in another embodiment, of a fluid cartridge holder 30 of the disclosure. In a certain embodiment, a fluid cartridge holder 30 can comprise one or more locking pin holes 25, window 21, a slit 75, and/or a notch 50. In another embodiment, a fluid cartridge holder 30 comprising notch 50 can fit into a notched projection 70 on a fluid cartridge adapter 10, so that notched projection 70 fits into notch 50 to prevent rotation by a fluid cartridge holder 30 around a horizontal axis once attached to a fluid cartridge adapter 10, and/or so cartridge holder 30 is forced to assume only one orientation.

A fluid cartridge adapter 10 is fluidly connected to fluid channel through a cartridge adapter channel 55. Cartridge adapter channel 55 can be of any length and of any diameter, so long as fluid can flow from a removable fluid cartridge 45 and through cartridge adapter channel 55. In a certain embodiment, cartridge adapter channel 55 may further comprise a one way valve, so that fluid can only flow from a removable fluid cartridge into fluid channel 15. In another embodiment, cartridge adapter channel 55 may further comprise a one way valve so that once the valve is closed no fluid can flow from the removable fluid cartridge into a fluid channel. Such locking and one way valves can be either manually, magnetically, and/or electronically opened or closed. Moreover, the disclosure provides embodiments, for the opening or closing of such valves by entering user defined commands on a user interface that is connected to a computer, which is connected to a fluid delivery device disclosed herein.

A fluid cartridge adapter 10 can have any shape as long as the fluid cartridge adapter can receive fluid from a removable fluid cartridge 45. In a certain embodiment, a fluid cartridge adapter 10 is a hole in the elongate member 5 that is fluidly connected to fluid channel 15. A fluid cartridge adapter 10 may be comprised of any material or any combination of materials. In yet another embodiment, the cartridge adapter 10 is comprised of material that is inert to fluids. In a certain embodiment, a fluid cartridge adapter 10 is comprised of plastic. In a further embodiment, a fluid cartridge holder 10 is comprised of rubber. In yet a further embodiment, fluid cartridge holder 10 is comprised of metal. A fluid cartridge adapter 10 can be attached to an elongate member 5 by any means. In alternative embodiment, a fluid cartridge adapter 10 can be reversibly attached to an elongate member 5. For example, a threaded fluid cartridge adapter 10 can be screwed into a matching threaded elongate member 5. In a preferred embodiment, fluid cartridge adapter 10 can be fitted onto a raised hollow portion, such as a nozzle or tip, on elongate member 5. In another embodiment, a fluid cartridge adapter 10 is irreversibly attached to an elongate member 5. Examples of irreversible attachment include, but are not limited to, welding, molding, cementing, gluing, and riveting. In a particular embodiment, a fluid cartridge adapter 10 is comprised of one or more of the following: notch projection 70, locking ring 65, and post 60.

Figure 7:
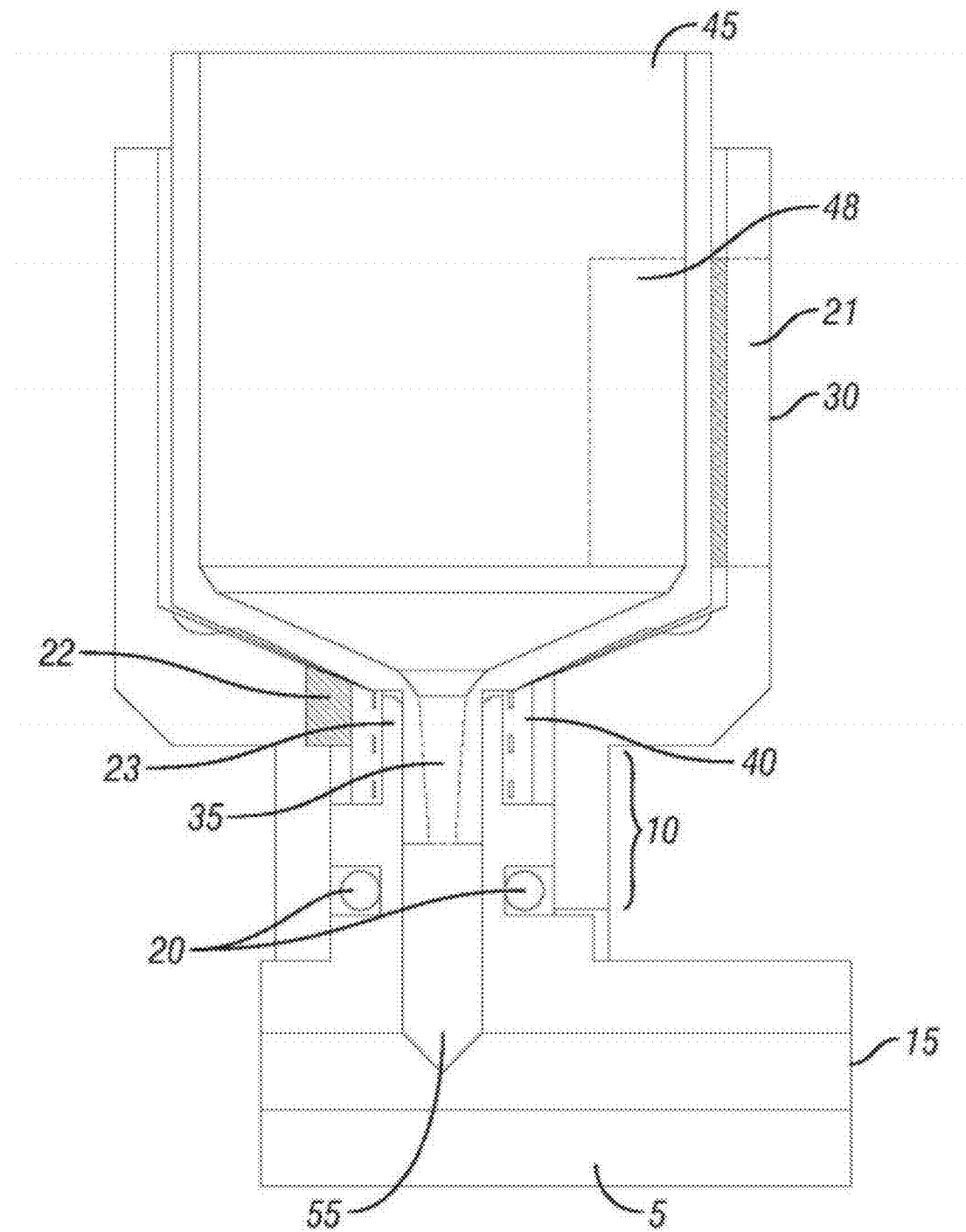
FIG. 7 is a cut-away front view of a fluid cartridge holder containing a removable fluid cartridge that is attached to a fluid cartridge adapter, and wherein the removable fluid cartridge is shown to be fluidly in contact with the fluid channel of an elongate member.

FIG. 7 presents an embodiment of the disclosure of a fluid cartridge holder 30 and a removable fluid cartridge 45 attached to a fluid cartridge adapter 10. The fluid cartridge adapter 10 is fluidly connected to a fluid channel 15, through a cartridge adapter channel 55. In a certain embodiment, notch 50 of the fluid cartridge holder 30 is operationally fitted into a notched projection 70 on the fluid cartridge adapter 10, so that fluid cartridge holder 30 can no longer rotate around a horizontal axis, and/or so cartridge holder 30 is forced to assume only one orientation. In another embodiment, locking pins 20 are operatively engaged in the complementary locking ring holes 25 of the fluid cartridge holder 30. In a further embodiment, locking ring 65 of the fluid cartridge adapter 10 prevents any substantial upward movement of the fluid cartridge holder 30. Fluid cartridge adapter 10 has been adapted to receive, in one embodiment, a male type nozzle 35 of the removable fluid cartridge 45. In another embodiment, sleeve 40 is operationally fitted on post 60 of the fluid cartridge adapter 10, so that the removable fluid cartridge 45 is securely fitted to fluid cartridge adapter 10. In additional embodiment, sleeve 40 sits evenly on the top of locking ring 65 so as to maintain a removable fluid cartridge 45 in a substantial upright position. In a certain embodiment, a nozzle 35 of a removable fluid cartridge 45 may further comprise a valve 150 (not shown), such that fluid can only flow from the removable fluid cartridge into the fluid channel, and not from the fluid channel into the removable fluid cartridge. Sleeve 40 may be comprised of any material, including, but not limited to, plastic, metal, nylon, and rubber. In a further embodiment, sleeve 40 may further comprise notch projection 22, which can slideably insert into a matching notch depression 23 on a removable fluid cartridge 30.

Figure 8:
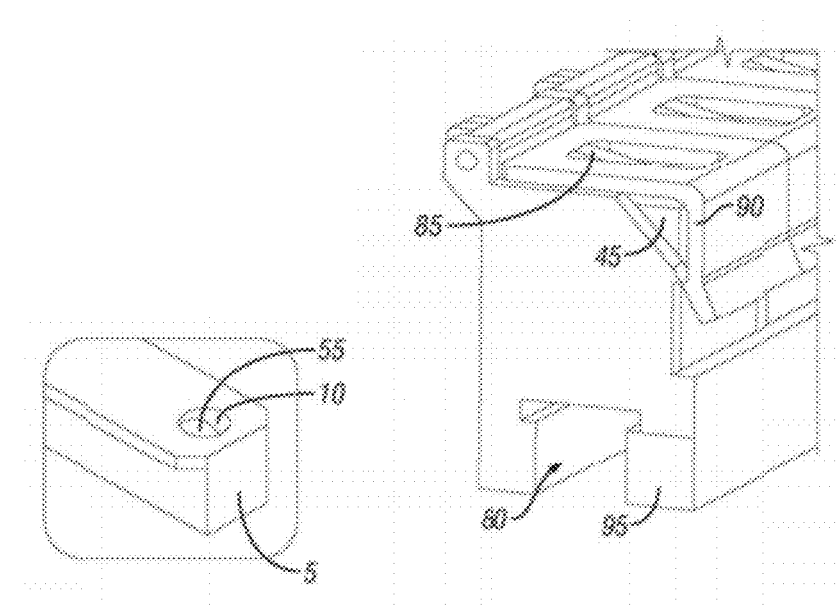
FIG. 8 is a close-up view and side angled view of a T-shaped elongate member with a bored fluid cartridge adapter, and a structural housing with a depression to specifically fit a T-shape elongate member, respectively.

FIG. 8 presents a close-up top down view of an elongate member 5 of the disclosure. Also is shown, is a side angle view of in a certain embodiment, structural housing 95 of the disclosure. The fluid cartridge adapter 10 through a cartridge adapter channel 55 is fluidly connected to a fluid channel 15 (not shown) of elongate member 5. In a certain embodiment, structural housing 95 contacts elongate member 5, so that structural housing 95 restricts elongate member 5's movement. In another embodiment, structural housing 95 makes at least one point of contact with elongate member 5. In yet another embodiment, structural housing 95 makes at least two points of contact with elongate member 5. In a further embodiment, structural housing 95 makes at least 3 points of contact with elongate member 5. In yet a further embodiment, structural housing 95 contacts elongate member 5 from the first end to the second end. In a particular embodiment, elongate member 5 is shaped so it fits into a matching elongate member depression 80 of a structural housing 95.

Structural housing 95 may be made from any material. In a particular embodiment, structural housing 95 is comprised of metal. In another embodiment, structural housing 95 is comprised of plastic. In yet another embodiment, structural housing 95 is comprised of metal and plastic. In a certain embodiment, structural housing 95 can provide support for one or more removable fluid cartridges 45, such that the structural housing 95 prevents the movement of one or more removable fluid cartridges 45 from a substantially upright position. In a further embodiment, structural housing 95 further comprises a cover 90, in order to restrict the movement of removable fluid cartridges 45. In a certain embodiment, the front of the cover 90 is formed as a lip, latch, or flange that extends essentially at a 90° angle downwardly from the planar top of the cover. The lip, latch, or flange of cover 90 is provided in another embodiment with a recessed edge 100 that can engage with the peripheral edges of the structural housing 95, so that when pushed down locks cover 90 in a closed position. In yet another embodiment, structural housing 95 comprising cover 90, further comprises a centrally located bendable flange 85, which is attached to the rear edge of the cover 90, so that bendable flange 85 applies pressure to the top of the removable fluid cartridge 45 once removable fluid cartridge 45 is attached to the fluid cartridge adapter 10 and cover 90 is closed. Bendable flange 85 allows cover 90 to snap open to an upright open position once the lip, flange, or latch from the cover 90 is lifted.

Figure 9:
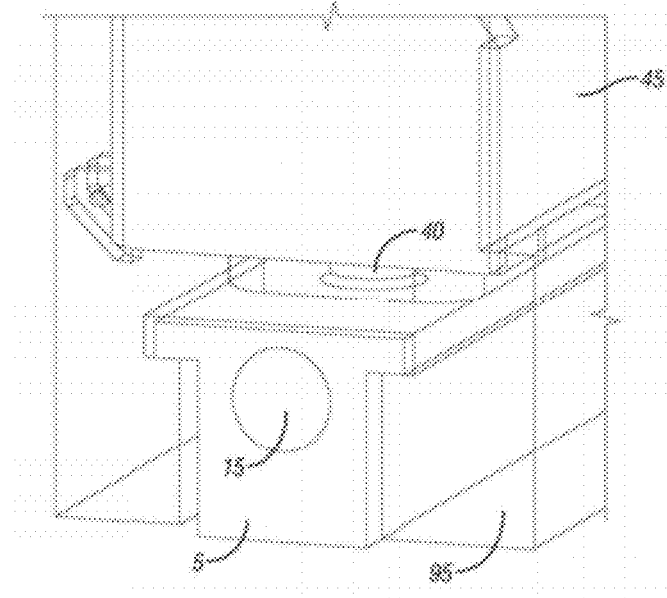
FIG. 9 is a close-up cross-sectional schematic view of a removable fluid cartridge fluidly in contact with a fluid channel of a T-shaped elongate member.

FIG. 9 provides a close up side angle view of an embodiment of the disclosure showing elongate member 5 in contact with structural housing 95. In a particular embodiment, elongate member 5 could be slideably inserted into a matching elongate member depression 80 of structural housing 95. Also is shown, is fluid cartridge adapter 10 in contact with the sleeve 40 of a removable fluid cartridge 45. In a further embodiment, sleeve 40 has a substantially flat lower surface so that it facilitates removable fluid cartridge 45 being maintained in a vertically upright position.

Figure 10:
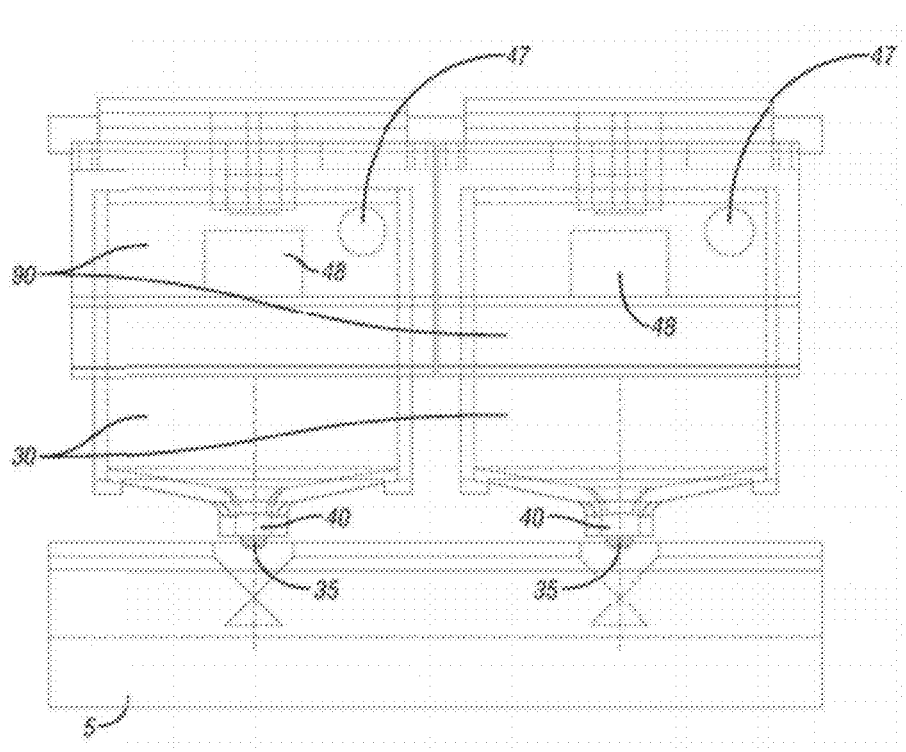
FIG. 10 is a cross-sectional schematic view of two removable fluid cartridges and two covers, wherein the removable fluid cartridges are shown to be fluidly in contact with a fluid channel of an elongate member.

FIG. 10 provides a cut away frontal view of one embodiment of the disclosure of showing two removable fluid cartridges 45 attached to an elongate member 5 through fluid cartridge adapters 10. Also is shown is cover 90 of a structural housing 95 in a closed position, with the removable fluid cartridges 45 outlined within. In another embodiment, the disclosure provides for a removable fluid cartridge 45 comprising one or more features selected from the group of: sleeve 40, a fluid ejection port 46 (not shown), an injection port 47, a label 38 (not shown), a machine readable indicator 48 (not shown), a valve 150 (not shown), and a piereceable port 39 (not shown). In yet a further embodiment, the disclosure provides for a removable fluid cartridge 45 comprising a fluid ejection port 46 (not shown), an injection port 47, a label 38 (not shown), one or more machine readable indicators 48, and a pierceable port 39 (not shown). In another embodiment, the disclosure provides for a removable fluid cartridge 45 that can be attached to a fluid cartridge adapter 10 of a device disclosed herein, wherein the attachment of the removable fluid cartridge 45 to a fluid cartridge adapter 10 forms a hermetic seal.

The disclosure provides for removable fluid cartridge 45 having an ejection port 46 (not shown) on one face of the removable fluid cartridge 45. In a certain embodiment, the ejection port 46 (not shown) is located at the bottom face of a fluid cartridge 45. In a further embodiment, a male type nozzle 35 further comprises an ejection port 46 (not shown). In another embodiment, the ejection port 46 (not shown) is covered with a removable security film to prevent leakage of the fluid contents and to indicate tampering. In an additional embodiment, the ejection port 46 (not shown) can further comprise a valve 150, so that fluid can flow out of the ejection port 46 (not shown), but not into ejection port 46 (not shown).

In a particular embodiment, the fluid drug delivery device can identify a removable fluid cartridge 45 by at least one, two or three methods. In a certain embodiment, a removable fluid cartridge 45 comprises one or more machine readable indicators 48 that comprises a microchip, such as a radio frequency identifier, that is identified by a detector 36 (not shown) once the removable fluid cartridge 45 is inserted into the device. In another embodiment, the device disclosed herein presents the contents of the removable fluid cartridge using the information provided by the machine readable indicator 48, such as a microchip, onto a user interface, such as a touch-screen. In yet another embodiment, the disclosure provides for a removable fluid cartridge 45 further comprising a one-piece label 38 (not shown) on one face of the removable fluid cartridge 45, wherein the label can provide information about the fluid inside a removable fluid cartridge 45, including, but not limited to, the name of fluid, concentration, volume, lot number, instructions, and expiration date. In an alternate embodiment, the label is not viewable when the removable fluid cartridge 45 is inserted into the fluid delivery device of the disclosure. In a particular embodiment, the label is viewable when the removable fluid cartridge 45 is inserted into the fluid delivery device of the disclosure. In a certain embodiment, the disclosure provides for a fluid delivery device comprising a label that further comprises a machine readable indicator 48. In another embodiment, the disclosure provides for a fluid delivery device comprising a label that does not further comprise a machine readable indicator 48. In a further embodiment, the disclosure provides for a removable fluid cartridge 45 that comprises one or more machine readable indicator 48 that is an optical machine-readable representation of data, such as linear bar codes, matrix barcodes, QR codes, Aztec codes, and ShotCodes. In yet a further embodiment, the disclosure provides for a fluid delivery device comprising a detector 36 (not shown) that can read one or more machine-readable indicators. In a certain embodiment, the detector 36 (not shown) is across from a machine readable indicator 48. In a further embodiment, the detector is attached to or part of a computer. Examples of detectors 36 include, but are not limited to, bar code readers, cameras, radio frequency receivers, scanners, or a combination thereof. In a certain embodiment, the disclosure provides for a fluid delivery device comprising a detector which can scan a bar code. In another embodiment, the disclosure provides for a fluid delivery device comprising a detector that can scan a bar code and is located across from a machine readable indicator 48.

Figure 11:
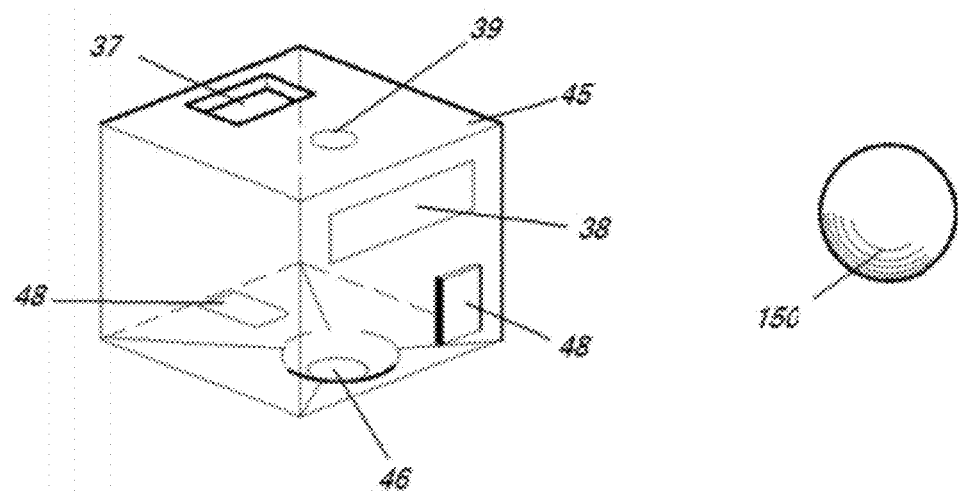
FIG. 11 is a front angle view of a removable fluid cartridge and of a ball shaped valve.

FIG. 11 presents a certain embodiment of the disclosure of a removable fluid cartridge 45 and valve 150. A removable fluid cartridge may comprise a label 38, wherein label 38 provides information related to the fluid inside the removable fluid cartridge 45. Examples of such information, include, but are not limited to, identifying the components of the solution, whether the fluid is sterile or not, providing concentrations of the components comprising the fluid, suggesting dosing parameters, providing the volume of fluid, providing proper storage and handling conditions, providing an expiration date, and providing the lot number and date of manufacturing. In yet another embodiment, label 38 may further comprise a machine indicator 48.

In a particular embodiment, the disclosure provides for removable fluid cartridge 45 further comprising a pierceable port 39. In a certain embodiment, the pierceable port 39 is located on one of the accessible faces of the removable fluid cartridge 45. Generally, the pierceable port 39 should be located so as to facilitate access to the fluid in the removable fluid cartridge 45 for the purposes of mixing, withdrawing, and or injecting a gas to the fluids inside. The pierceable port 39 is covered with a material, such as foil, plastic, or a membrane, that can be punctured by an solid object, such as a needle.

In another embodiment, the disclosure provides for a removable fluid cartridge 45 further comprising a bendable flange depression 37, wherein a portion of a bendable flange 85 (not shown) attached to cover 90 can insert into this depression 37 when cover 90 (not shown) is closed. Bendable flange depression 37 can be of any shape, so long as a portion of the bendable flange can fit into the depression.

In a particular embodiment, ejection port 46 may be adapted to receive a valve 150. In a certain embodiment, valve 150 is a one-way valve that allows fluid to leave a removable fluid cartridge 45 through an ejection port 46, but not allow fluid to enter through ejection port 46 into the removable fluid cartridge 45. In an alternate embodiment, valve 150 may be a rubberized steel ball, wherein the rubberized steel ball can fit tightly into an ejection port 46 that is adapted to receive a rubberized steel ball. In a further embodiment, the rubberized steel ball can be displaced from ejection port 46 with a valve displacing needle 171 (not shown).

In yet another embodiment, a removable fluid cartridge 45 may comprise one or more machine readable indicators 48 that can be detected by a detector 36 (not shown). In a certain embodiment, a removable fluid cartridge 45 may comprise two or more different machine readable indicators 48, such as a microchip and an optical representation of data, wherein each machine readable indicator can be read by the same detector 36 (not shown) or by different detectors 36 (not shown).

Figure 12:
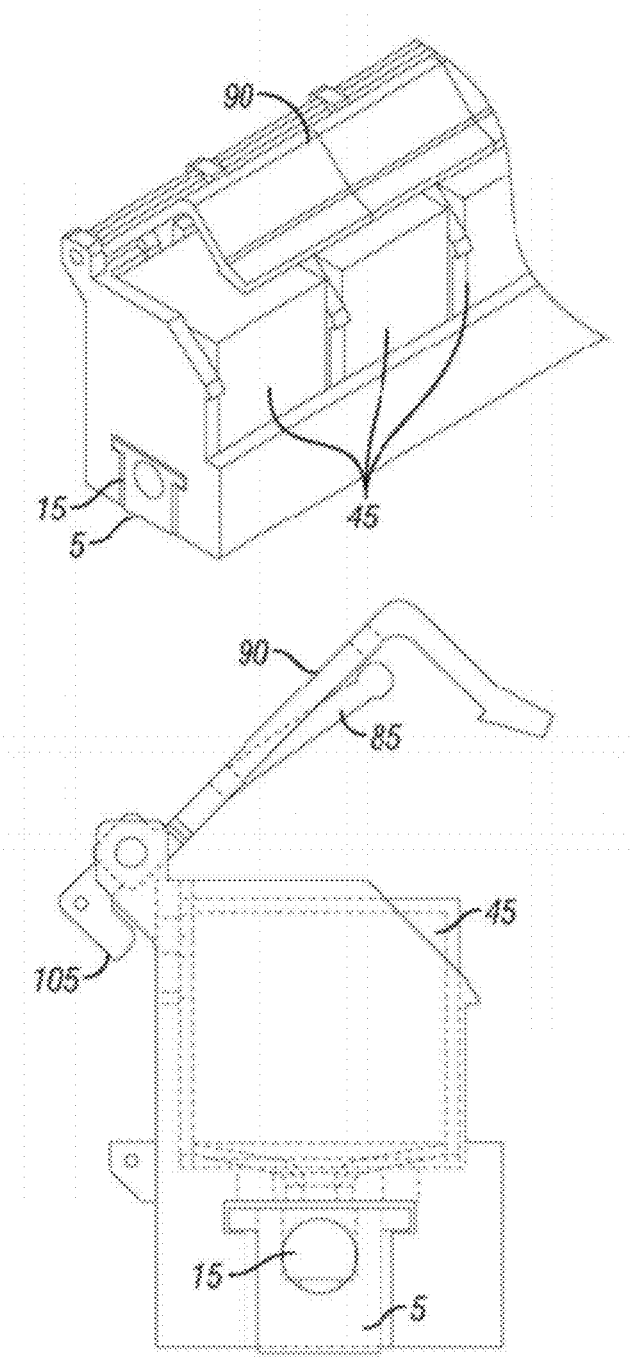
FIG. 12 is an angled top-down view and a side cross-sectional schematic view of removable fluid cartridges that have been inserted in a structural housing that contains a plurality of covers, and wherein the removable fluid cartridges are shown to be fluidly in contact with a fluid channel of an elongate member.

FIG. 12 presents a 45 degree angle and side view of an embodiment of the disclosure, of three removable fluid cartridges 45 in structural housing 95 with three opened covers 90, wherein the removable fluid cartridges 45 are fluidly in contact with a fluid channel 15 of elongate member 5. In an additional embodiment, a rearward disposed hinge 120 pivotally connects cover 90 to the structural housing 95. In a further embodiment, the lip, latch, or flange 100 of cover 90 is provided so that it can engage with the peripheral edges of the structural housing 95, so that when pushed down locks cover 90 in a closed position. In a further embodiment, cover 90 may further comprise bendable flange 85 and cover projection 105.

Figure 13:
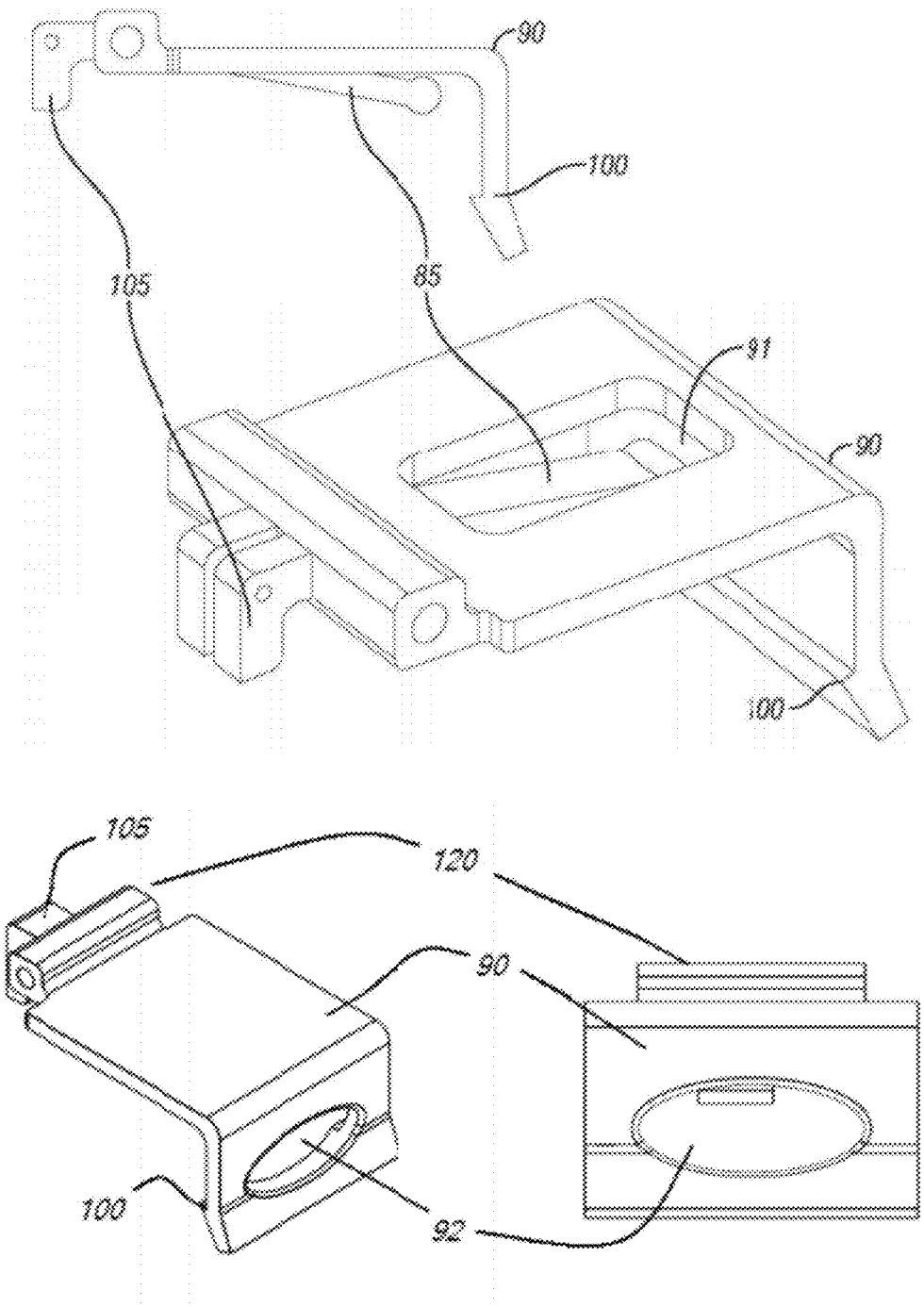
FIG. 13 is a multi-view of a cover that can be attached to a structural housing with a hinge.

FIG. 13 presents various views of a particular embodiment of the disclosure of a cover 90 that is rearwardly attached to structural housing 95 (not shown) with hinge 120, wherein cover 90 has a planar top with a centrally located cavity 91. Cavity 91 can have any shape and dimension, so long as removable fluid cartridge 45 (not shown) can fit within some portion of cavity 91. In a certain embodiment, hinge 120 pivotally connects cover 90 to structural housing 95 (not shown). The front of the cover 90 may comprise a lip, latch, or flange 100 that extends essentially at a 90° angle downwardly from the planar top of cover 90. In a further embodiment, the lip, latch, or flange 100 is provided with a recessed edge that can engage with the peripheral edge of structural housing 95 (not shown), in such a way that when cover 90 is pushed down the lip, latch, or flange 100 securely snaps into the peripheral edge of structural housing 95 (not shown) holding cover 90 closed. In yet a further embodiment, cover 90 comprises a centrally located bendable flange 85 which is attached to the rear edge of the cover 90 and extends into cavity 91, wherein bendable flange 85 can apply downward pressure to the top of a removable fluid cartridge 45 (not shown) once it is placed inside structural housing 95 (not shown). Bendable flange 85 may further allow cover 90 to snap open to an upright position once lip, flange, or latch 100 is disengaged from the peripheral edge of structural housing 95 (not shown). In a particular embodiment, cover 90 further comprises a cover projection 105 that can be connected to a structural housing projection 110 (not shown) of structural housing 95 (not shown) by using a spring 115 (not shown), such that spring 115 (not shown) provides tension so that the cover 90 will remain in an opened upright position when lip, flange, or latch 100 is disengaged from the peripheral edge of structural housing 95 (not shown). In a further embodiment, cover 90 may further comprise cover window 92. Cover window 92 facilitates the reading by eye or by a detector 36 (not shown) of a label 38 (not shown), a machine readable indicator 48 (not shown), or a combination thereof, wherein the label 38 (not shown), the machine readable indicator 48, or a combination thereof is located on the upper front face of a removable fluid cartridge 45 (not shown). Cover window 92, may have any shape, so long as the label 38 (not shown), machine readable indicator 48, or a combination thereof of a removable fluid cartridge 45, can be read once the lip, flange, or latch 100 is engaged with the peripheral edge of structural housing 95 (not shown). For example, cover window 92, may be square, rectangular, circular, oval, trapezoidal, or any other shape that contains an open spaced enclosed by at least three walls.

Figure 14:
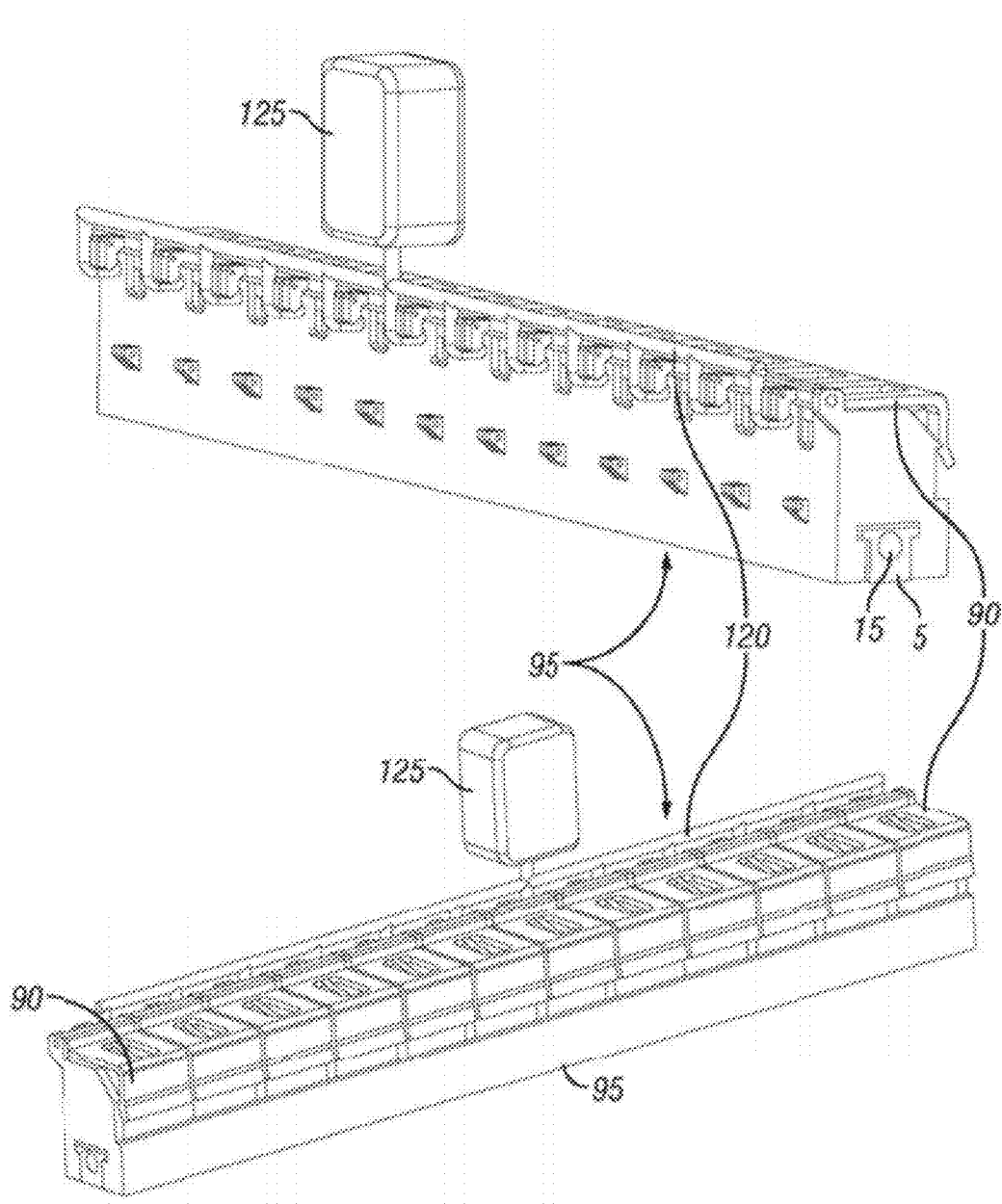
FIG. 14 is an angled top-down and side view of a partially assembled fluid delivery device.
Figure 15:
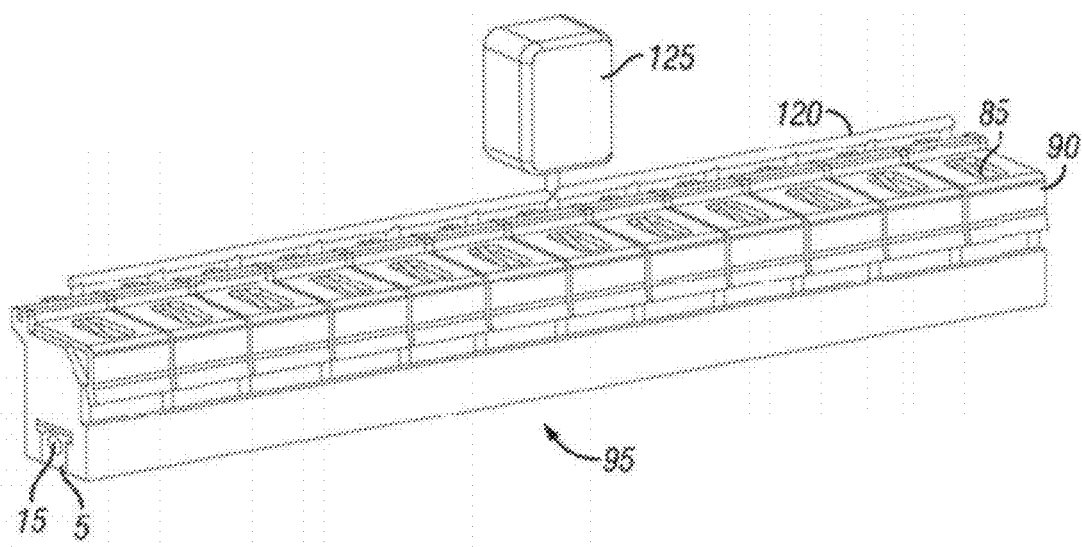
FIG. 15 is an angled front view of a partially assembled fluid delivery device.

FIGS. 14-15 provide various schematic representations of an embodiment of a fluid delivery device of the disclosure. It should be understood that the fluid delivery device presented in FIGS. 13-14 embody only an exemplary version of a fluid delivery device of the disclosure, and additional fluid delivery devices are disclosed and in-fact presented in additional Figures of the application. Moreover, the mechanism to deliver fluid in the delivery device shown in FIGS. 13-14 are not presented as the definitive method to deliver such fluids, as the disclosure provides for alternative embodiments to deliver metered doses of fluids using a delivery device of the disclosure. Moreover, multiple fluid delivery devices of the disclosure can be stacked on top of each other to make the fluid delivery devices disclosed herein, scalable, and correspondingly the amount of fluid delivered is also scalable.

As shown, elongate member 5 comprising fluid channel 15 is slideably in contact with matching elongate member depression 80 of structural housing 95. A plurality of removable fluid cartridges 45 (not shown) are aligned with a plurality of fluid cartridge adapters 10 (not shown). A plurality of lips, latches, or flanges 100 are engaged with the peripheral edge of structural housing 95 holding a plurality of covers 90 in a closed position. In a further embodiment, a plurality of covers 90 comprise bendable flange 85.

As shown, in a particular embodiment, the disclosure provides for a fluid delivery device disclosed herein, wherein one or more pressure modifying devices 125 is pressureably linked to a fluid channel 15 so as to provide positive pressure to push liquid from a removable fluid cartridge 45 (not shown) into fluid channel 15. In a particular embodiment, the disclosure provides a fluid delivery device disclosed herein, wherein a pressure modifying device 125 is pressureably linked to a fluid channel 15 through delivery pressure delivery tubing 120 so as to provide positive pressure to push liquid from a removable fluid cartridge 45 (not shown) into fluid channel 15. Delivery tubing 120 can be made from any material, including, but not limited to, metal, rubber, plastic, latex, nitrile, and silicone. In an alternate embodiment, the disclosure provides for a fluid delivery device, wherein one or more pressure modifying devices 125 are operably linked to the fluid channel 15 so as to provide negative pressure to draw liquid from a removable fluid cartridge 45 into the fluid channel 15. In a further embodiment, the pressure modifying device 125 can either provide positive or negative pressure to force or draw the fluid from a removable fluid cartridge 45 (not shown) through the ejection port 46 (not shown) and into the fluid channel 15. Examples of pressure modifying devices include, but are not limited to, pumps, compressed gas cylinders, air compressors, vacuums, and building supplied air and vacuum sources. Moreover, the pressure modifying devices can exert pressure by increasing or decreasing air pressure; physical compression, such as by pressing down on a syringe plunger; injecting a gas, such as carbon dioxide or air, into a removable fluid cartridge; or a combination thereof.

In a particular embodiment, one or more pressure modifying device 125 comprises one or more pumps. Examples of pumps which can be used with the fluid delivery device disclosed herein, include, but are not limited to, syringe pumps; piezoelectric pumps; positive displacement pumps, including rotary-type, such as gear pumps, cavity pumps, lobe pumps, screw pumps, and rotary vane pumps, reciprocating-type, such as plunger pumps, diaphragm pumps, piston pumps, and linear type pumps; hydraulic pumps; impulse pumps; centrifugal pumps; velocity pumps; and peristaltic pumps.

In a certain embodiment, one or more pressure modifying devices 125, such as pumps, can be controlled by a computer 180 (not shown). In another embodiment, a computer 180 (not shown) used to control a pressure modifying device 125 can be accessed directly, wirelessly, or remotely through the internet, phone line, or a network. In yet another embodiment, one or more pressure modifying devices 125 can be controlled by a user entering commands on a user interface connected to a computer 180 (not shown). In a further embodiment, one or more pressure modifying devices 125 can be controlled by a computer 180 (not shown) that is accessed through the internet, network, or phone line from commands entered on a user interface that is connected to an alternate computer.

In a further embodiment, delivery tubing 120 can further comprise one or more pressure regulating valves that can control the amount of pressure that each removable fluid cartridge 45 receive from one or more pressuring modifying devices 125. Examples of pressure regulating valves include, but are not limited to, solenoids, electronic actuators, pneumatic actuators, hydraulic actuators, handles, butterfly valves, plug valves, and pilot valves. In a certain embodiment, the pressure regulating valves can be opened or closed using a computer. In a further embodiment, the pressure regulating valves can be opened or closed by using commands from a user interface connected to a computer. Examples of a user interface include, but are not limited to, keyboards, mouse, light pens, and touchscreens.

Figure 16:
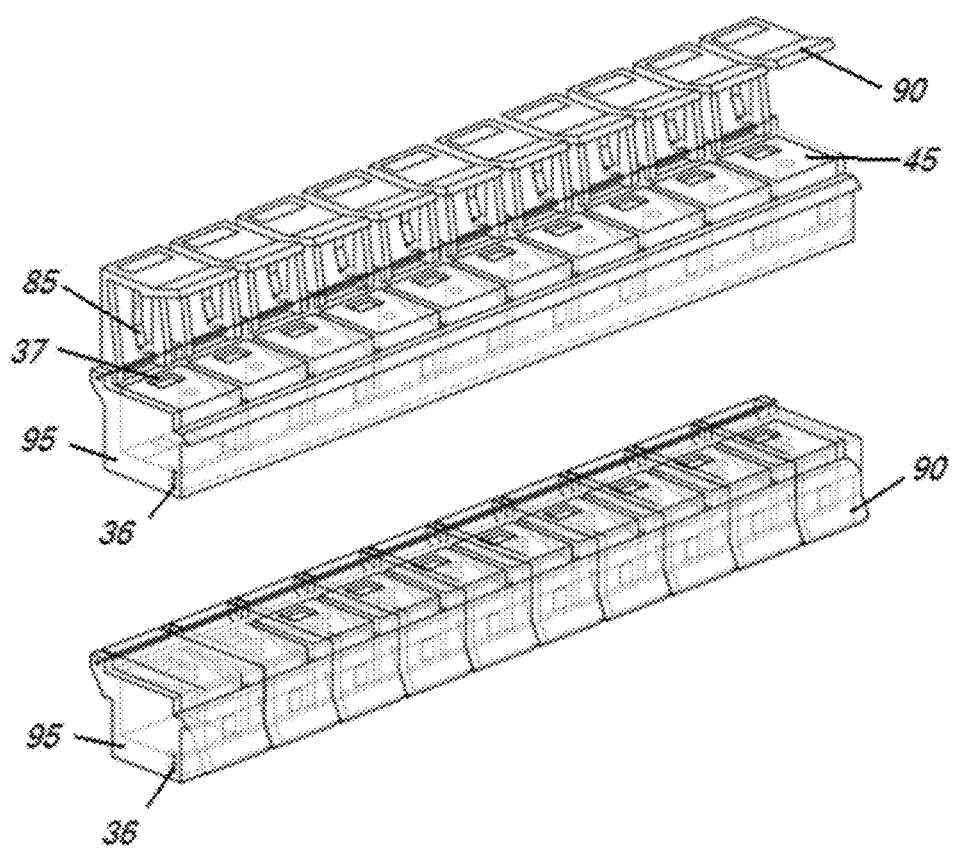
FIG. 16 is an angled top-down and rear view of a partially assembled fluid delivery device.

FIG. 16 provides various schematic representations of an embodiment of a fluid delivery device of the disclosure. It should be understood that the fluid delivery device presented in FIG. 16 embodies only an exemplary version of a fluid delivery device of the disclosure, and additional fluid delivery devices are disclosed and in-fact presented in additional Figures of the application. Moreover, the mechanism to deliver fluid in the delivery device shown in FIG. 16 is not presented as the definitive method to deliver such fluids, as the disclosure provides for alternative embodiments to deliver metered doses of fluids using a delivery device of the disclosure. Moreover, multiple fluid delivery devices of the disclosure can be stacked on top of each other to make the fluid delivery devices disclosed herein, scalable, and correspondingly the amount of fluid delivered is also scalable.

In a particular embodiment, the disclosure provides for a structural housing 95 comprising a series of bays in which a plurality of removable fluid cartridges 45 can be inserted, so that the removable fluid cartridges 45 are in fluidly contact with a fluid channel 15 (not shown). In a further embodiment, structural housing 95 may further comprise a plurality of covers 90 that are further comprised of bendable flange 85 which can insert into a bendable flange depression 37 found on top of removable fluid cartridge 45. In yet another embodiment, a structural housing 95 may further comprise a detector 36 which can detect a machine readable code 48 (not shown).

Figure 17:
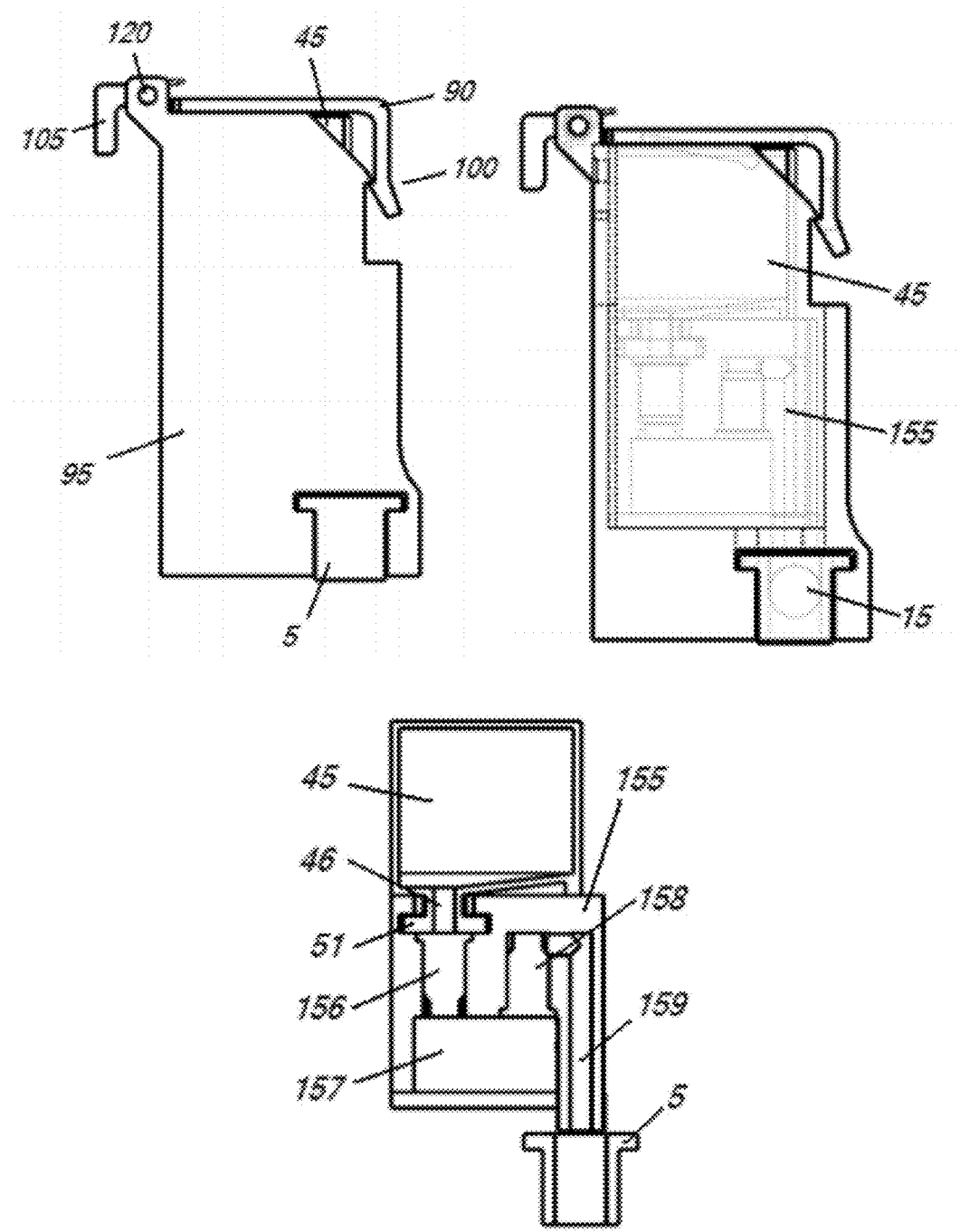
FIG. 17 is a side view, cross-sectional schematic view and cut away view of a dual cartridge system inserted into a structural housing and in fluidly contact with a fluid channel of an elongate member.

FIG. 17 presents multiple side views of an embodiment of a fluid delivery device of the disclosure. As shown, elongate member 5 comprising fluid channel 15, has been slideably connected to structural housing 95, by sliding elongate member 5 into a matching elongate member depression 80 of structural housing 95. Structural housing 95 comprises cover 90 that is connected to structural housing 95 with hinge 120, and further comprises cover projection 105. As shown, a lip, latch, or flange 100 is engaged with the peripheral edge of structural housing 95 thereby holding cover 90 in a closed position.

A dual fluid cartridge system, an embodiment of the disclosure, is presented, wherein the dual fluid cartridge system comprises a removable fluid cartridge 45 that is fluidly in contact with a self-contained pump dispensing cartridge 155 that is in fluidly contact with fluid channel 15, so that a diaphragm 157 that is pressureably in contact with fluid channel 15 can either by changing the pressure to draw fluid from the removable fluid cartridge 45 into self-contained pump dispensing cartridge 155 and then force the fluid from self-contained pump dispensing cartridge 155 into fluid channel 15.

In a certain embodiment, removable fluid cartridge 45 further comprises a cartridge attachment projection 51 having a centrally orientated ejection port 46. In another embodiment, self-contained pump dispensing cartridge 155 further comprises deformable input one-way valve 156. In yet another embodiment, self-contained pump dispensing cartridge 155 further comprises diaphragm 157. In a certain embodiment, diaphragm 157 is dimensioned so as it can be used to deliver a desired metered amount of fluid contained in diaphragm 157. In a further embodiment, self-contained pump dispensing cartridge 155 further comprises deformable output one-way valve 158. In another embodiment, self-contained pump dispensing cartridge 155 further comprises dispensing channel 159. In a particular embodiment, a self-contained pump dispensing cartridge comprises one or more of deformable input one-way valve 156, diaphragm 157, deformable output one-way valve 158, and dispensing channel 159. In yet a further embodiment, self-contained pump dispensing cartridge 155 comprises deformable input one-way valve 156, diaphragm 157, deformable output one-way valve 158, and dispensing channel 159. Dispensing channel 159 can be of any length, so long as cartridge receiving adapter 10 (not shown) can receive fluid from dispensing channel 159.

Figure 18:
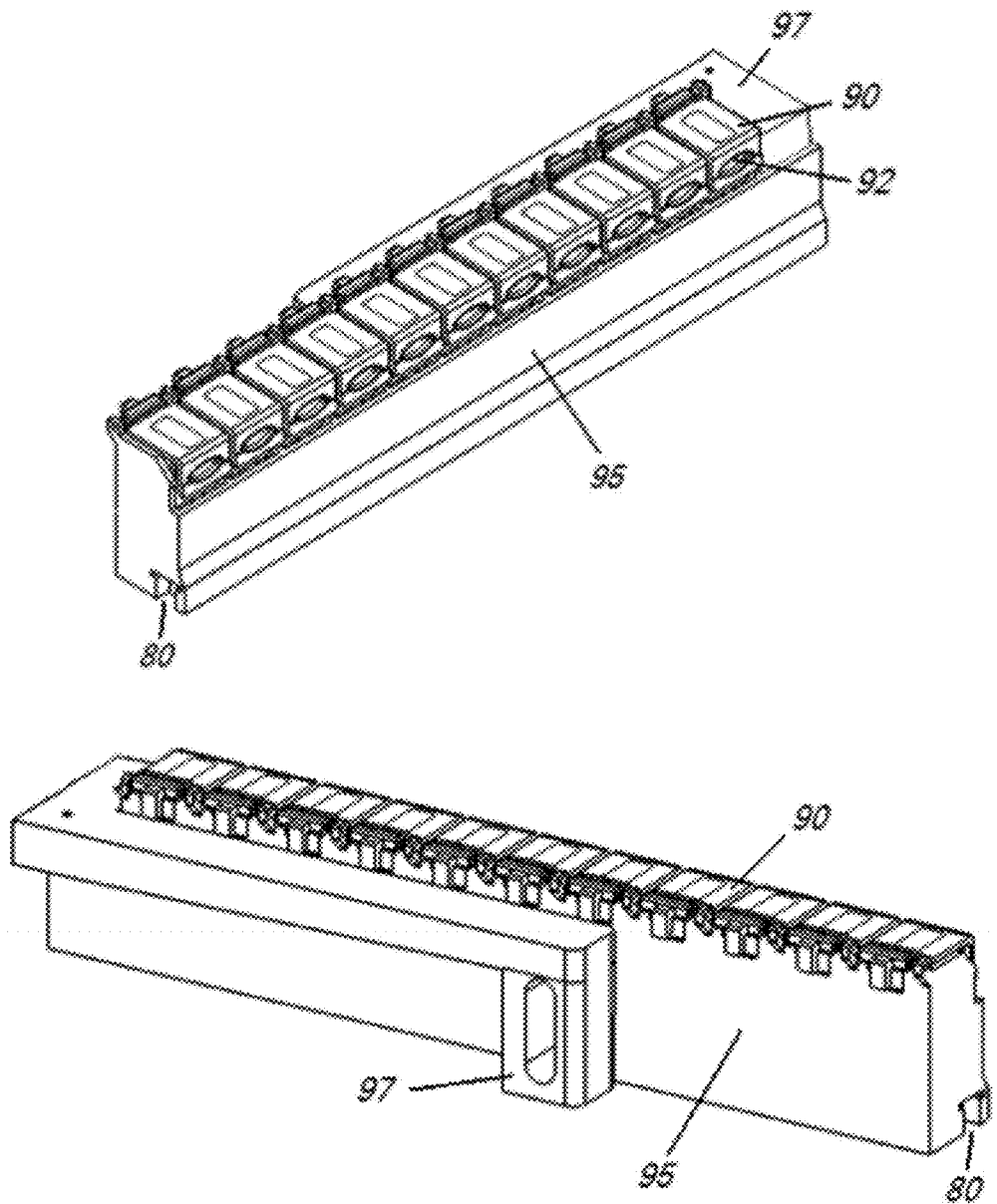
FIG. 18 is an angled frontal view of a partially assembled fluid delivery device.

FIG. 18 provides various schematic representations of an embodiment of a fluid delivery device of the disclosure. It should be understood that the fluid delivery device presented in FIG. 18 embodies only an exemplary version of a fluid delivery device of the disclosure, and additional fluid delivery devices are disclosed and in-fact presented in additional Figures of the application. Moreover, the mechanism to deliver fluid in the delivery device shown in FIG. 18 is not presented as the definitive method to deliver such fluids, as the disclosure provides for alternative embodiments to deliver metered doses of fluids using a delivery device of the disclosure.

Moreover, multiple fluid delivery devices of the disclosure can be stacked on top of each other to make the fluid delivery devices disclosed herein, scalable, and correspondingly the amount of fluid delivered is also scalable.

An embodiment of structural housing 95 comprising a plurality of dual cartridge systems comprising a removable fluid cartridge 45 (not shown) connected to self-contained pump dispensing cartridge 155 (not shown), a matching elongate member depression 80, and a plurality of closed cover 90 is presented. A further embodiment, of a plurality of covers 90 comprising cover window 92 is shown. In yet a further embodiment, a dispensing tank 97 that is fluidly in contact with fluid channel 15 is also presented.

Figure 19:
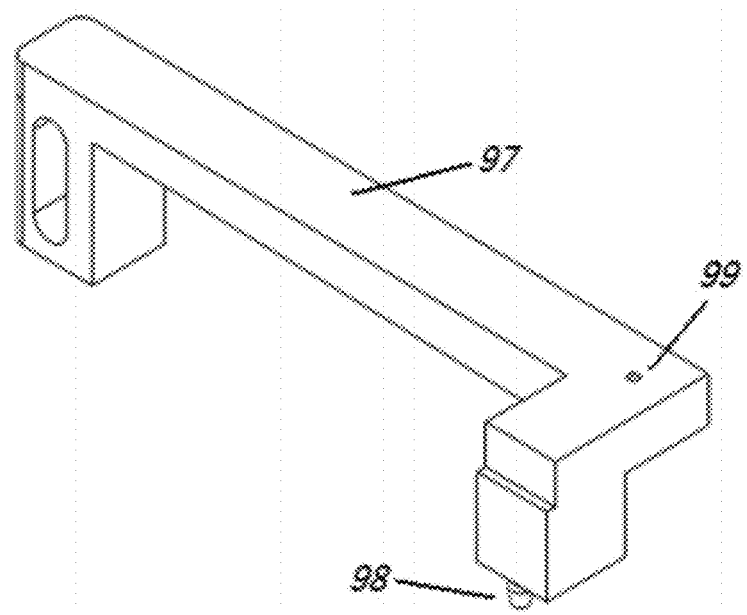
FIG. 19 is an angled top-down and side view of a dispensing tank, and an assembled fluid delivery device, respectively.
Figure 19:
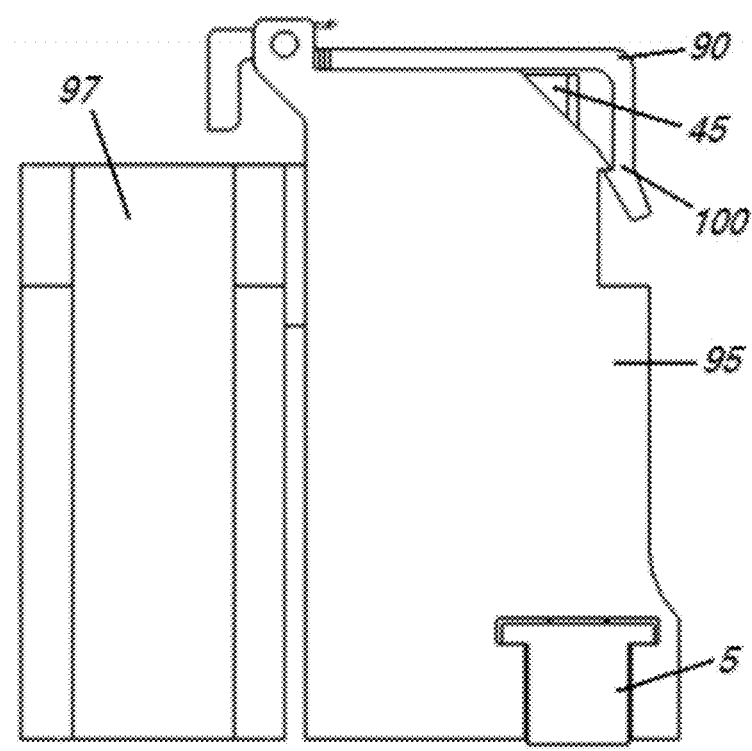
Figure 20:
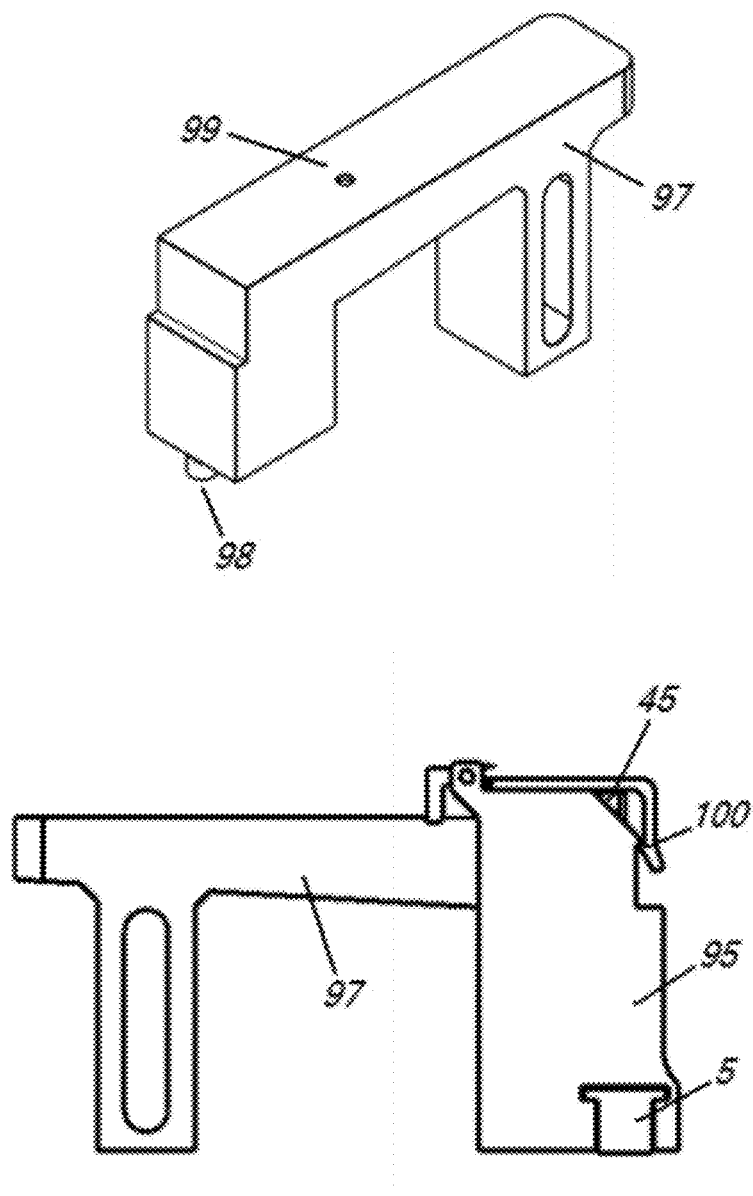
FIG. 20 is an angled top-down and side view of a dispensing tank, and an assembled fluid delivery device, respectively.

FIGS. 19 and 20 presents a close-up view of a certain embodiment of the disclosure of a dispensing tank 97, further comprising tank ejection port 98 and air-relief vent 99, wherein tank ejection port 98 is in fluidly contact with fluid channel 15 when dispensing tank 97 is inserted into structural housing 95.

In a certain embodiment, fluid from one or more removable fluid cartridge 45 that have accumulated in fluid channel 15 and/or in the exit portal can be flushed to the distal end of the exit portal by using fluid in dispensing tank 97. In a further embodiment, dispensing tank 97 is pressureably connected to pressure modifying device 125 (not shown), so that dispensing tank releases small amounts of fluid into the fluid channel when the pressure on the fluid in dispensing tank 97 is modified. In an alternate embodiment, dispensing tank 97 is pressureably connected to pressure modifying device 125 (not shown), so that dispensing tank releases large amounts of fluid into the fluid channel when the pressure on the fluid in dispensing tank 97 is modified. In a particular embodiment, dispensing tank 97 is parallel and located directly behind structural housing 97. In a particular embodiment, dispensing tank 97 is perpendicular and located directly behind structural housing 97. In an additional embodiment, dispensing tank 97 can hold up to one liter of fluid. In a further embodiment, dispensing tank 97 further comprises self-contained pump dispensing cartridge 155, wherein tank ejection port 98 is fluidly in contact with one way valve 156 of dispensing cartridge 155, and wherein dispensing channel 159 is in fluidly contact with fluid channel 15. In another embodiment, dispensing tank 97 is angled to facilitate the flow of liquid to dispensing cartridge 155 by gravity. In a particular embodiment, air relief vent 99 is open to environmental air. In additional embodiment, air relief vent 99 is fluidly connected to a pressurized gas source. In yet a further embodiment, air relief vent 99 is pressureably linked to a pressure modifying device 125 (not shown).

Figure 21:
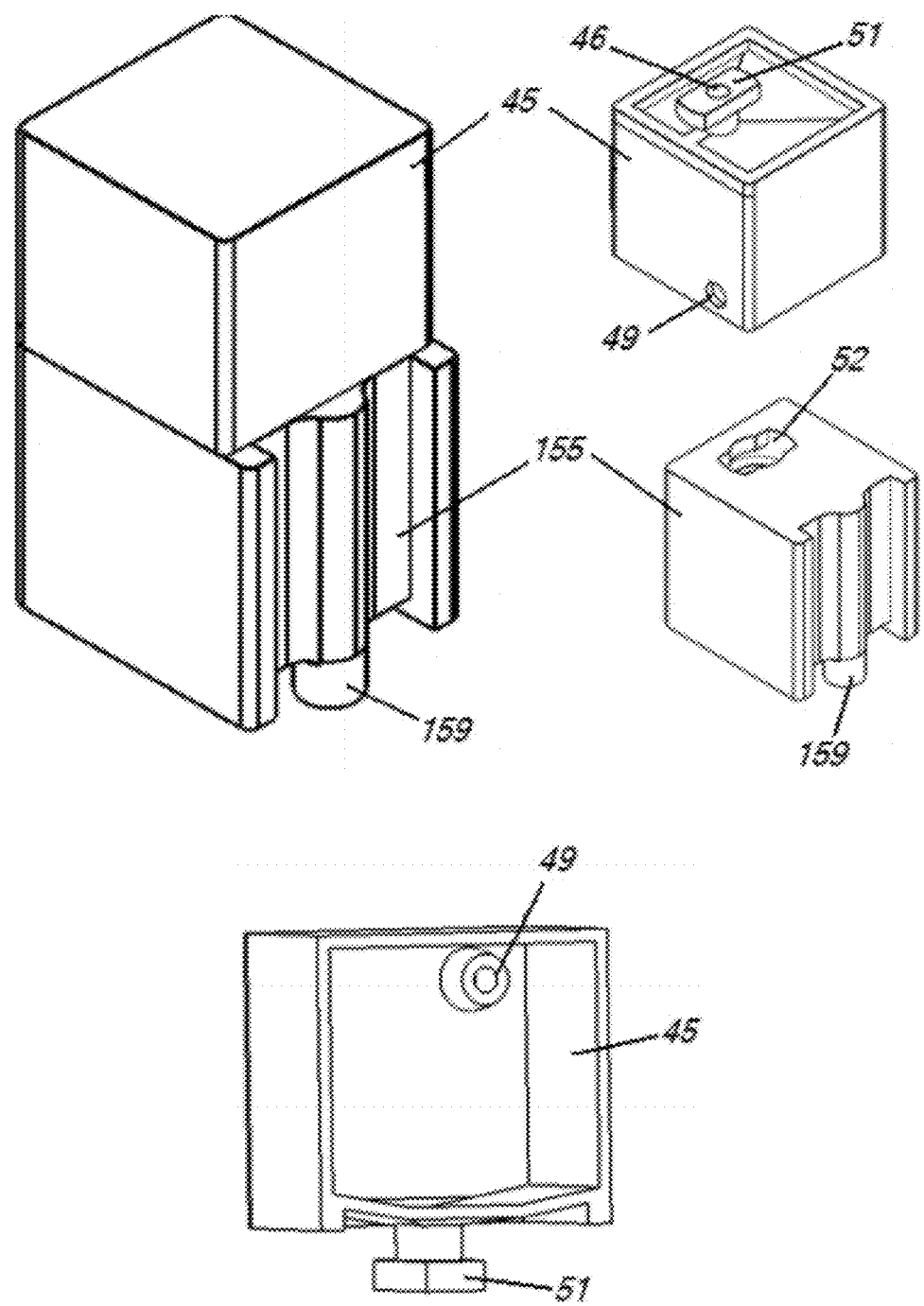
FIG. 21 is a close-up view and a cut-away view of the components for a dual fluid cartridge system.

FIG. 21 presents close-up views of particular embodiments of the disclosure of an attached dual fluid cartridge system, a removable fluid cartridge 45, and a self-contained pump dispensing cartridge 155. In a certain embodiment, a removable fluid cartridge 45 comprises a cartridge attachment projection 51 having a centrally orientated ejection port 46. In another embodiment, a removable fluid cartridge 45 further comprises an air relief vent 49 located at or near the top edge of the rear face. In another embodiment, a self-contained pump dispensing cartridge 155 comprising dispensing channel 159 further comprises a cartridge attachment depression 52, such that cartridge attachment projection 51 of a removable fluid cartridge 45 can slideably insert into cartridge attachment depression 52 of self-contained pump dispensing cartridge 155.

Figure 22:
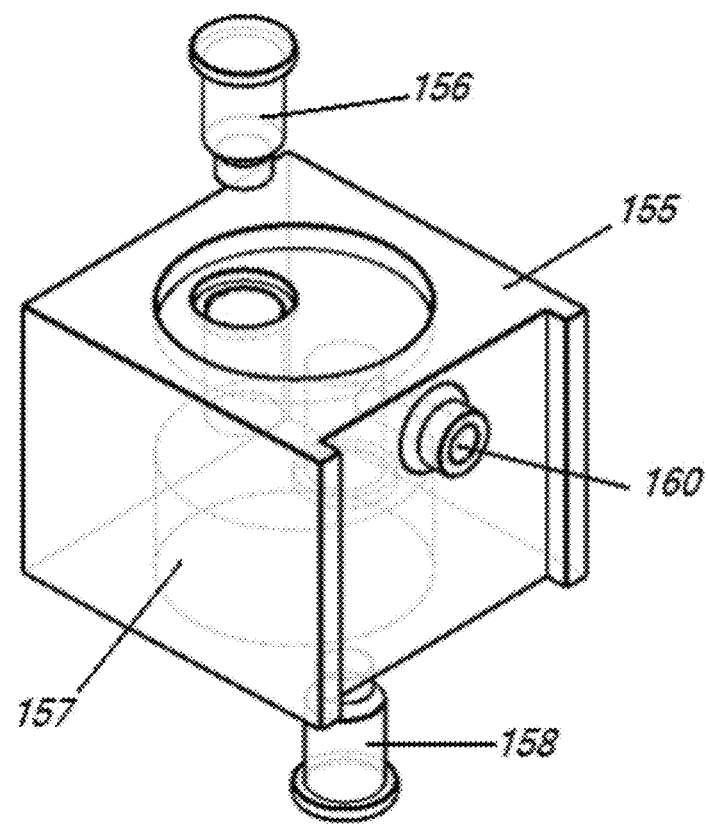
FIG. 22 is a cross-sectional schematic view of a self-contained pump dispensing cartridge of a dual fluid cartridge system.
Figure 22:
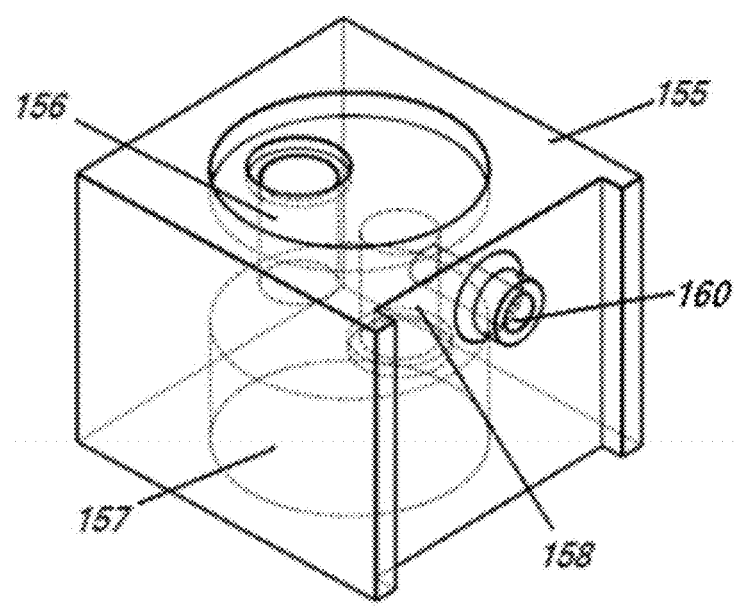

FIG. 22 presents close up cut away views of a self-contained pump dispensing cartridge 155 of the disclosure. Dispensing cartridge 155 is comprised of a deformable input one-way valve 156, a diaphragm 157, a deformable output one-way valve 158, and dispensing nozzle 160, wherein dispensing cartridge 155 can perform a repeating pumping cycle of (a) and (b) comprising: (a) diaphragm 157 is pulled outward and fluid is drawn into diaphragm 157 through deformable input one-way valve 156 from removable fluid cartridge 45 (not shown); and (b) diaphragm 157 is then pushed inward forcing fluid from diaphragm 157 through deformable output one-way valve 158 and out dispensing nozzle 160. In a certain embodiment, deformable output one-way valve 158 is connected to dispensing channel 159 (not shown) through dispensing nozzle 160. In a preferred embodiment, deformable output one-way valve 158 is connected directly to dispensing channel 159 (not shown) so as to form a right angle without having to go through dispensing nozzle 160.

In a certain embodiment, diaphragm 157 is made of a magnetic material. In a certain embodiment, diaphragm 157 is made of stainless steel. In an alternate embodiment, diaphragm 157 is made of any material that can flex and in which a magnet can be attached. In a certain embodiment, diaphragm 157 can be pushed inward and pulled outward by alternating the magnetic force generated by an electromagnet.

In another embodiment, diaphragm 157 is made of a flexible non porous material. In further, diaphragm 157 can be pushed inward and pulled outward by using any physically means, such as diaphragm 57 is attached to a part that is moved up and down by using a motor.

Figure 23:
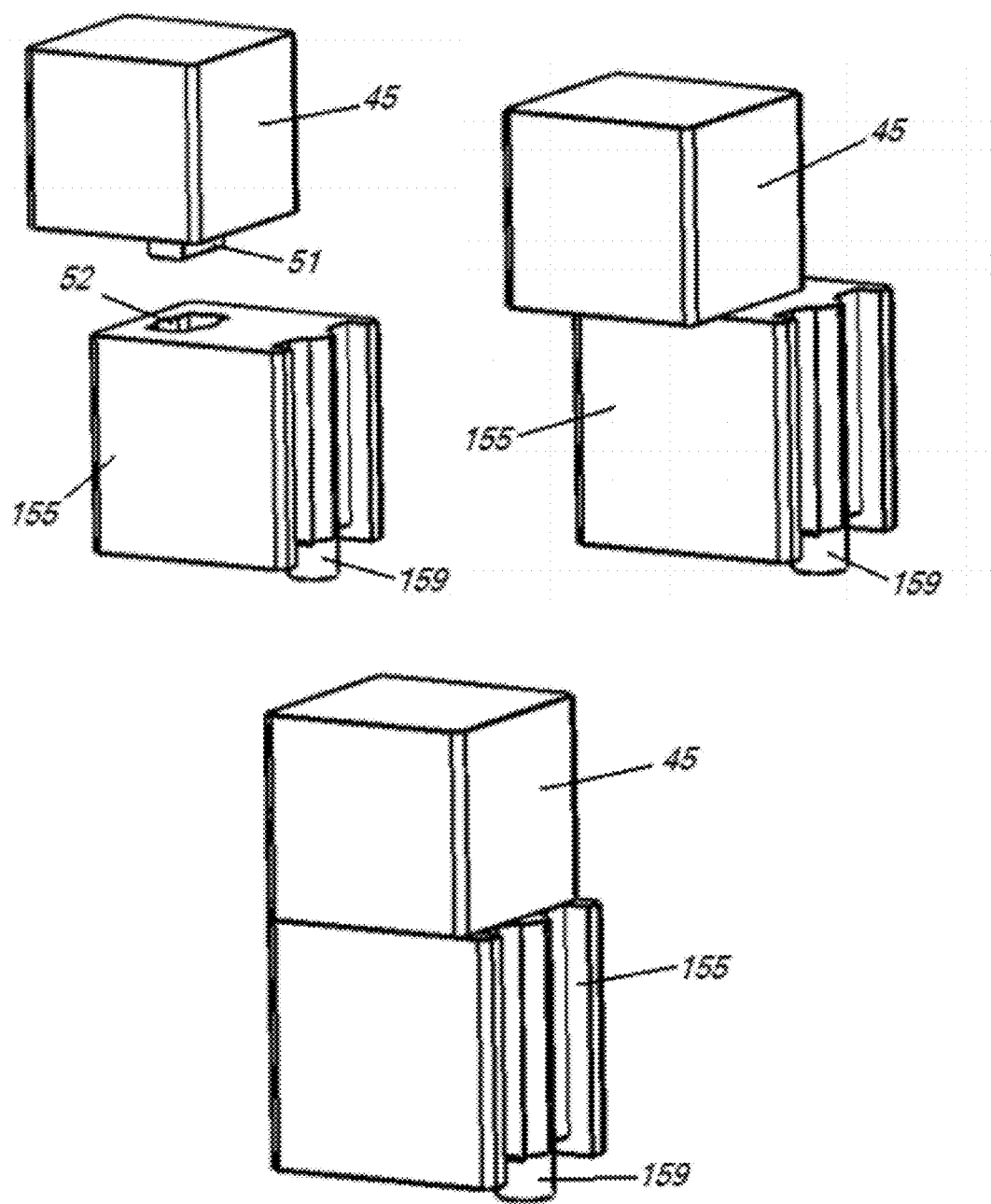
FIG. 23 is a close-up view of steps for assembling a dual fluid cartridge system.

FIG. 23 presents a series of views of an exemplary embodiment of the disclosure of assembling a self-contained pump dispensing cartridge 155 of the disclosure with a removable fluid cartridge 45 of the disclosure to form a dual cartridge system disclosed herein. In a particular embodiment, a removable fluid cartridge 45 comprising a cartridge attachment projection 51 is slideably inserted into a cartridge attachment depression 52 of self-contained pump dispensing cartridge 155, wherein removable fluid cartridge 45 can be firmly attached to self-contained pump dispensing cartridge 155 by rotating approximately 180 degrees around a horizontal axis, such that one or more faces of removable fluid cartridge 45 are substantially continuous with one or more faces of the self-contained pump dispensing cartridge 155.

Figure 24:
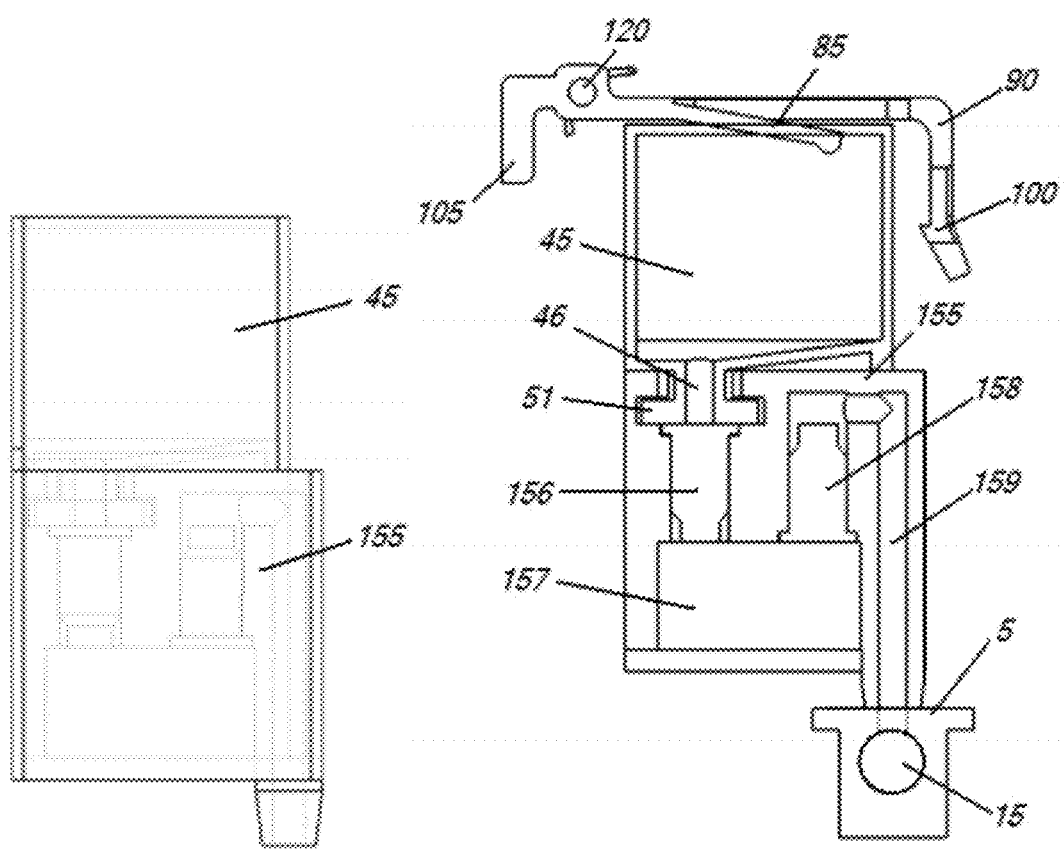
FIG. 24 is a cross-sectional schematic view of a dual fluid cartridge system, and how the system feeds into the fluid channel of an elongate member.

FIG. 24 presents a cut-out and close-up view of a certain embodiment of the disclosure of a dual fluid cartridge system. A removable fluid cartridge 45 comprising a centrally orientated ejection port 46 in a cartridge attachment projection 51, is shown fluidly and physically attached to a self-contained pump dispensing cartridge 155 comprising a deformable input one-way valve 156, diaphragm 157, a deformable output one-way valve 158, and dispensing channel 159, and wherein dispensing channel 159 is fluidly in contact with an elongate member 5 comprising fluid channel 15. In a further embodiment, a cover 90 comprises cover projection 105, hinge 120, lip, flange or notch 100, and bendable flange 85, such that bendable flange 85 is contacting removable fluid cartridge 45 and providing downward pressure on removable fluid cartridge 45.

Figure 25:
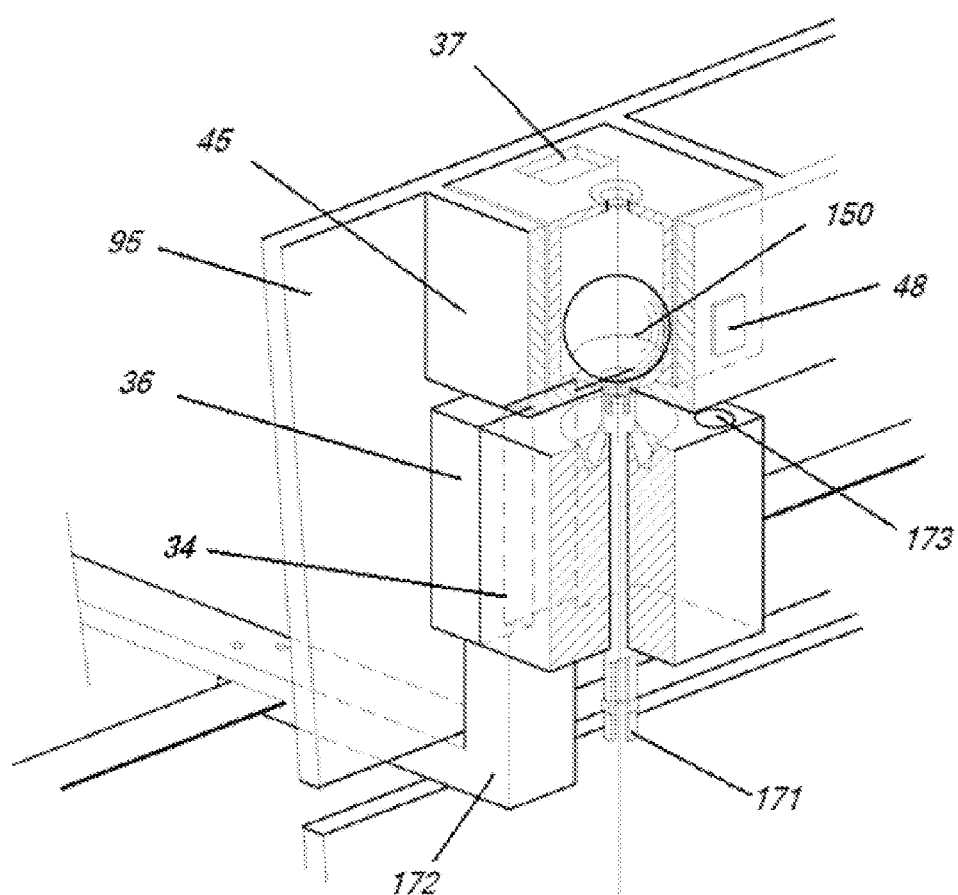
FIG. 25 is a cut away schematic view of a robotic version of a fluid delivery device.

FIG. 25 provides a various schematic representations of an embodiment of a fluid delivery device of the disclosure. It should be understood that the fluid delivery device presented in FIG. 25 embodies only an exemplary version of a fluid delivery device of the disclosure, and additional fluid delivery devices are disclosed and in-fact presented in additional Figures of the application. Moreover, the mechanism to deliver fluid in the delivery device shown in FIG. 25 is not presented as the definitive method to deliver such fluids, as the disclosure provides for alternative embodiments to deliver metered doses of fluids using a delivery device of the disclosure. Moreover, multiple fluid delivery devices of the disclosure can be stacked on top of each other to make the fluid delivery devices disclosed herein, scalable, and correspondingly the amount of fluid delivered is also scalable.

In a particular embodiment, of the disclosure, structural housing 95 may further have a robotically controlled dispenser block 34. In a further embodiment, dispenser block 34 may further comprise a valve displacing needle 171 that can displace valve 150 from an ejection port 46 of a removable fluid cartridge 45. In yet a further embodiment, dispenser block 34 is robotically moved to be placed directly under one or more fixed removable cartridges 45, so that the valve displacing needle 171 can be inserted into an ejection port 46 (not shown) to displace a valve 150 and in doing so forms a hermetic seal with ejection port 46 so that fluid can then by delivered from removable cartridge 45 to a fluid channel 15 through a fluid channel disposed within valve displacing needle 171. In yet another embodiment, dispenser block 34 may further comprise electro magnetic lock 173, to ensure proper alignment for valve displacing needle 171 when electro magnetic lock 173 is engaged with removable fluid cartridge 45. In another embodiment, dispenser block 34 may further comprise detector 36, which can read a machine readable code 48 (not shown) present on the lower face of removable fluid cartridge 45.

Figure 26:
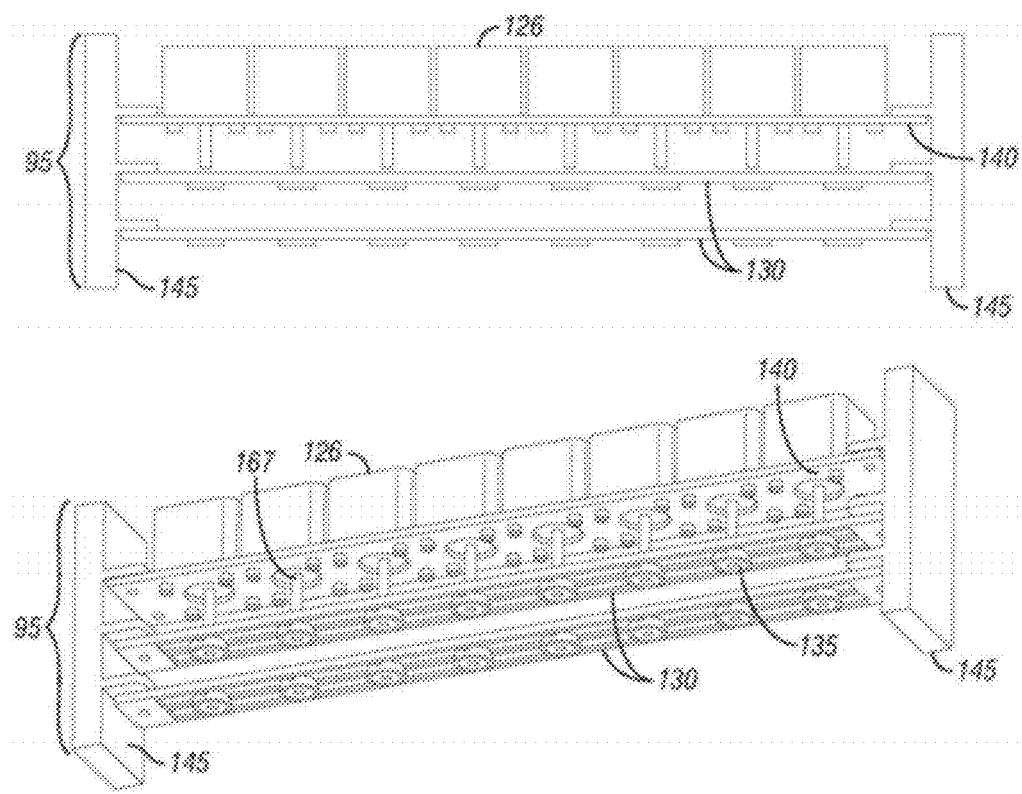
FIG. 26 is a front and angled top down view of a structural housing and fluid cartridge holders.

FIG. 26 presents a front on view and top angled view of an embodiment of the disclosure of a structural housing 95. In certain embodiment, structural housing 95 is comprised of end supports 145. In another embodiment, structural housing 95 is comprised of a one or more of motor mount plates 140. In yet another embodiment, structural housing 95 is comprised of one or more bearing plates 130. In a further embodiment, structural housing 95 is comprised of one or more bearings 135. In yet a further embodiment, structural housing 95 is comprised of end supports 145, one or more motor mount plates 140, one or more bearing plates 130, and one or more bearings 135. In a further embodiment, a motor mount plate 140, may further comprise a plurality of motors 126 attached by a fastening means. Examples of such fastening means, includes fasteners, fastening agents, and welding. In yet a further embodiment, one or more motors further comprise motor shaft 167, such that motor shaft 167 can through a coupler 121 (not shown), turn an elongated and vertically orientated screw 123 (not shown).

Figure 27:
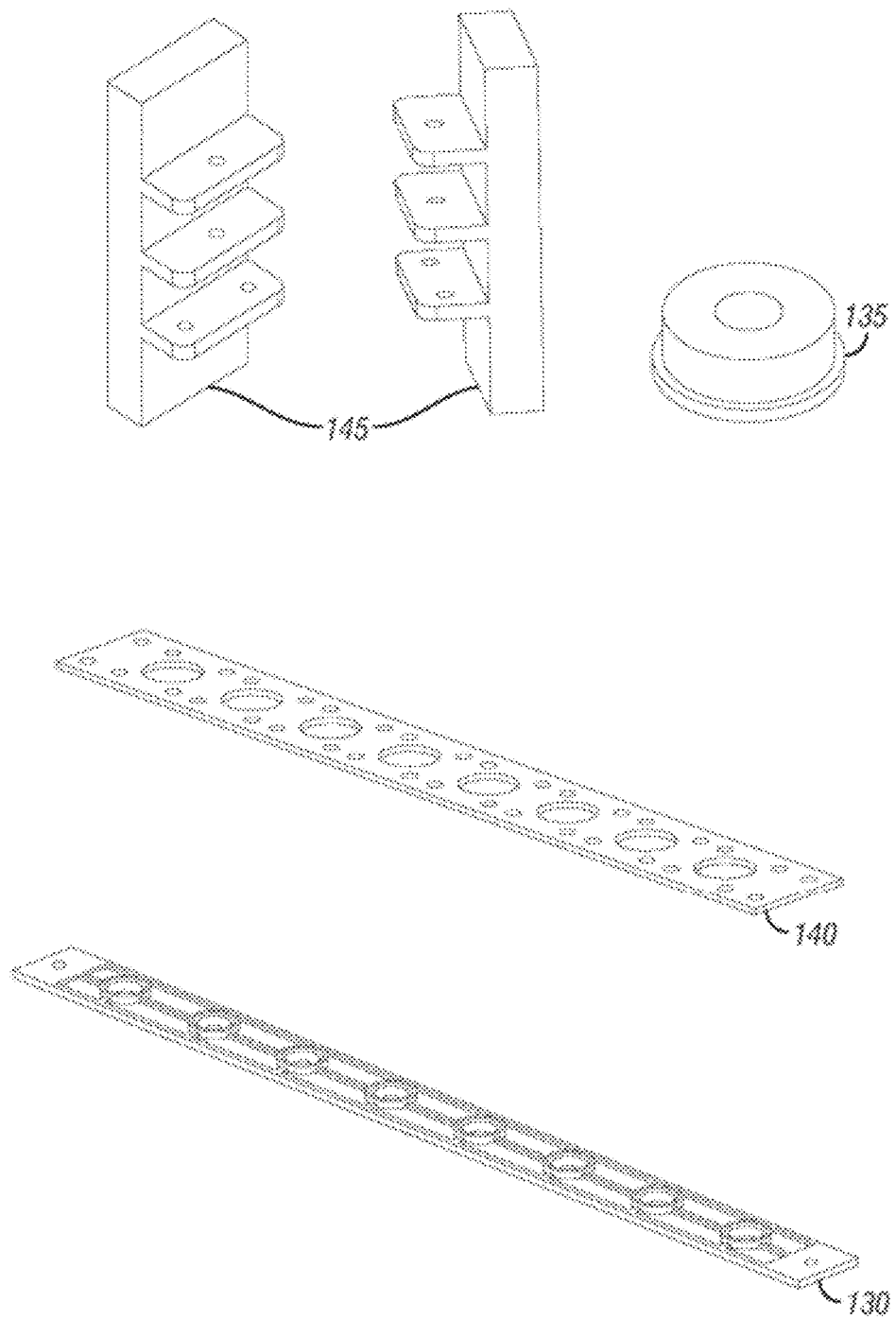
FIG. 27 is a close up view of structural components for assembly into a structural housing.

FIG. 27 shows close-up views of structural parts that can comprise a structural housing 95 of the disclosure. Bearings 135, motor mount 140, end supports 145, and bearing plates 130, may be comprised of any material or combination of materials. In a certain embodiment, bearings 135 are comprised of metal. In another embodiment, bearing plates 130, end supports 145, and motor mount plate 140 are comprised of metal, plastic, or a combination thereof. In a particular embodiment, one or more bearings 135 fit into bearing sized holes in a bearing plate 130. One or more bearing plates 130, motor mount plates 140 and end supports 145 can be fastened together by using one or more types of fastening means. Examples of fastening means, include, but are not limited to, using fasteners, using fastening agents, and welding. Generally, end supports 145 are between 6 to 36 inches in height and between 1 to 12 inches in length and between 0.01 to 1 inch in depth. Generally, motor mount plate 140 and bearing plates 130 have substantially the same length. Motor mount plates 140 and bearing plates 130 and are between 8 to 36 inches in length and be between 0.5 to 6 inches in width.

Figure 28:
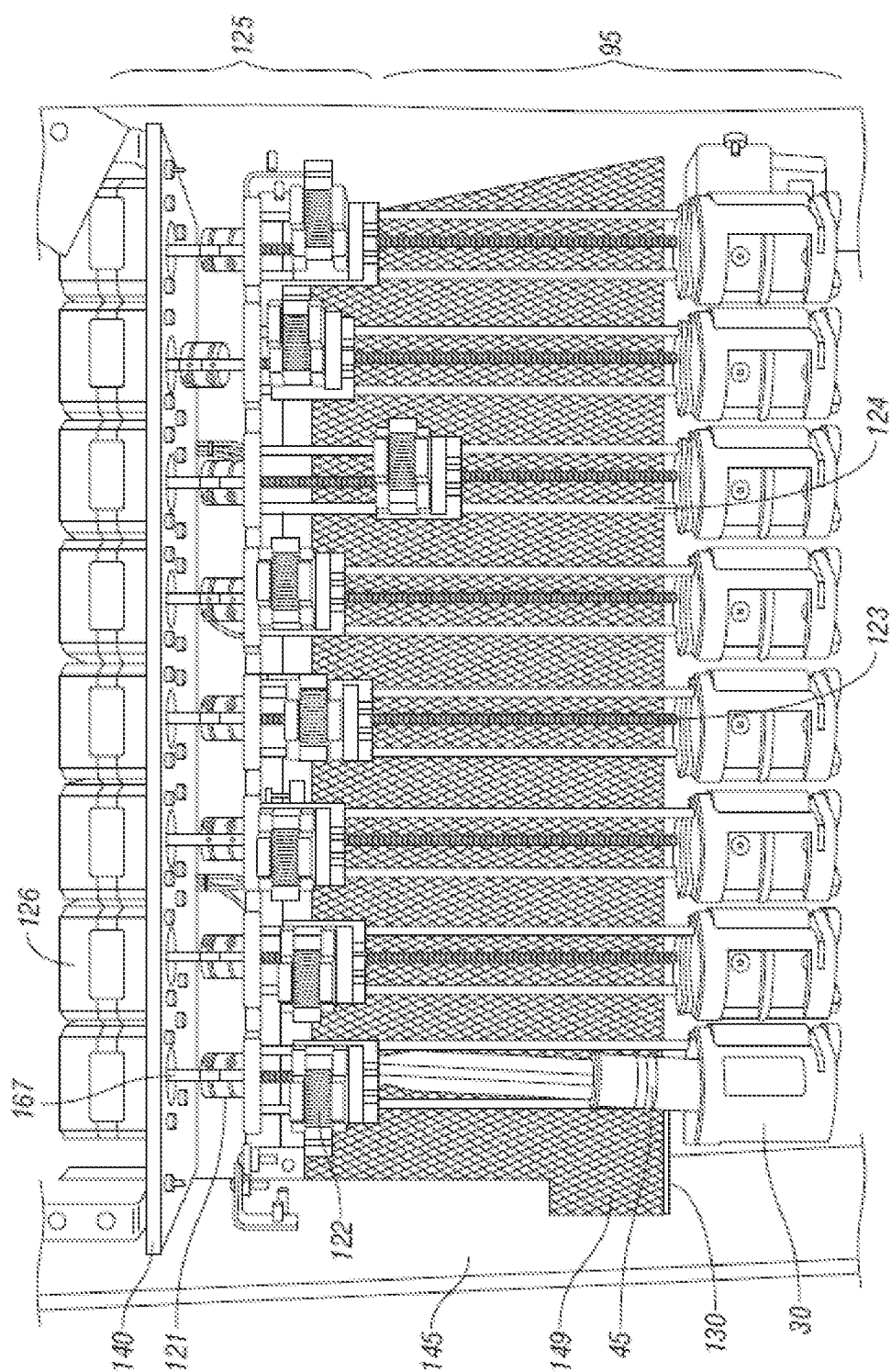
FIG. 28 is frontal view of a partially assembled fluid delivery device.

FIG. 28 provides a schematic representation of an embodiment of a fluid delivery device of the disclosure. It should be understood that the fluid delivery device presented in FIG. 28 embodies only an exemplary version of a fluid delivery device of the disclosure, and additional fluid delivery devices are disclosed and in-fact presented in additional Figures of the application. Moreover, the mechanism to deliver fluid in the delivery device shown in FIG. 28 is not presented as the definitive method to deliver such fluids, as the disclosure provides for alternative embodiments to deliver metered doses of fluids using a delivery device of the disclosure. Moreover, multiple fluid delivery devices of the disclosure can be arranged side by side of each other to make the fluid delivery devices disclosed herein, scalable, and correspondingly the amount of fluid delivered is also scalable.

In a particular embodiment, of the disclosure, a structural housing 95 comprises end supports 145, one or more bearing plates 130, one or more bearings 135, and a motor mount plate 140. Motor mount plate 140 is connected to one or more bearing plates 130 by a plurality of support rods 124, wherein the support rods 124 are connected to the motor mount plate 140 and one or more bearing plates 130 by a fastening means known in the art, and wherein there are at least 2 support rods 124 that are equal distance from an elongated and vertically orientated screw 123. A plurality of elongated and vertically orientated screws 123 are attached by couplers 121 to a plurality of motor shafts 167, and wherein the elongated and vertically orientated screws 123 are turn freely in bearings 135 (not shown) by motors 126 through motor shafts 167 and couplers 121. Syringe plunger drivers 122 are supported by support rods 124 so that the syringe plunger drivers can move freely vertically, but are restricted from moving horizontally. Syringe plunger driver 122 can engage elongated and vertically orientated screw 123 so as to be driven up or down depending on whether elongated and vertically orientated screw 123 is turning clockwise or counterclockwise by motor 126.

In a particular embodiment, syringe plunger driver 122 can engage elongated and vertically orientated screw 123 by a spring means, so that when the spring is compressed by a manual or electronic means the syringe plunger driver is disengaged from elongated and vertically orientated screw 123 and can be moved freely up and down support rods 124, alternatively when the spring is stretched then syringe plunger driver 122 engages the elongated and vertically orientated screw 123 and cannot be moved freely up and down support rods 124.

In a certain embodiment, structural housing 95 is comprised of one or more attached fluid cartridge holders 30. In yet a further embodiment, one or more fluid cartridge holders 30, are securely fastened to a bearing plate 135. One or more cartridge holders 30 can be securely fastened to one bearing plates 135 by any fastening means known in the art, including using fasteners, fastening agents, and welding. In a certain embodiment, cartridge holders 30 are comprised a fixed portion which is attached to a bearing plate 135, while another portion is hingeably attached to the fixed portion and can swing open and closed in a bay door-like manner to facilitate inserting and removing a removable fluid cartridge holder 45.

In another embodiment, a posterior portion of structural housing 95 comprises a wire holding cage 149 that comprises wiring from various electronic devices, such as wiring from one or more pressure exerting devices 125. In a further embodiment wire holding cage 149 is a grated structure. In a particular embodiment, wire holding cage 149 can comprise a solid face of a clear material that can extend up to the length of the height of the structural housing 95. In a certain embodiment, a wire holding cage 149 having a solid face of a clear material may further comprise one or more LED lights. In yet a further embodiment wire holding cage 149 is a box-like structure, wherein at least one portion of the box-like structure which can be detachably an attachably opened or closed, respectively, to access the interior portion of the box-like structure. In yet another embodiment, wire holding cage 149 may further comprise one or more detectors 36.

Figure 29:
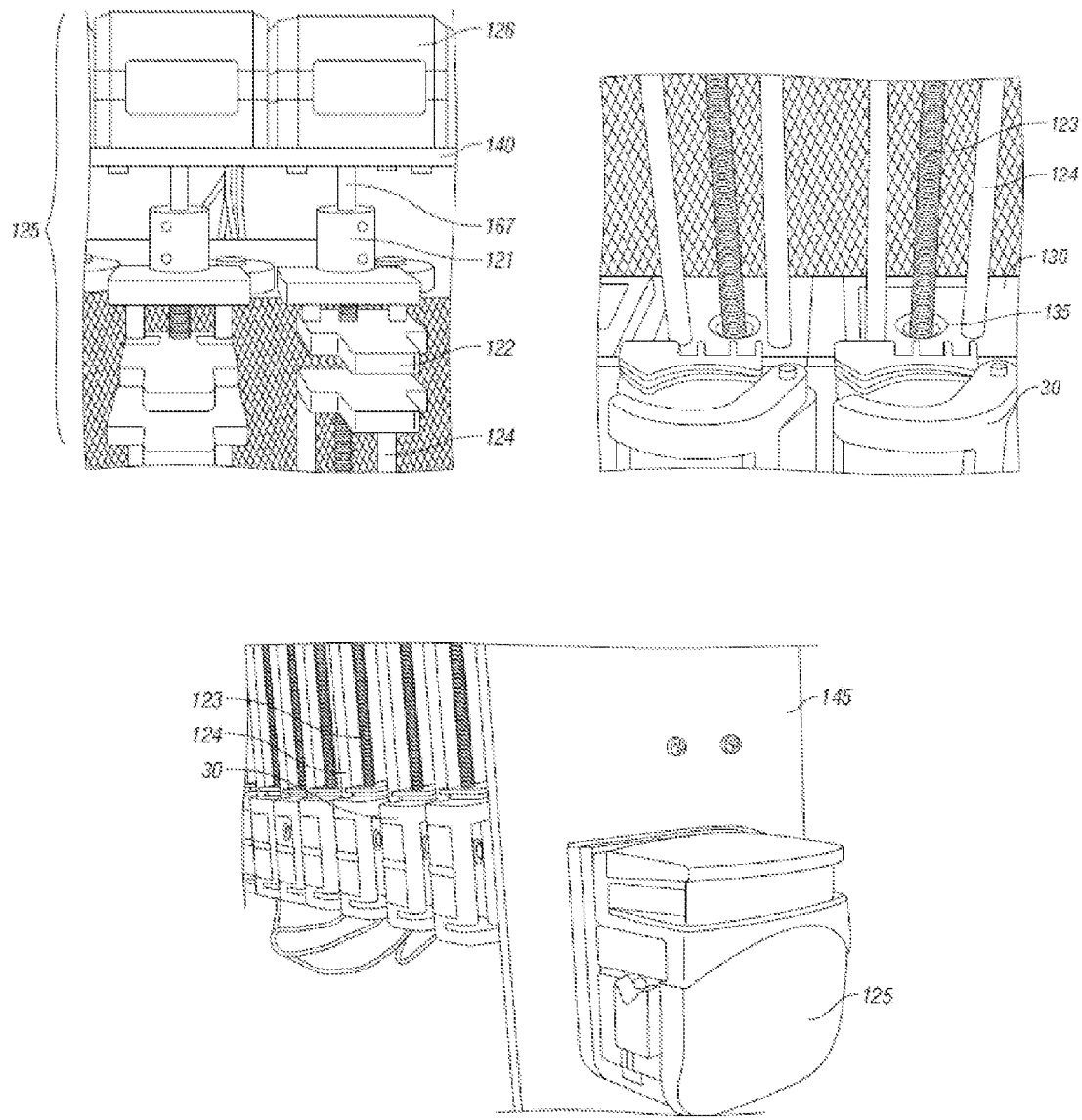
FIG. 29 is close up view of pressuring exerting devices and fluid cartridge holders attached to a structural housing.

FIG. 29 shows close-up views of components comprising a pressuring modifying device 125, fluid cartridge holders 30 attached to bearing plate 130, and pressure modifying device 125 for use an exit portal comprising tubing. Structural housing 95 comprises a pressuring modifying device 125, comprising a motor 126, motor shaft 167, coupler 121, an elongated vertically orientated screw 123, and syringe plunger driver 122.

Motor 126 turns motor shaft 167 in either a clockwise or counterclockwise direction. In a certain embodiment, motor 126 turns motor shaft 167 in a clockwise direction. In another embodiment, motor 126 turns motor shaft 167 in a counterclockwise direction. In a further embodiment, power to motor 126 can be modulated by a user using a manually powering means. Examples of manually powering means include: flipping a switch, pressing a button, turning a knob, or the like. In yet a further embodiment, power to motor 126 can be modulated by a computer connected to motor 126. In another embodiment, power to motor 126 can be modulated by a user entering commands on a user interface that is connected to motor 126 through a computer. Motor 126 may be connected to a computer by a direct connection, through a wireless connection, or through a remote connection. In another embodiment, motor 126 is covered with nonporous material, such as metal or plastic, to prevent liquid from coming in contact with the motor 126.

Motor shaft 167 is connected to an elongated and vertically orientated screw 123 through coupler 121, so that screw 123 turns when motor shaft 167 is turned by motor 126. Coupler 121 may be reversibly attached to motor shaft 167 and screw 123 by using a fastening means disclosed herein. In a certain embodiment screw 123 spins freely one or more bearings 135, wherein bearings 135 are reversibly attached to bearing plate 130. Bearing plate 130 may further comprise a plurality of attached fluid cartridge holders 30 through a fastening means disclosed herein. In a certain embodiment, a plurality of attached fluid cartridge holders 30 are attached to the bearing plate 130 so as to abut the front face of bearing plate 130. In a preferred embodiment, syringe plunger drivers 122 are vertically orientated with fluid cartridge holder 30 so as to provide positive pressure to a removable fluid cartridge 45 (not shown), when the removable fluid cartridge is placed in fluid cartridge holder 30. In yet another embodiment, the syringe plunger driver 122 can move in a vertical direction, so that syringe plunger driver 122 can travel from the bottom of motor plate 140 to the top of bearing plate 130. In a certain embodiment when syringe plunger driver 122 is moved to the top of bearing plate 130 the distance from syringe plunger driver 122 to the bottom of cartridge holder 30 is about 10 cm.

In a certain embodiment, an exit portal may comprise tubing. In a further embodiment, an exit portal comprising tubing may further comprise a pressure modifying device 125. In a preferred embodiment, the pressure modifying device 125, such as a peristaltic pump, can exert in-line tubing pressure so that fluid is pressureably moved from the fluid channel 15 (not shown) and out the distal end of the exit portal.

Figure 30:
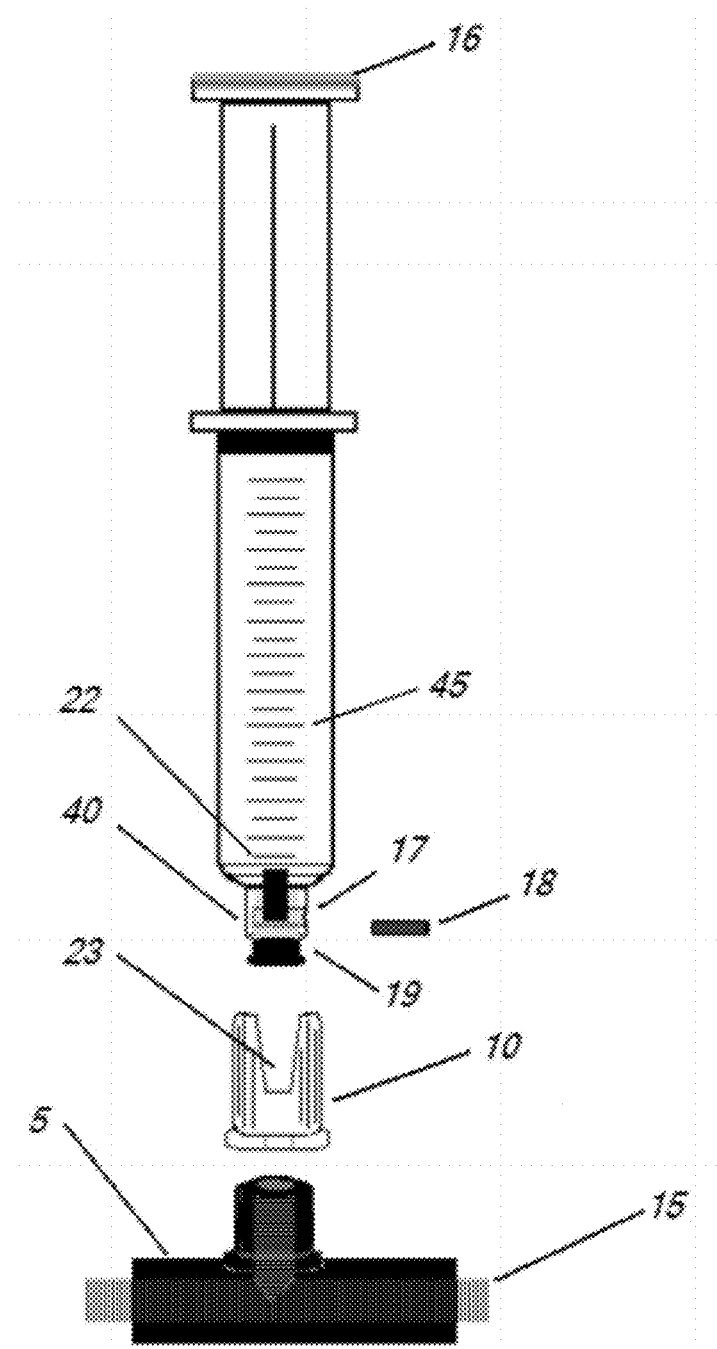
FIG. 30 is a frontal view of removable fluid cartridge, fluid cartridge carrier, and elongate member.

FIG. 30 presents a head-on view of a certain embodiment of the disclosure of a removable fluid cartridge 45, a cartridge adapter 10 and an elongate member 5. Removable fluid cartridge 45 further comprises a conductive cap 16 located on the top face of removable fluid cartridge 45. Conductive cap 16 can be made of any conductive material. In a preferred embodiment, conductive cap 16 is made of metal.

In a preferred embodiment, removable fluid cartridge 45 is a syringe. In another embodiment, removable fluid cartridge 45 is a syringe, wherein on top of the syringe plunger further comprises a conductive cap 16. In a further embodiment, removable fluid cartridge 45 is a syringe that comprises an optimized cylinder size disclosed herein. In a certain embodiment removable fluid cartridge 45 is a syringe that has a male type nozzle 35. In a particular embodiment, removable fluid cartridge 45 is a syringe with a male type nozzle 35 that further comprises a sleeve 40. In a particular embodiment, sleeve 40 is a luer lock. In another embodiment, a syringe locking hole 17 is made in male type nozzle 35 and sleeve 40, so that dispensing lock 18 can be removeably inserted. In a certain embodiment, dispensing lock 18 is a solenoid. In another embodiment, sleeve 40 may further comprise an orienting notch projection 22 which is so dimension as to fit within an orienting notch depression 23 of a fluid cartridge adapter 10. In a certain embodiment, orienting notch depression 23 has a funnel shape so as to slideably position an orienting notch projection 22 so that a removable fluid cartridge 45 ejection port 46 (not shown) is contiguous with cartridge adapter channel 55 (not shown). In a further embodiment, male type nozzle 35 may further comprise a removeably insertable hollow syringe adapter 19. Syringe adapter 19 may be comprised of any material. In a certain embodiment, syringe adapter 19 is comprised of plastic. In a further embodiment, syringe adapter 19 is comprised of rubber. In yet a further embodiment, syringe adapter 19 can fit snugly around a male nozzle 35 so as prevent leakage of fluid from syringe locking hole 17. Syringe adapter 19 is so dimensioned as to fit snugly around cartridge adapter channel 55, such that ejection port 46 is contiguous with cartridge adapter channel 55.

In another embodiment, an elongate member 5 comprising a fluid channel 15, has a plurality of raised hollow projections, such as nozzles or tips, that are so dimensioned so that the elongate member 5 hollow projections can slideably insert into cartridge adapter 10, such that cartridge adapter channel 55 is fluidly connected to fluid channel 15.

Figure 31:
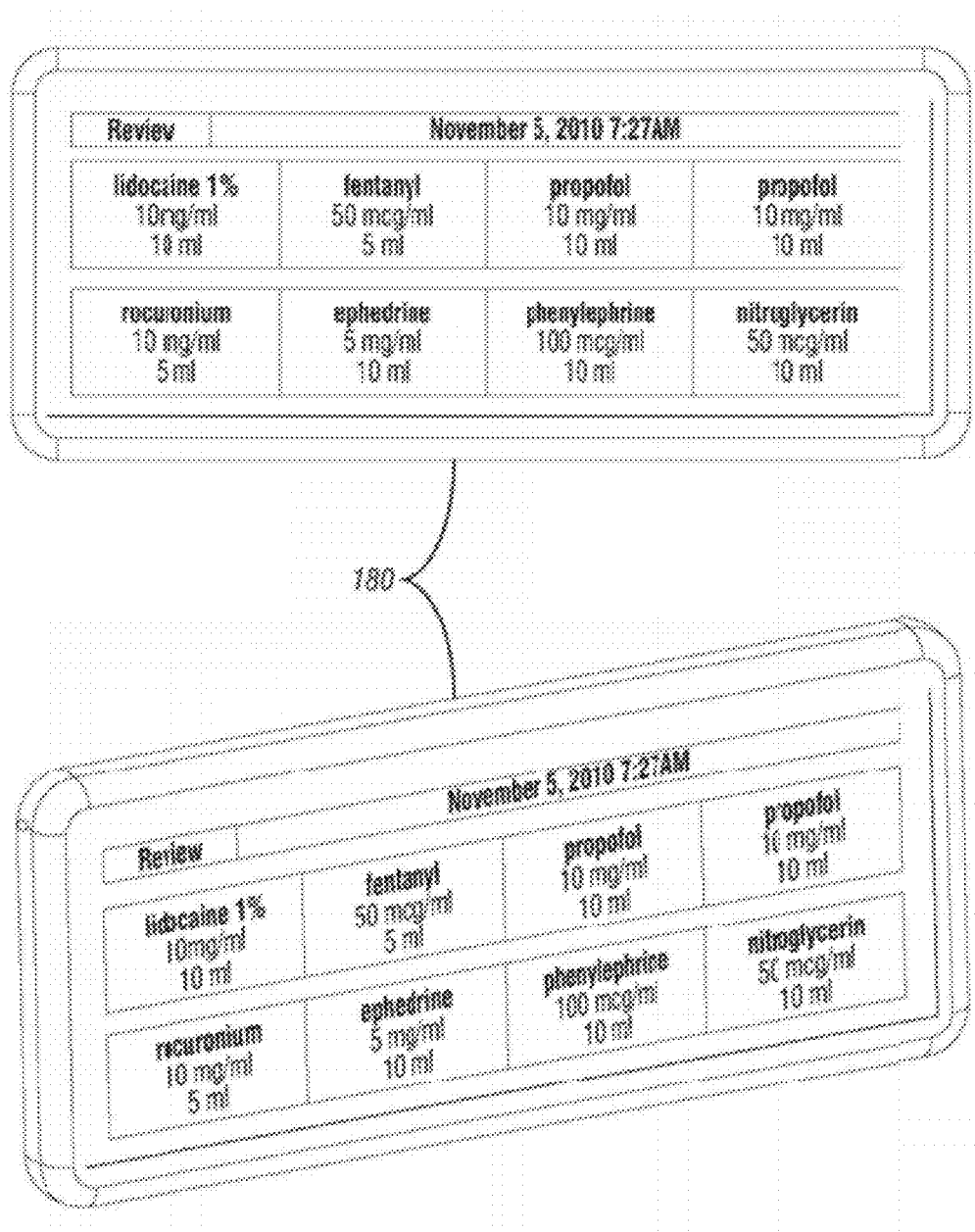
FIG. 31 is a frontal view of a control panel of a computer operably connected to a fluid delivery device in order to regulate and monitor the administration of the fluids.

FIG. 31 presents a frontal view of an embodiment of the disclosure of a control panel of a computer 180 operably connected to a fluid delivery device of the disclosure to regulate and monitor the administration of the fluids from removable fluid cartridges 45 (not shown).

Figure 32:
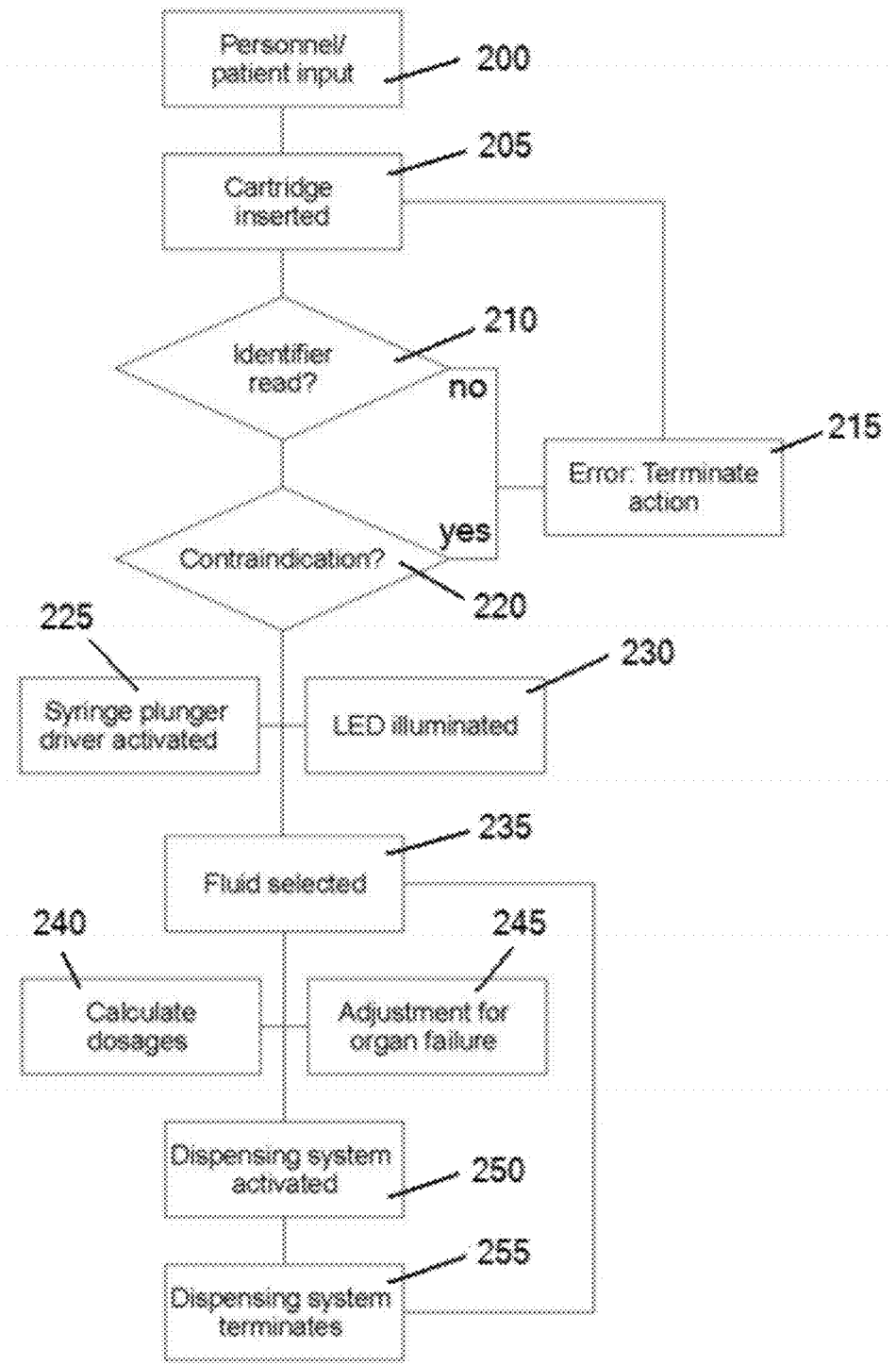
FIG. 32 is a flowchart diagram showing an exemplary process of the disclosure.

FIG. 32 presents a flowchart diagram of an embodiment of the processing methods of the disclosure. A user is prompted to input personnel and patient identifying information 200 into a user interface attached to a computer, such as names, ID numbers, patient medical history, patient vital statistics, patient weight, drug indications, etc. A removable fluid cartridge 45 (not shown) is then inserted into the fluid delivery device of the disclosure, wherein one or more machine readable indicators 48 (not shown) is then read by one or more detectors 36 (not shown) which then outputs 210 the information from reading the machine readable indicator to a computer 180. Computer 180 then processes 215 the detector outputted information by comparing the detector outputted information against a database which provides a listing of contraindications based on the inputted 200 patient's medical record. If the detector 36 (not shown) cannot read the machine readable indicator 48 (not shown) on the inserted removable fluid cartridge 45 (not shown) then the fluid delivery device is deactivated and an error message is indicated 220. If the detector outputted information is processed 215 by the computer 180 (not shown) and found to match a database entry that is identified as contraindication based on the patient's inputted medical record 200 then the fluid delivery device is deactivated and an error message is indicated 220. If the identifier is read by the detector and the fluid to be delivered is not a contraindication then the syringe plunger driver is activated 225 and LED indicator light is illuminated 230.

A user then selects 235 that the fluid is to be administered using a user entered command on the user interface, wherein the computer then calculates the dose 240 based on the information outputted by the detector 210 and the information inputted about the patient 200, wherein the computer adjusts the dose if the user inputted that the patient has organ failure 245. Upon confirming the dose by the user, the dispensing system is activated 250 and the syringe plunger driver 122 (not shown) exerts positive pressure on the removable fluid cartridge 45 (not shown) so as to force fluid from the removable fluid cartridge 45 out the ejection port 46 (not shown) and into fluid channel 15 (not shown), wherein the fluid is expelled out the fluid channel 15 (not shown) to the exit portal where the fluid is administered to the patient. The syringe plunger driver 122 (not shown) continues to exert positive pressure on the removable fluid cartridge 45 until the calculated dosage is reached, at which the dispensing system terminates 255, and then prompts the user to select 235 what fluid to deliver. If the user enters a command on a user interface that no more fluid is to be delivered then the syringe plunger driver is deactivated and any illuminated LEDs are turn off, and the processing terminates.

Various general purpose machines may be used with programs written in accordance with the teachings herein, or it may be more convenient to construct more specialized apparatus to perform the operations. However, preferably the embodiment is implemented in one or more computer programs executing on programmable systems each comprising at least on processor, at least one data storage system (including volatile and non-volatile memory and/or storage elements), at least one input device, and at least one output device. The program is executed on the processor to perform the functions described herein.

Each such program may be implemented in any desired computer language (including machine, assembly, high level procedural, or object oriented programming languages) to communicate with a computer system. In any case, the language may be a compiled or interpreted language. The computer program will typically be stored on a storage media or device (e.g., ROM, CD-ROM, or magnetic or optical media) readable by a general or special purpose programmable computer, for configuring and operating the computer when the storage media or device is read by the computer to perform the procedures described herein. The system may also be considered to be implemented as a computer-readable storage medium, configured with a computer program, where the storage medium so configured causes a computer to operate in a specific and predefined manner to perform the functions described herein.

An exemplary fluid delivery device of the disclosure, comprises a fluid delivery device is comprised of an elongate member comprising a plurality of fluid cartridge adapters, wherein each fluid cartridge adapter further comprises a one-way valve which prevents fluid from flowing into a removable fluid cartridge ejection port from the fluid channel; a fluid channel that is enclosed within the elongate member and in fluidly contact with each fluid cartridge adapter, and where one end of the fluid channel is enclosed in the elongate member and the other end is connected to an exit portal; one or more removable pre-filled fluid cartridges that comprise an exit portal located centrally on the lower face, and a machine readable indicator located on the rear face; one or more pressure modifying devices that can exert positive pressure on the fluid contained in a removable fluid cartridge; one or more detectors located behind each fluid cartridge adapter and positioned to read the machine readable indicator present on the rear face of a removable fluid cartridge once a removable fluid cartridge is inserted into a fluid cartridge adapter, wherein the detector can then output information provided on the machine readable indicator to a computer; a computer that can receive the output from the detector and then present information related to the detector's output on a display, wherein the computer may also be connected directly, wirelessly, or remotely to one or more pressure modifying devices, and/or one way valves to control the flow of pressure each removable fluid cartridge receives, control the amount of fluid that is released in the fluid channel, control the amount of fluid that is released into the exit portal, and/or be connected to and can present information from one or more information storage devices; and/or a user interface capable of entering user defined commands to a computer to control the flow of pressure each removable fluid cartridge receives, control the amount of fluid that is released in the fluid channel, control the amount of fluid that is released into the exit portal, and/or connect to and can present information from one or more information storage devices.

A further exemplary fluid delivery device of the disclosure, comprises a fluid delivery device is comprised of an elongate member comprising a plurality of fluid cartridge adapters, wherein each fluid cartridge adapter further comprises a one-way valve which prevents fluid from flowing into a removable fluid cartridge ejection port from the fluid channel; a fluid channel that is enclosed within the elongate member and in fluidly contact with each fluid cartridge adapter, and where one end of the fluid channel is enclosed in the elongate member and the other end is connected to an exit portal; one or more removable pre-filled fluid cartridges that comprise an exit portal located centrally on the lower face, and a machine readable indicator located on the rear face; one or more pressure modifying devices that can exert positive pressure on the fluid contained in a removable fluid cartridge; one or more detectors located behind each fluid cartridge adapter and positioned to read the machine readable indicator present on the rear face of a removable fluid cartridge once a removable fluid cartridge is inserted into a fluid cartridge adapter, wherein the detector can then output information provided on the machine readable indicator to a computer; a computer that can receive the output from the detector and then present information related to the detector's output on a display, wherein the computer may also be connected directly, wirelessly, or remotely to one or more pressure modifying devices, and/or one way valves to control the flow of pressure each removable fluid cartridge receives, control the amount of fluid that is released in the fluid channel, control the amount of fluid that is released into the exit portal, and/or be connected to and can present information from one or more information storage devices; a user interface capable of entering user defined commands to a computer to control the flow of pressure each removable fluid cartridge receives, control the amount of fluid that is released in the fluid channel, control the amount of fluid that is released into the exit portal, and/or connect to and can present information from one or more information storage devices; and/or a structural housing comprising end supports one or more bearing plates and one or more motor mount plates.

In an exemplary fluid delivery device of the disclosure, the fluid delivery device is comprised of an elongate member comprising a plurality of fluid cartridge adapters, wherein each fluid cartridge adapter further comprises a one-way valve which prevents fluid from flowing into a removable fluid cartridge ejection port from the fluid channel; a fluid channel that is enclosed within the elongate member and in fluidly contact with each fluid cartridge adapter, and where one end of the fluid channel is enclosed in the elongate member and the other end is connected to an exit portal; one or more removable pre-filled fluid cartridges that comprise an exit portal located centrally on the lower face, and a machine readable indicator located on the rear face; one or more pressure modifying devices that can exert positive pressure on the fluid contained in a removable fluid cartridge; one or more detectors located behind each fluid cartridge adapter and positioned to read the machine readable indicator present on the rear face of a removable fluid cartridge once a removable fluid cartridge is inserted into a fluid cartridge adapter, wherein the detector can then output information provided on the machine readable indicator to a computer; a computer that can receive the output from the detector and then present information related to the detector's output on a display, wherein the computer may also be connected directly, wirelessly, or remotely to one or more pressure modifying devices, and/or one way valves to control the flow of pressure each removable fluid cartridge receives, control the amount of fluid that is released in the fluid channel, control the amount of fluid that is released into the exit portal, and/or be connected to and can present information from one or more information storage devices; and a user interface capable of entering user defined commands to a computer to control the flow of pressure each removable fluid cartridge receives, control the amount of fluid that is released in the fluid channel, control the amount of fluid that is released into the exit portal, and/or connect to and can present information from one or more information storage devices; a structural housing comprising end supports one or more bearing plates and one or more motor mount plates; a plurality of fluid cartridge holders that are comprised of a fixed portion and a hingeably attached portion, wherein the hingeably attached portion can be attached and detached from the fixed portion of the holder, so that the hingeably attached portion of a cartridge holder can swing out in a bay door-like manner to allow the insertion of a removable fluid cartridge; and/or a dispensing tank comprising a container which can hold up to 1 liter of fluid that has a dispensing tank ejection portal located on the bottom face that is fluidly in contact with the fluid channel or exit portal by tubing, wherein the tubing further comprises an in-line pressure modifying device, such as a peristaltic pump.

In an exemplary fluid delivery device of the disclosure, the fluid delivery device is comprised of an elongate member comprising a plurality, such as eight, fluid cartridge adapters, wherein each fluid cartridge adapter further comprises a one-way valve which prevents fluid from flowing into a removable fluid cartridge ejection port from the fluid channel; a fluid channel that is enclosed within the elongate member and in fluidly contact with each fluid cartridge adapter, and where one end of the fluid channel is enclosed in the elongate member and the other end is connected to an exit portal; one or more removable pre-filled syringes further comprising a machine readable indicator located on the rear face of the syringe; one or more pumps, such as syringe pumps, that can exert positive pressure on the fluid contained in the syringes; one or more detectors, such as a camera, located behind each fluid cartridge adapter and positioned to read the machine readable indicator, such as a QR code, present on the rear face of the syringe once a syringe is inserted into a fluid cartridge adapter, wherein the detector can then output information provided on the machine readable indicator to a computer; a computer that can receive the output from the detector, such as a camera, and then present information related to the detector's output on a display, wherein the computer may also be connected directly, wirelessly, or remotely to one or more pressure modifying devices, and/or one way valves to control the flow of pressure each removable fluid cartridge receives, control the amount of fluid that is released in the fluid channel, control the amount of fluid that is released into the exit portal, and/or be connected to and can present information from one or more information storage devices; and a user interface capable of entering user defined commands to a computer to control the flow of pressure each syringe receives, control the amount of fluid that is released in the fluid channel, control the amount of fluid that is released into the exit portal, and/or connect to and can present information from one or more information storage devices; a structural housing comprising end supports one or more bearing plates and one or more motor mount plates; a plurality of fluid cartridge holders that are comprised of a fixed portion and a hingeably attached portion, wherein the hingeably attached portion can be attached and detached from the fixed portion of the holder, so that the hingeably attached portion of a cartridge holder can swing out in a bay door-like manner to allow the insertion of a syringe; and/or a dispensing tank comprising a container which can hold up to 1, 2, 3, 4, or 5 liters of fluid that has a dispensing tank ejection portal located on the bottom face that is fluidly in contact with the fluid channel or exit portal by tubing, wherein the tubing further comprises an in-line pressure modifying device, such as a peristaltic pump.

In a further embodiment, a plurality of fluid cartridge adapters are caps that have a centrally orientated hollow post and side walls, such that a luer lock, or similar structure, of a syringe can slideably insert around the post while the ejection port of the syringe can slideably insert into the hole in the post, and wherein once the syringe is inserted into the fluid cartridge adapter it will remain in a substantially upright position. In yet a further embodiment, a cap-based fluid cartridge adapter can slideably attach onto a hollow projection of an elongate member.

In another embodiment, a structural housing is comprised of end supports, where a motor mount plate has been attached using a fastening means to an upper portion of the end supports, where a plurality, such as eight, motors have been attached in series using a fastening means across the length of the motor mount plate. In a further embodiment, a structural housing further comprises one or more bearing plates comprising bearings that allow for a central vertically-orientated elongated screw to spin freely within the one or more bearings, and wherein the elongated screw can be attached to a motor. In yet another embodiment, one or more cartridge holders can be attached using a fastening means to one or more bearing plates. In yet another embodiment, a structural housing further comprises one or more support rods that are located an equal distance from a vertically-orientated elongated screw, and wherein the support rods can be attached to a motor mount plate and a bearing plate using a fastening means. In yet another embodiment, a structural housing further comprises one or more syringe plunger drivers that can slide freely vertically up and down the support rods but cannot move horizontally away from the support rods, wherein the syringe plunger drivers can be reversibly attached to a vertically-orientated elongated screw, such that when the syringe plunger driver is attached and the screw is rotated around a fixed horizontal axis the syringe plunger driver controllable moves in a upward or downward fashion depending on whether the screw is rotating clockwise or counterclockwise. In a further embodiment, a structural housing further comprises a substantially box-like structure located on the rear portion of the structural housing, wherein one or more wires can be substantially inserted into the box-like structure and where at least a portion of the box-like structure can be removed to provide access to the interior portion of the box-like structure.

The disclosure provides for a fluid delivery device comprising one or more pressure modifying devices, such as syringe or stepper pumps, that can be controlled by a computer comprising a user interface, such as a touchscreen, such that by the user entering commands into the user interface, can control the operation of the fluid delivery device. The fluid delivery device of the disclosure can therefore automate several tasks that are normally performed manually by a health care professional. For example, to prepare medication for administration, a syringe is placed into one of fluid cartridge holders of the device, and a machine readable code, such as a QR code, is detected by a detector, such as an on-board camera, that then calls up the identifying code (CAS, ATC, PubChem, ChemSpider, UNII, KEGG, ChEBI, ChEMBL) in a database. The name of the drug and other characteristics such as the concentration, volume, size of the syringe, expiration date, and lot number are identified and this information is then outputted to an attached computer to display to a user. In a certain embodiment, the machine readable code is located on the rear face of a syringe, and a detector is located so as to detect the machine readable code. In a further embodiment, a plurality of detectors is used to identify a plurality of machine readable codes. In an alternate embodiment, a single detector is used to identify a plurality of machine readable codes.

The automation of this process eliminates the need to manually scan the syringe with a handheld bar code reader or manually program the pump, thereby streamlining the process and eliminating human induced errors. Additionally, the recognition of removable fluid cartridge, such as a syringe, allows automation of other processes such as charting in the electronic medical record, billing insurance, and managing the supply chain. At the same time the drug information is displayed on a monitor or touchscreen, LED lights below or behind the syringe are illuminated when the syringe is inserted. The lights illumination can be intensified to indicate when medication is administered by the device to help the medical provider visually confirm the name of the medication and the graduations on the syringe. Additionally, the device using voice information technology 'speaks' the name of the medication, providing additional auditory confirmation of the medication as it is being delivered.

In a certain embodiment, once the machine readable code, such as a QR code, is detected by the detector, the motors of a syringe pump activate and then turn a lead screw to lower a syringe plunger driver onto a syringe plunger of a syringe. In another embodiment, the syringe pump motor or stepper motor is turned off by a physical switch created by the top of the syringe plunger driver and the syringe. In alternate embodiment, the top of the syringe plunger is topped by a conductive metal which shorts lead wires to turn off the stepper motor or syringe motor when the syringe plunger driver is activated when the syringe is placed into a fluid cartridge holder and makes contact with the top of the syringe plunger. The accuracy of the syringe pump is increased by decreasing the dead space created by a gap between the syringe plunger driver and the syringe plunger. In yet another embodiment, a fluid delivery device further comprises an encoder on the syringe pump motor, wherein the encoder knows the position of the syringe plunger driver in relation to the syringe plunger, and stops the motor as the syringe plunger driver is positioned on top of the syringe pump.

In a particular embodiment, a computer comprising a user interface can display vital information required for user-control of the system including visual indication of battery life and status of wireless communication. In another embodiment, a computer comprising a user interface can integrate one or more global positioning system location sensors of the hospital to prevent inadvertent administration of medication not indicated by the patient's physical location. For example, paralytic drugs used to induce muscle relaxation such as succinylcholine is used to facilitate tracheal intubation in the operating room under controlled circumstances. This medication arrests spontaneous respiration of the patient and if given in the preoperative area inadvertently could lead to hypoxia and eventually death, if left unrecognized.

In a particular embodiment, a computer comprising a user interface, can record physical characteristics of the patient such as height and actual body weight to compute ideal body weight, (Broca, Devine, Robinson, Miller, or Hamwi formula) and body surface area (Dubois and Dubois, Mosteller, Haycock, Gehan and George, Boyd, Fujimoto, Takahira, or Schlich formula), which the computer can then process using algorithms, and then present the results of the calculations on a display so that medication can be accurately dosed based on a patient physical characteristics and then delivered by a fluid delivery device disclosed herein. In another embodiment, a computer comprising a user interface can also process laboratory values such as plasma creatinine to calculate the Cockcroft-Gault or Schwartz formula to provide an appropriate dose of medication by a fluid deliver device disclosed herein, should the patient be in renal failure. In another embodiment, the advantages of using a computer comprising a user interface in concert with a fluid delivery device disclosed herein, allows for an accurate and fast determination of an appropriate dosage of medication and immediate delivery of that dosage by a fluid delivery device disclosed herein. The medication dosages are defaulted to the lowest acceptable dose avoiding potential complications for inadvertently administered medication by the user.

In a further embodiment, a computer comprising a user interface also integrates electronic timers to automatically re-dose medication using a fluid delivery device herein, such as antibiotics at a user specified time, thereby avoiding missed medications, or errors of omission. In another embodiment, a computer comprising a user interface that is connected to a delivery device disclosed herein can further comprise a database program which guards against medication contraindications such as black box warnings, patient's disease states, incompatible medications, and pregnancy and lactation status and warns of expected side effects, wherein the database program and/or calculated dosage by the computer is then used to timely notify the user when a fluid delivery device disclosed herein needs a syringe to be refilled.

In a particular embodiment, an elongate member further comprises fluid cartridge adapters that are adapted to receive syringes, wherein these adapters are comprised of a cap that accommodates syringes that are 3 to 60 mL in volume.

The notch #75 in the syringe cap #30 should not simply be a linear cut through the cap as drawn. Instead, it should be funnel shaped opening at the top with a wide opening to accommodate the pin on the syringe. This is done so that even if the syringe is misaligned as it is placed into syringe cap #30, the funnel shape will guide the syringe into its correct position. In another embodiment, the removable fluid container is a syringe, wherein the surface area of the syringe is minimized in comparison to syringes of similar holding capacities. In yet another embodiment, the removable fluid container is a 20 ml syringe, wherein the surface area of the 20 ml syringe is minimized in comparison to standard 20 ml syringes. In a further embodiment, the dimension of the cylinder of the 20 ml syringe is about 1.47 cm in radius, and about 2.94 cm height. In a particular embodiment, the removable fluid container is a 60 ml syringe, wherein the surface area of the 60 ml syringe is minimized in comparison to standard 60 ml syringes. In another embodiment, the dimension of the cylinder of the 60 ml syringe has radius of about 2.12 cm and height of about 4.24 cm. In a particular, embodiment, the removable fluid cartridge is a syringe in which the top of the plunger is capped with a conductive material, such as metal. In a certain embodiment, a standard syringe can be modified by making a hole in the neck and inserting a solenoid lock, wherein the solenoid lock secures the syringe to the fluid delivery device to prevent stealing of medication. In an alternate embodiment, a standard syringe can be modified by linear cutting the neck and inserting a solenoid lock. In a further embodiment, a solenoid lock engages on the neck of the syringe to fluid cartridge adapter to prevent unauthorized tampering or theft of high-value medications such as narcotics. In yet a further embodiment, a standard syringe can be modified by making a keyed notch of the neck, such that the syringe can only be placed into a fluid cartridge adapter in the direction wherein a notched projection fits the keyed notch on the neck of the syringe. In another embodiment, the keyed notch projection on the neck of the syringe, fits into a funnel shaped notch depression, so that if the syringe is misaligned as it is placed into the fluid cartridge adapter, the funnel shape of the notch depression will guide the syringe into its correct position. In a particular embodiment, the standard syringe is modified by making a keyed notch in the front surface of the syringe.

In further embodiment, the fluid cartridge adapters further comprise one way valves, such that the valves allow fluid to enter the fluid channel when under pressure but do not allow fluid to enter a syringe.

In a further embodiment, the exit portal comprised of tubing is further comprised of an inline pressure modifying device, such as a peristaltic pump, so that during bolus infusion, the pressure modifying device is activated to flush the administered medication directly to the patient, thereby eliminating medication contained within the line and potentially a delay of administering medication. In another embodiment, a fluid delivery device disclosed herein further comprises an array of sensors that is connected to an alarm, wherein the array of sensors monitors fluid pressure in the exit portal to prevent the delivery of medication should the intravenous catheter become misplaced outside of the blood vessel or air in the line to prevent an air embolus.

In a certain embodiment, a computer comprising a user interface can be connected to a fluid delivery device disclosed herein via wireless communications, such as Bluetooth, Wi-Fi, ZigBee, among others. In a preferred embodiment, a computer comprising a user interface is connected via wired connection to avoid loss of power from sudden premature battery failure or dropping tablet, thereby potentially rendering the device inoperable. In another embodiment, a computer comprising a user interface that is connected to a fluid delivery device herein is secured by a flexible gooseneck arm and can be angled in multiple positions to conform to the user's preference. The software of the tablet can be updated via wireless communications to integrate complementary applications such as text/voice paging, personnel and equipment location, perioperative vital sign monitoring, among others.

The disclosure also provides for a robotically controlled fluid delivery device. For example, in a variation to the design, the elongate member can also be made to move in three dimensions beginning with an x-axis and y-axis to select removable fluid cartridges aligned in rows and columns as well as a z-axis to move the elongate member to the ejection port of one or more removable fluid cartridges. Alternatively, the plurality of removable fluid cartridges can be mobile relative to a non-mobile elongate member. In this design, the removable fluid cartridges would be mounted on a rail which would allow movement along an x-, y-, and z directions along a rail. The elongate member below can be stationary. After aligning the ejection port of the appropriate removable fluid cartridge above the elongate member, the structural housing containing a plurality of removable fluid cartridges can then be lowered to connect with fluid cartridge adapters of the elongate member.

In a particular embodiment, one of the panels of a structural housing, preferably the front, contains a dovetailed design to correct the position of the elongate member should it become misaligned while it is moving upwards along the z axis. When the elongate member moves up and is not properly aligned, the triangular design of the dovetails can guide the fluid cartridge adapters of the elongate member up to the ejection port of a removable fluid cartridge.

In a certain embodiment, the elongate member can be attached to solenoids, a stepper motor, or similar device that can raise the elongate member upwards to sample fluids from the removable fluid cartridges. An ejection port, typically located at the bottom of the cartridge, fits into fluid cartridge adapter of the elongate member to allow fluids to be transferred from a plurality of cartridges into a common exit portal. In a particular embodiment, an ejection port of a removable fluid cartridge can form a hermetic seal with a fluid cartridge adapter to prevent any unwanted leakage.

It should be understood, that disclosure provides not only for removable fluid cartridges that can be used with a device disclosed herein, but also for removable fluid cartridges that can be used with alternative devices. In a certain embodiment, the disclosure provides for a dual fluid cartridge system comprised of a removable fluid cartridge and a self-contained pump dispensing cartridge. In another embodiment, the disclosure provides for a dual fluid cartridge system wherein removable fluid cartridge is prefilled with a fluid and sits on top of the self-contained pump dispensing cartridge. Examples of fluids include, but are not limited to, gases and liquids, such as syrups, solutions, mixtures, chemicals in a liquid state, oils, solvents, suspensions, and any combination of the foregoing. In an alternate embodiment, the disclosure provides for a dual fluid cartridge system comprising one or more features selected from the group of: a deformable input one-way valve, a deformable output one-way valve, an ejection port, a diaphragm, a dispensing port, an air relief vent, a machine readable indicator, a label, and a pierceable port.

In a particular embodiment, the disclosure provides for a self-contained pump dispensing cartridge that comprises a diaphragm that is made of a magnetic material or a magnetic material that further comprises an attached magnet, such that when a controllable electromagnetic field generated by the flow of electricity through an electromagnetic coil can alternate between attraction and repulsion on a magnet can be used to pull the diaphragm outward and push the diaphragm inward, respectively. A magnetized diaphragm or magnet attached to the diaphragm reciprocates in an inward and outward direction during the activation of an external, single electromagnetic coil to deform and thereby pump fluid out the ejection port. During each cycle, a fixed amount of fluid is brought into a cavity between a one-way input and an output valve by generating negative pressure by an electromagnet attracting, or pulling, on a magnetized diaphragm or magnet attached to the diaphragm, thereby flexing it. This magnetic element is actuated by an external electromagnetic coil by electricity energizing the electromagnet coil and generates an electromagnetic force. An internal input one-way valve opens when fluid is suctioned into the cavity of the dispensing chamber. Fluid is pumped out from nozzle when the electromagnet repels the magnetized diaphragm or magnet attached to diaphragm, opening the output valve, as the fluid flows out from it and closing the internal input valve to prevent the backflow of fluid into the reservoir. The pump diaphragm can be made of any magnetic material. In a certain embodiment, the pump diaphragm is comprised of stainless steel, such grade particularly useful for the pharmaceutical industry like SS 316 grade. In general, the amount of fluid flowing into the cavity is a fixed amount and reciprocating cycles on the diaphragm will generate a sequentially larger volume of fluid. When the electromagnet coil is deenergized, the diaphragm ceases movement and the flow of fluid out of the ejection port stops. While the electromagnetic coil is continuously receiving an electrical signal, the diaphragm is in constant motion in a reciprocating fashion to alternatively create positive pressure, or dispensing fluid, or negative pressure, or suctioning fluid into the dispensing chamber.

In another embodiment, a diaphragm is made of a flexible non porous material, wherein the diaphragm can be physically pushed inward and physically pulled outward by using any physical means. Examples of a physical means, include, any structural part that can be moved up and down in a piston-like motion by using a motor.

In a particular embodiment, the disclosure provides for a dual fluid cartridge system comprising a self-contained pump dispensing cartridge and a removable fluid cartridge comprising an air relief port, wherein the self-contained pump of the dispensing cartridge can operate in a continuous fashion. The fluid pumped out of a self-contained dispensing cartridge is replaced by fluid available within the removable fluid cartridge. The vacuum which would otherwise collect on the top of the removable fluid cartridge is broken by an air relief port which is connected to the atmosphere by the side of the dispensing chamber to the inside of the reservoir. In this way, the pressure inside the reservoir is equal to the ambient pressure thereby allowing the pump to self-prime and operate continuously. This air relief port may be sealed upon shipment of the removable fluid cartridge to prevent leaking. Accordingly, the removable fluid cartridge can be then be activated by piercing the seal covering the air relief port. In a certain embodiment, the air relief port can be connected either to the atmosphere, to pressurized gas, or to a pressure modifying device.

In a particular embodiment, the disclosure provides for removable fluid cartridges further comprising a pierceable port. In a certain embodiment, the pierceable port is located on one of the accessible faces of the cartridge. Generally, the pierceable port should be located so as to facilitate access to the fluid in the cartridge for the purposes of mixing or withdrawing fluids inside.

In a particular embodiment, the disclosure provides for a removable fluid cartridge that further comprises one or more machine readable indicators. In a certain embodiment, the disclosure provides for one or more machine readable indicators comprising a microchip. In a further embodiment the microchip is comprised of a printed circuit board, and a transmitter. In yet a further embodiment, the microchip can communicate with a computer that has an attached or wireless device to receive the microchip's transmissions. In another embodiment, the microchip transmits read only information about the liquid in a removable liquid cartridge. Examples of such information, include: identifying the liquid, the status with respect to sterility of the liquid, the concentration of the liquid, volume of the liquid, lot number, dosage instructions, expiration date, drug indication warnings, data to facilitate supply chain management, expenses, and billing. In a further embodiment, the disclosure provides that the microchip can be reprogrammed by entering commands into a computer using a user interface. Examples of reprogramming include: updating and modifying the information about the contents of the cartridge.

In a particular embodiment, the disclosure provides for a self-contained pump dispensing cartridge further comprising a shaped nozzle so dimensioned as to fit into a fluid cartridge adapter. In a further embodiment, the fluid cartridge adapter is fluidly connected to a fluid channel that designed to retrieve and transmit fluid. In a certain embodiment, the self-contained pump dispensing cartridge nozzle is substantially a cone-shaped structure that closely fits into a fluid cartridge adapter. In a further embodiment, the self-contained pump dispensing cartridge nozzle fits into a fluid cartridge adapter so as to form a hermetic seal. The nozzle of each self-contained pump dispensing cartridge by fitting into fluid cartridge adapter allows the passage of fluid from the cartridge into the fluid channel and out the exit portal where the fluid can be collected or used directly. In this fashion one or more fluids can be delivered on a single or multiple functional bases to be collected or used for various applications, such as administering to a patient.

The disclosure provides for, a replacement fluid cartridge having any shape. Moreover, the disclosure provides that a replacement fluid cartridge may have a different external shape than the internal cavity which holds fluid. The shape of the internal cavity is not critical to the practice of the invention. For example the internal cavity may be rectangular or cuboid shaped. In another embodiment, the internal cavity of the removable fluid cartridge is comprised of a reservoir. The removable fluid cartridge may be attached to the self-contained pump dispensing cartridge by a number of methods. In a certain embodiment, the removable fluid cartridge is screwed onto the dispensing chamber to allow for a hermetic seal between the removable fluid cartridge and the self-contained pump dispensing cartridge. In yet another embodiment, the internal cavity of the removable fluid cartridge is further comprised of security film to prevent or indicate tampering. Examples of security films include, but are not limited to, shrink wrap, foil, or a membrane. The security film may be further customized so as to provide information regarding the fluid contained in the removable fluid cartridge. The film is, however, should be easily removed to rapidly identify tampering of the removable fluid cartridge as well as allow for disassembly of the system for reuse or recycling of individual parts once the use of the removable fluid cartridge is no longer needed.

In a further embodiment, the disclosure proves for a removable fluid cartridge comprised of an inner liner of a chemically inert material, and an outer liner of chemically inert material or non-chemically inert material. Examples of inert material which can be used include glass, cyclic olefin polymeric materials, and pharmaceutical grade plastics.

The disclosure provides for a fluid delivery device to administer metered volumes of fluids from pre-filled cartridges. While many of the embodiments recited herein are directed to using the disclosed fluid delivery device for medicine, it should be understood that the device is generally directed to the delivery of a metered volume of liquid, and as such, the device's utility can applied in any number of fields and applications. For example, a device disclosed herein can be used in industrially, such as the generation a solvent mixture; scientifically, such as the delivery of buffer or culture media; and commercially, such as creating a mixture of flavoring agents.

In the field of medicine, there has been a long felt need to develop a more efficient and less error prone methodology to deliver intravenous medications to patients. For the last 50 years, the standard method for administering intravenous drugs was by drawing medications into syringes from vials and pushing them through intravenous lines connected to patients. Even under optimal conditions, this method is prone to human error. In 2006, the Institute of Medicine conducted an investigation into drug-related errors in the United States and found that 1.5 million adverse drug events occur every year, sometimes resulting in serious or even fatal harm. It also found the primary cause of this patient injury epidemic was human error. One study calculated the economic costs of this problem in the United States to be over $2 billion in 1993, leading to longer hospitalizations, loss of income, and higher insurance premiums, which affects all Americans. In fact, 2% of all inpatient hospitalizations result in preventable drug errors and lead to an additional $4,700 per admission or roughly $2.8 million yearly for a 700-bed hospital. Other incidental costs result in disability and a less productive workforce. Of greater importance, these errors can be traced to over 7,000 American deaths during that same time period. The fluid delivery device disclosed herein solves this long felt need by significantly lowering the risk of human error and increasing efficiency, by using ready-to-use cartridges and in certain embodiments by using computer aided delivery of fluids for intravenous administration. In a preferred embodiment, the disclosure provides that the fluid delivery device disclosed herein is used in the administration of intravenous medications to patients in a hospital such as the medical wards, intensive care units, or operating rooms.

Application of technology enables medical providers to become more efficient and productive. In the operating room, anesthesia machines allow anesthetists to deliver gases to patients simply and rapidly by turning dials to change the concentration and flow of gases. Likewise, the device disclosed herein can safely and reliably deliver intravenous medications to patients. The device disclosed herein would significantly reduce medication errors caused by tired and distracted medical providers who are juggling several responsibilities at once under a high stress environment. The device of disclosure by contrast, reliably and efficiently prepares and in certain embodiments charts drugs in even the most demanding and stress filled environments. Moreover, by the device of the disclosure fulfilling this important function, it allows the medical practitioner to spend more time with the patient. It is well-known that related errors occur as a result of medical provider fatigue. Currently, most medication errors occur mainly from the use of intravenous medications. While such errors result from a number of different causes, intravenous medication errors are the leading cause of complications by anesthetists in the operating room. The device disclosed herein would rectify these medication errors, by having the most common intravenously administered medications in pre-filed cartridges that are readily available for use that can be easily inserted into the device. In a certain embodiment, the disclosure provides that once the removable fluid cartridge is inserted in the device disclosed herein, the device logs and registers the cartridge into a computer. In another embodiment, by using a user interface, such as a computerized touch-screen display, desired doses are selected by scrolling through and pushing electronic buttons to activate the dispensing system to rapidly access medication from the cartridges. An advantage of the device of the disclosure is to simplify the daily preparation of intravenous medication used during medical procedures and substantially lower the risk of human error. Another advantage of the device of the disclosure is that the device can improve work flow efficiency and in certain embodiments provide real time alerts and warnings to the user. The device disclosed herein can provide multiple safety nets by automatically alerting the medical practitioner to contraindicated medications and allergies, responding to clinical findings such as hypertension or light anesthesia, sending reminders for redosing medications, performing supply chain management, and documenting medication administration.

In no other field of medicine than anesthesia is the job of the medical provider inseparable from the delivery of medications, which are almost exclusively delivered intravenously. As such, the responsibility of both quickly and accurately delivering medications in the proper dosage is of paramount importance. Information communication problems often originate during emergencies or noisy work environments, leading to the improper administering of medications. While the administering anesthesia is perhaps safer than at any other time, this method accounts for higher rates of errors than any other route of administration. About half of all errors occur during administration, and two-thirds of these errors involve drugs which are administered intravenously. Furthermore, some medications require dilution before use, and incorrect calculations can result in a drug overdose. The current methods, therefore, provide low but significant risks that the practitioner will select the wrong medication, mislabel the medication, and/or create a dose of medication that could be potentially harmful if administered to the patient. Unfortunately, numerous reports highlight that the current methods of intravenous administration result in a small but persistent source of harmful error. All too common, errors involve the incorrect use of syringes where a medication was administered that was not intended, or at an incorrect dose. Improper labeling or failure to label syringes was another cited source of error. Sensible practice can allow for the use of unlabeled syringes, if the syringes are filled from vials and then immediately given to patients. But, unanticipated delays caused by the often furious pace in the operating room could introduce unforeseen risks. The Joint Commission on Accreditation of Healthcare Organizations (JCAHO) also recommends that medication be available in an accessible form to avoid any opportunities for error. Furthermore, many intravenous medications have the same clarity and viscosity of water and therefore are virtually indistinguishable from each other based on visual inspection. Unlabeled syringes should be discarded, but the use of unlabeled syringes was found to be disturbingly common. The disclosed device provides a solution to these problems recognized in the art, by providing an accurate and metered dose of fluid while eliminating or minimizing harmful sources of human error.

It is well known in the art that preparing intravenous medications for a case is the leading source of time expenditure for the anesthetists. Specifically, drug and fluid-related tasks comprises nearly 50% of all clinical activities during the initial set-up at the beginning of the workday in noncardiac cases and 75% of the set-up activities in cardiac cases. These tasks involve transferring medications packaged in vials into syringes first before they are readily usable in patients and priming lines and programming infusion pumps. Moreover, searching for items during a case accounts for up to 6% of all intraoperative drug and fluid tasks during noncardiac anesthesia. Accordingly, there is a long felt need in the art to streamline and make more efficient the process for creating and administering intravenous medications. The disclosed device provides a solution to these problems, by the use of prefilled removable fluid cartridges that do not require any additional processing. Moreover, in a certain embodiment, the disclosure provides for a removable fluid cartridge that has a pierceable port so that additional medication or medications can be added to the fluid in the cartridge.

After the medication is administered, documentation of the events should be placed in a medical record. Charting, however, is given a low priority by many medical professions and is sometimes overlooked or not done properly. If the anesthetist, for instance, gives a break to another person, the omission of recording the events in a chart may lead to a duplicate dose. A duplicate or failure to deliver a required dose of a medication to a patient can lead to serious and even fatal consequences. The Institute for Healthcare Improvement has found there are a significant number of medication errors resulting in adverse drug events in many institutions due to improper or failure to chart medication events. Medical facilities, especially those that operate in remote areas or nonprofit clinics, have information systems that are generally not networked to other medical institutions. Consequently, the relaying of medical information about a patient is often communicated through phone conversations, which can be inefficient.

Medical devices that are connected to information storage devices, such as a computer, are particularly well-suited for making demonstrable changes in the administering of medication, especially in light of the ever increasing amount of data gathered about patients. A computer can rapidly sort through the patient's allergies and health status such as pregnancy, renal or hepatic failure, and abnormal laboratories to avoid adverse interactions or black box warnings. While this data is available in numerous sources such as the patient's paper chart, electronic medical record, and laboratory systems, it is not presented in a format that allows for easy access or semi-automated decision-making. The device disclosed herein can be connected to a computer, through a direct, wireless or remote network, and can be further networked to other information storage devices to allow for real time information processing and presentation.

Syringe administered intravenous medications run the risk of introducing air into a vein. Air injected into venous lines can cause an air embolism which can be fatal, especially if there is a high rate of air accumulation. While most medical practitioners are fastidious about ensuring their lines are free of air, deaths have been reported. In addition, patients with an unrecognized patent foramen ovale run even higher risks of a harmful air embolism event. Moreover, children run a higher risk of a harmful air embolism event due to their smaller size. The disclosure provides for a fluid delivery device that uses a closed circuit system, whereby the inadvertent injection of air is minimized. In a further embodiment, a fluid delivery device disclosed herein is computer assisted and minimizes avoidable and harmful errors by administering metered volumes of fluids.

In a particular embodiment, the disclosure provides for a device of the disclosure that has an intuitive user interface to simplify repetitive tasks which are better suited to be performed by machines. Furthermore, in another embodiment, a device disclosed herein can be operated by a medical practitioner by using an easy to operate user interface, such as a touchscreen. Using the device of the disclosure, significantly reduces the number of manual intra-operative maneuvers, including the most error prone steps such as filling or labeling cartridges or diluting medications.

The fluid delivery device disclosed herein can confirm that a dosage is within acceptable limits by notifying a user through a user interface, such as a touchscreen. The fluid drug delivery device disclosed herein also makes it easy to adjust a medication's dosage or a fluid's concentration. All a user has to do is choose a different dosage or concentration by entering commands into a user interface connected to a computer that is connected to a fluid delivery device disclosed herein, and the fluid delivery device will carry out the user entered commands. The device of the disclosure can exploit existing capabilities of pharmacy computer software. More specifically, a device disclosed herein can adjust the amount, or rate of delivery of fluids based on user entered commands, or from data supplied on information storage devices. Consequently, the fluid delivery device disclosed herein can administer single, daily, or lifetime doses of medication containing fluids. The device disclosed herein, thereby can reduce errors caused by faulty human memory for dosing, concentrations, chemical interactions, drug to drug contraindications, allergies, adverse effects, re-dosing guidelines, and pediatric doses.

The fluid drug delivery device disclosed herein by having the capability to access information storage devices can access pertinent and important information, such as a patient's weight since this information can be integrated into electronic medical record systems. Since a common source of dosage errors is incorrect calculations based on weight, the device disclosed herein can obviate these errors, by making accurate calculations instantly. A device disclosed herein can feature autocomplete capabilities, which can calculate a range of possible drug dosages based on weight and provide recommendations through an attached user interface, based on the most common or popular dosage based on the various time intervals of the drug administering course. For instance, the device disclosed herein can predict by using an attached information storage device, an induction dosage of 100 mg of propofol for a 70 kg man without the user actually scrolling through the list of all possible dosages for propofol and limiting the possibility of making a drug dosing error that is either too low or high. Intraoperatively, the device disclosed herein may suggest a much smaller dose of propofol in the event that the patient began to wake up during surgery. A similar set of possibilities would be available for other drugs, including most notably, neuromuscular blockading drugs where the intubating and maintenance doses are different.

A device of the disclosure can also keep track of which anesthetic agents have been administered and thereby prevent further delivery by shutting off one or more valves, if dosing limits have been reached. Once these limits have been exceeded, the device disclosed herein will require the user acknowledge the amounts of medicines which have been given before opening one or more valves.

Additionally, it is difficult to assess whether a drug-filled syringe has been previously used for another patient, and this inability to keep track of each syringe prevents it from being used for another patient. The fluid drug delivery device disclosed herein can quickly determine which cartridges have or have not been dispensed. The device disclosed herein, therefore enhances the efficiency of supply chain management, inventory control, and billing. As another safety measure, cartridges with Drug Enforcement Administration scheduled drugs can contain security measures, such as locks, so that the removable fluid cartridges will not dispense unless the security measures are removed, such as entering an appropriate security code or security key.

The advantage of replacing a medical provider from mundane tasks is speed. The prompt supplying of medication can sometime spell the difference between life and death for a patient who is bradycardic, hypotensive, or arresting. Under current methods, medications are packaged in vials that are not immediately available for patient use without first being transferred into syringes. If a medical provider fumbles with these vials during the stress of an emergency, the administration of the medications could be delayed and result in adverse patient outcomes. The device disclosed herein would obviate the need for syringes, and because of which medical providers would be free to focus their attention on other tasks. Moreover, the device disclosed herein, can eliminate any number of steps from a medical provider's daily routine, including, but not limited to, sparing them from labeling concentrations, writing their initials, and indicating the date and time of when the syringe was prepared. A close look at drug preparation process reveals that there are 66 steps required to administer a single drug to a patient, and experienced providers took on average 35 seconds to do so. The number of steps involved in this as well as any other process is compounded by the rate for mistakes at each step. A device disclosed herein can perform the repetitive tasks that a medical provider would normally have to perform.

The device disclosed herein allows the medical provider to deliver lifesaving medications in seconds, and with absolute precision, via pre-filled removable fluid cartridges. Additionally, the fluid drug delivery device disclosed herein could automatically make an electronic medical record of the medication administered, concentration, and date and time when the medication was delivered. A fluid drug delivery device of the disclosure can keep a record of actions taken by the medical provider for instantaneous review during or after a case. For instance, if the medical provider needed to know if a medication was given, the medical provider could access the electronic medical record either directly, wirelessly or remotely by using a user interface, such as a touchscreen. A fluid delivery device disclosed herein could also be useful as a black box to review cases for near misses or errors.

The fluid delivery device of the disclosure will streamline case set up, turn over, and intraoperative management since it spares physicians and nurses from performing medicine transfers, labeling, charting. A fluid delivery device disclosed herein will enable skilled professionals to spend their critical time on expert work that cannot be automated. A fluid delivery device of the disclosure will also decrease waste since vials which are only designed to hold medications and syringes and needles usage for transferring medications can be replaced with pre-filled removable fluid cartridges.

A fluid delivery device disclosed herein is designed to link to other patient data systems for easy access of critical patient data as well as be able to respond to potentially dangerous clinical situations. A fluid delivery device of the disclosure can display notifications when medication or an adjustment to current dosages may be necessary by using a connected computer. For example, in response to an abrupt change in breathing over a ventilator or an out of range blood pressure measurement, a device disclosed herein can signal a warning and make recommendations of possible medications to address such a situation by calling up pre-programmed patterns or algorithms that can be recognized by the device by using an attached computer and user interface. A medical provider can then choose to act on the suggestion instantly by entering commands using a user interface connected to a computer that is network to a device of the disclosure. This functionality could potentially allow a device of the disclosure to save lives.

A device disclosed herein can also access the electronic record of each patient's medical history by being networked to one or more information storage devices. A device of the disclosure can therefor prevent tests from unnecessarily being repeated or alternatively identify studies which need to be performed. A device disclosed herein by being networked to one or more information storage devices can recognize when it is being asked to deliver medication that is contraindicated by the patient's preexisting medical conditions. Moreover, known laboratory values can alert a device disclosed herein to make adjustments in dosages as an added level of safety. For example, if the laboratory returns an elevated creatinine signaling impairment in renal function, the device will alert the medical provider that cisatraicurium would be the preferred neuromuscular blockading agent. In another example, if a provider tries to give succinylcholine to a patient with hyperkalemia, or administer penicillin to a patient with a history of being allergic to that medication, the device will display a warning on an attached information storage device to alert the provider of the potential problem. A related feature would be checking for allergies among similar classes such as opioids and penicillin. Medications should also be limited for similar ingredients as well as therapeutic families such as beta and calcium channel blockers. All of these details can be efficiently managed by a device disclosed herein. The provider can always override a device disclosed herein by entering one or more user entered commands on user interface that connected to a computer that is networked to a device of the disclosure.

Antibiotic administration two hours prior to surgical incision is the standard of care and increases antibiotic load in blood and tissue to reduce the incidence of postoperative infections. Postoperative deep wound infection, which may be a result of an error of antibiotic omission or forgetting to give an antibiotic dose, is leading cause of iatrogenic injuries. A fluid delivery device disclosed herein can provide a reminder for re-dosing medications. For example, the antibiotic cefazolin which is commonly given intraoperatively is supposed to be dosed every 6 to 8 hours. The device of the disclosure can alert providers by posting an alert on a display that is connected to computer that is connected to a device disclosed herein.

The device can be driven by commands from a user such as a touch-screen or similar input device whereby a user can select a cartridge and the corresponding fluid can be injected into the port. This device can be connected by a cable which transmits electrical instructions between the devices. It can also be connected wirelessly. Instructions for movement are conveyed through a cable or related means by a microprocessor from a computer which activates the fluid delivery track.

Although the specification and illustrations of the present invention contains many preferred embodiments, the invention is not limited to such embodiments and should not be construed as restricting its scope. Instead, this invention provides a suggested illustration of the preferred embodiments. The invention is applicable to other embodiments and configurations as well and includes those apparent to a person skilled in the art to interpret the claims as encompassing all patentable novelties that reside in the present invention.

What is claimed is:

1. A fluid delivery device comprising:

(a) an elongate member having a first and second end;

(b) a plurality of fluid cartridge adapters spaced along the length of the elongate member, wherein each adapter is adapted to receive fluid from a pre-filled removable syringe;

(c) a fluid channel that is centrally disposed within the elongate member and fluidly linked to the fluid cartridge adapters, wherein the fluid channel's first end is enclosed in the elongate member while the second end is operably linked to an exit portal;

(d) one or more pressure modifying devices that are pressureably linked to the fluid channel so that a change in pressure from the pressure modifying device causes liquid to move into the fluid channel;

(e) one or more detectors which can detect one or more machine readable indicators on the barrel of a pre-filled removable syringe once the syringe is inserted into the fluid delivery device, and then output information provided by the machine readable indicator to a computer, wherein one or more machine readable indicators comprise an optical machine-readable representation of data;

(f) a structural housing so dimensioned as to contact the elongate member and restrict the elongate member's movement; and (g) a plurality of syringe holders attached to the structural housing and dimensioned so as to receive the removable syringes and restrict the movement of the syringes from a substantially upright position, wherein the plurality of syringe holders are comprised of a fixed portion and a hingeably attached portion, wherein the hingeably attached portion can be attached and detached from the fixed portion of the holder so as to allow for the insertion of a pre-filled removable syringe.

2. The fluid delivery device of claim 1, wherein the structural housing comprises end supports, one or more motor mount plates, one or more bearing plates, and one or more bearings.

3. The fluid delivery device of claim 2, wherein the structural housing further comprises one or more support rods located an equal distance from a vertically-orientated elongated screw, and one or more syringe plunger drivers that can slide freely vertically up and down the support rods and which can be reversibly attached to the vertically-orientated elongated screw.

4. The fluid delivery device of claim 1, wherein the device further comprises a plurality of pre-filled removable plastic or glass syringes each labeled on the syringe barrel with a machine readable indicator and comprising wherein the machine readable indicator comprises an optical machine-readable representation of data.

5. The fluid delivery device of claim 4, wherein the pre-filled removal syringe further comprises a microchip which provides one or more pieces of information from the group consisting of, identifying a liquid, the status with respect to sterility of a liquid, the concentration of a liquid, volume of a liquid, lot number, dosage instructions, expiration date, drug indication warnings, data to facilitate supply chain management, expenses, and billing.

6. The fluid delivery device of claim 4, wherein the fluid delivery device further comprises one or more one-way valves to prevent fluid from entering the removable syringe through the ejection port.

7. The fluid delivery device of claim 4, wherein the removable syringe is pre-filled with one or more liquids selected from the group consisting of water, aqueous solute solutions, crystalloid solutions, liquids which contain one or more therapeutic agents, liquid intravenous medication, anesthetics, liquid based nutritional substances, and oils.

8. The fluid delivery device of claim 4, wherein the syringes further comprise a conductive material on the top of the glass or plastic syringe plunger.

9. The fluid delivery device of claim 1, wherein the optical machine-readable representation of data can be recognized by either a camera or a bar code scanner.

10. The fluid delivery device of claim 1, wherein one or more pressure modifying devices are pressureably linked to the fluid channel so as to provide positive pressure to push liquid from a removable fluid cartridge into the fluid channel.

11. The fluid delivery device of claim 10, wherein one or more pressure modifying devices are syringe or stepper pumps.

12. The fluid delivery device of claim 1, wherein the device further comprises a computer that that can receive output from a detector.

13. The fluid delivery device of claim 12, wherein the computer is networked to one or more information storage devices.

14. The fluid delivery device of claim 12, wherein the computer further comprises a user interface, where a user can enter commands to control the amount of fluid that is released from each removable fluid cartridge.

15. The fluid delivery device of claim 14, wherein the user by entering commands on a user interface can control the amount of fluid that is released from each removable cartridge by changing the amount or length of time that pressure is applied to one or more removable fluid cartridges.

16. The fluid delivery device of claim 15, wherein the user interface is a touchscreen.

17. The fluid delivery device of claim 1, wherein the fluid cartridge adapters comprise a cap that accommodates syringes that are 3 to 60 mL in volume, and wherein the cap comprises a v-shaped notch that can slideably accommodate a pin or projection on the tip of a pre-filled removable syringe so as to align the syringe in a particular orientation.

18. A method for controlling use of the device of claim 1, comprising:

(1) prompting a user to enter information about personnel and patient information;

(2) detecting a machine readable indicator on the barrel of the pre-filled removable syringe by a detector when the syringe is inserted into the device, wherein the machine readable indicator comprises an optical machine-readable representation of data;

(3) outputting information from the detector to an attached computer about the information provided by the machine readable indicator;

(4) using an algorithm that is programmed into the computer to calculate a proper dose for administering to the patient based on the information outputted to the computer by detector and the user inputted information about the patient; and (5) administering the calculated dose by activating a motor to apply pressure to the pre-filled removable syringe so as to force fluid from the syringe until the calculated dosage is achieve.

* * * * *